US011564996B2

(12) United States Patent
Bennett et al.

(10) Patent No.: US 11,564,996 B2
(45) Date of Patent: Jan. 31, 2023

(54) GENE THERAPY FOR OCULAR DISORDERS

(71) Applicant: The Trustees of the University of Pennsylvania, Philadelphia, PA (US)

(72) Inventors: Jean Bennett, Bryn Mawr, PA (US); Jeannette Bennicelli, Philadelphia, PA (US); Junwei Sun, Philadelphia, PA (US); Ji Yun Song, Lower Gwynedd, PA (US); Sergei Nikonov, Swarthmore, PA (US)

(73) Assignee: The Trustees of the University of Pennsylvania, Philadelpia, PA (US)

( * ) Notice: Subject to any disclaimer, the term of this patent is extended or adjusted under 35 U.S.C. 154(b) by 434 days.

(21) Appl. No.: 16/489,770

(22) PCT Filed: Mar. 1, 2018

(86) PCT No.: PCT/US2018/020470
§ 371 (c)(1),
(2) Date: Aug. 29, 2019

(87) PCT Pub. No.: WO2018/160849
PCT Pub. Date: Sep. 7, 2018

(65) Prior Publication Data
US 2019/0388561 A1   Dec. 26, 2019

Related U.S. Application Data

(60) Provisional application No. 62/469,642, filed on Mar. 10, 2017, provisional application No. 62/465,649, filed on Mar. 1, 2017.

(51) Int. Cl.
*A61K 48/00*   (2006.01)
*C07K 14/47*   (2006.01)
(Continued)

(52) U.S. Cl.
CPC .......... *A61K 48/005* (2013.01); *A61P 27/02* (2018.01); *C12N 15/86* (2013.01);
(Continued)

(58) Field of Classification Search
CPC .... A61K 48/00; A61K 48/05; A61K 48/0075; C07K 14/47; C12N 15/86; C12N 2800/22
See application file for complete search history.

(56) References Cited

U.S. PATENT DOCUMENTS

| 5,139,941 A | 8/1992 | Muzyczka et al. |
| 5,741,683 A | 4/1998 | Zhou et al. |

(Continued)

FOREIGN PATENT DOCUMENTS

| EP | 1310571 | 11/2002 |
| WO | WO 2003/042397 | 5/2003 |

(Continued)

OTHER PUBLICATIONS

Chung et al, Invest. Ophthalmol. & Vis. Sci. 54(15): ARVO Annual Meeting Abstract, 2710, 2013.*

(Continued)

*Primary Examiner* — Kevin K Hill
(74) *Attorney, Agent, or Firm* — Howson & Howson LLP

(57) ABSTRACT

Compositions and methods are provided for treating Leber congenital amaurosis (LCA) in a subject. In one aspect, a recombinant adeno-associated viral vector is provided which includes a nucleic acid molecule comprising a sequence encoding Lebercilin. In another aspect, Lebercilin has an amino acid sequence of SEQ ID NO: 1. In yet another aspect, the nucleic acid molecule has a sequence of SEQ ID NO: 3 or a variant thereof. In desired embodiments, the subject is human, cat, dog, sheep, or non-human primate.

22 Claims, 23 Drawing Sheets

Specification includes a Sequence Listing.

(51) Int. Cl.
*C12N 15/86* (2006.01)
*A61P 27/02* (2006.01)

(52) U.S. Cl.
CPC .............. *A61K 48/0075* (2013.01); *C12N 2750/14122* (2013.01); *C12N 2750/14143* (2013.01); *C12N 2800/22* (2013.01)

(56) References Cited

U.S. PATENT DOCUMENTS

| | | | |
|---|---|---|---|
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,596,535 | B1 | 7/2003 | Carter |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulksi et al. |
| 7,282,199 | B2 | 10/2007 | Gao et al. |
| 7,439,065 | B2 | 10/2008 | Ferrari et al. |
| 7,456,683 | B2 | 11/2008 | Takano et al. |
| 7,588,772 | B2 | 9/2009 | Kay et al. |
| 7,629,322 | B2 | 12/2009 | Kleinschmidt et al. |
| 7,790,449 | B2 | 9/2010 | Gao et al. |
| 7,906,111 | B2 | 3/2011 | Wilson et al. |
| 8,147,823 | B2 | 4/2012 | Acland et al. |
| 10,392,622 | B2 * | 8/2019 | Lewis ................ C12N 15/635 |
| 2004/0022766 | A1 * | 2/2004 | Acland ................ C12N 15/86 424/93.2 |
| 2006/0136184 | A1 | 6/2006 | Gustafsson et al. |
| 2007/0036760 | A1 | 2/2007 | Wilson et al. |
| 2009/0197338 | A1 | 8/2009 | Vandenberghe et al. |
| 2009/2270030 | | 9/2009 | Blotsky et al. |
| 2010/0004323 | A1 * | 1/2010 | Robert-Nicoud ....... A61P 27/02 514/44 R |
| 2014/0032186 | A1 | 1/2014 | Gustafsson et al. |
| 2014/0087444 | A1 * | 3/2014 | Bennett ................ C12N 7/00 435/235.1 |
| 2016/0022836 | A1 * | 1/2016 | Ban ................... A61K 48/005 424/450 |
| 2016/0032319 | A1 | 2/2016 | Wright et al. |
| 2016/0263246 | A1 | 9/2016 | Acland et al. |

FOREIGN PATENT DOCUMENTS

| | | |
|---|---|---|
| WO | WO 2005/033321 | 4/2005 |
| WO | WO 2006/110689 | 10/2006 |
| WO | WO 2010/053572 | 5/2010 |
| WO | WO 2011/126808 | 10/2011 |
| WO | WO 2012/158757 | 11/2012 |
| WO | WO 2012/170930 | 12/2012 |
| WO | WO 2013/049493 | 4/2013 |
| WO | WO 2013/182683 | 12/2013 |
| WO | WO 2014/011210 | 1/2014 |
| WO | WO 2014/124282 | 8/2014 |
| WO | WO 2015/012924 | 1/2015 |
| WO | WO 16/019364 * | 2/2016 |
| WO | WO 2016/019364 | 2/2016 |

OTHER PUBLICATIONS

Fumoto et al (INTECH, Novel Gene Therapy Approaches, p. 3-31; editors Wei and Good, publisher Books on Demand, 2013).*
Daya et al, Clin. Microbiol. Rev. 21(4): 583-593, 2008.*
Mingozzi and High, Blood 122(1): 23-36, 2013.*
Kattenhorn et al, Human Gene Therapy 27(12): 947-961, Nov. 28, 2016.*
Perrin, Nature (507): 423-425, 2014.*
GenBank Accession AF334827, pTurbo-Cre, (2002).*
GenBank Accession GU299216, pCAGGS-T7, (2010).*
GenBank BC050327, 2007.*
Ahmad et al., Identification of a novel LCA5 mutation in a Pakistani family with Leber congenital amaurosis and cataracts, Molecular Vision, vol. 17:1940-5, Jul. 2011.
Ashtari et al., The human visual cortex responds to gene therapy-mediated recovery of retinal function, Journal Clinical Investigation, vol. 121(6):2160-8, Jun. 2011.
Banin et al., Molecular anthropology meets genetic medicine to treat blindness in the north african Jewish population: human gene therapy initiated in Israel, Human Gene Therapy, vol. 21(12):1749-57, Dec. 2010.
Beltran et al., rAAV2/5 gene-targeting to rods: dose-dependent efficiency and complications associated with different promoters, Gene Therapy, vol. 17(9):1162-1174, Sep. 2010.
Bennett et al., AAV2 gene therapy readministration in three adults with congenital blindness, Science Translational Medicine, vol. 4(120):120ra15, Feb. 2012.
Bennett et al., Safety and durability of effect of contralateral-eye administration of AAV2 gene therapy in patients with childhood-onset blindness caused by RPE65 mutations: a follow-on phase 1 trial, Lancet, vol. 388(10045):661-72, Aug. 2016.
Brainbridge et al., Effect of gene therapy on visual function in Leber's congenital amaurosis, The New England Journal of Medicine, vol. 358(21)2231-9, May 2008.
Boldt et al., Disruption of intraflagellar protein transport in photoreceptor cilia causes Leber congenital amaurosis in humans and mice, Journal of Clinical Investigation, vol. 121(6):2169-80, Jun. 2011.
Buning et al., Recent Developments in Adeno-Associated Virus Vector Technology, Journal of Gene Medicine, vol. 10(7):717-733, Jul. 2008.
Cai et al., A 350 bp region of the proximal promoter of Rds drives cell-type specific gene expression, Expert Eye Research, vol. 91(2): 186-194, Aug. 2010.
Chen et al., Next-generation Sequencing Extends the Phenotypic Spectrum for LCA5 Mutations: Novel LCA5 Mutations in Cone Dystrophy, Scientific Reports, vol. 6:24357, Apr. 2016.
Cideciyan et al., Human retinal gene therapy for Leber congenital amaurosis shows advancing retinal degeneration despite enduring visual improvement, PNAS, vol. 110(6):E517-25, Feb. 2013.
Corton et al., Involvement of LCA5 in Leber congenital amaurosis and retinitis pigmentosa in the Spanish population, Ophthalmology, vol. 121(1):399-407, Jan. 2014.
Daber et al., A Novel Molecular Switch, Journal Molecular Biology, vol. 391(4):661-70, Aug. 2009.
Dalkara et al., In Vivo-Directed Evolution of a New Adeno-Associated Virus for Therapeutic Outer Retinal Gene Delivery from the Vitreous, Science Translational Medicine, vol. 5:189ra76, Jun. 2013.
Dalkara et al., Inner limiting membrane barriers to AAV-mediated retinal transduction from the vitreous, Molecular Therapy, vol. 17(12):2096-2102, Dec. 2009.
Damdindorj et al., A Comparative Analysis of Constitutive Promoters Located in Adeno-Associated Viral Vectors, PLoS One, vol. 9(8):e106472, Aug. 2014.
David et al., Recombinant adeno-associated virus-mediated in utero gene transfer gives therapeutic transgene expression in the sheep, Human Gene Therapy, vol. 22(4):419-26, Apr. 2011.
Den Hollander et al., Mutations in LCA5, encoding the ciliary protein lebercilin, cause Leber congenital amaurosis, Nature Genetics, vol. 39:889-895, Jun. 2007.
Diehl et al., A Good Practice Guide to the Administration of Substances and Removal of Blood, Including Routes and Volumes, Journal of Applied Toxicology, vol. 21:15-23, Feb. 2001.
Fisher et al., Transduction with Recombinant Adeno-Associated Virus for Gene Therapy is Limited by Leading-Strand Synthesis, Journal of Virology, vol. 70(1):520-532, Jan. 1993.
Gerber et al., Mutations in LCA5 are an uncommon cause of Leber congenital amaurosis (LCA) type II, Human Mutation, vol. 28(12): 1245, Dec. 2007.

(56) References Cited

OTHER PUBLICATIONS

Georgiadis et al., Development of an optimized AAV2/5 gene therapy vector for Leber Congenital Amaurosis owing to defects in RPE65, Gene Therapy, vol. 23(12):857-862, Sep. 2016.
Grieger & Samulski, Adeno-associated virus as a gene therapy vector: Vector development, production and clinical applications, Advanced Biochemical Engineering/Biotechnology, vol. 99:119-145, Oct. 2005.
Jacobson et al., Gene Therapy for Leber Congenital Amaurosis caused by RPE65 mutations: Safety and Efficacy of Fifteen Children and Adults Followed up to Three Years, Arch Opthalmology, vol. 130(1):9-24, Jan. 2012.
Jacobson et al., Leber congenital amaurosis caused by Lebercilin (LCA5) mutation: retained photoreceptors adjacent to retinal disorganization, Molecular Vision, vol. 15:1098-106, Jun. 2009.
Kachi et al., Equine Infectious Anemia Viral Vector-Mediated Codelivery of Endostatin and Angiostatin Driven by Retinal Pigmented Epithelium-Specific VMD2 Promoter Inhibits Choroidal Neovascularization, Human Gene Therapy, vol. 20:31-9, Jan. 2009.
Kay et al., Targeting Photoreceptors via Intravitreal Delivery Using Novel, Capsid-Mutated AAV Vectors, PLoS One, vol. 8(4):e62097, Apr. 2013.
Lambard et al., Expression of Rod-Derived Cone Viability Factor: Dual Role of CRX in Regulating Promoter Activity and Cell-Type Specificity, PLoS One, vol. 5(10):e13025, Oct. 2010.
Liang et al., Intraocular delivery of recombinant virus, Methods Molecular Medicine, vol. 47:125-39, Jan. 2001.
Lock et al., Absolute Determination of Single-Stranded and Self-Complementary Adeno-Associated Viral Vector Genome Titers by Droplet Digital PCR, Human Gene Therapy Methods, vol. 25(2):115-25, Apr. 2014.
Mace et al., Targeting channelrhodopsin-2 to ON-bipolar cells with vitreally administered AAV Restores ON and OFF visual responses in blind mice, Molecular Therapy, vol. 23(1):7-16, Jan. 2015.
Mackay et al., Screening of a large cohort of leber congenital amaurosis and etinitis pigmentosa patients identifies novel LCA5 mutations and new genotype-phenotype correlations, Human Mutations, vol. 34(11):1537-46, Nov. 2013.
Maguire et al., Phase 3 trial of AAV2-hRPE65v2 (SPK-RPE65) to treat RPE65 mutation-associated inherited retinal dystrophies, Lancet, vol. 374(9701):1597-1605, Nov. 2009.
McCarty et al., Self-complementary recombinant adeno-associated virus (scAAV) vectors promote efficient transduction independently of DNA synthesis, Gene Therapy, vol. 8(16):1248-1254, Aug. 2001.
McLaughlin et al., Adeno-Associated Virus General Transduction Vectors: Analysis of Proviral Structures, Journal of Virology, vol. 62(6):1963-973, Jun. 1998.
Mohamed et al., Progression of phenotype in Leber's congenital amaurosis with a mutation at the LCA5 locus, The British Journal of Ophthalmology, vol. 87(4):473-5, Apr. 2003.
Morrisey et al., PRE-1 a cis element sufficient to enhance cone-and-rod-pecific expression in differentiating zebrafish photoreceptors, BMC evelopmental Biology, vol. 11:3, Jan. 2011.
Mowat et al., Tyrosine Capsid-Mutant AAV Vectors for Gene Delivery to the Canine Retina from a Subretinal or Intravitreal Approach, Gene Therapy, vol. 21(1):96-105, Jan. 2014.
Mussolino et al., AAV-mediated photoreceptor transduction of the pig cone-enriched retina, Gene Therapy, vol. 18(7):637-45, Jul. 2011.
Nicord et al., Development of photoreceptor-specific promoters and their utility to investigate EIAV lentiviral vector mediated gene transfer to photoreceptors, The Journal of Gene Medicine, vol. 9(12):1015-23, Dec. 2007.
Ogueta et al., The Human cGMP-PDE β-Subunit Promoter Region Directs Expression of the Gene to Mouse Photoreceptors, IVOS, vol. 41(13):4059-63, Dec. 2000.
Ramachandran et al., Evaluation of Dose and Safety of AAV7m8 and AAV8BP2 in the Non-Human Primate Retina, Human Gene Therapy, vol. 28(2):154-167, Feb. 2017.
Redmond et al., Genetic analysis of RPE65: from human disease to mouse model, Methods in Enzymology, vol. 316:705-724, 2000.
Redmond et al., RPE65 is necessary for production of 11-cis-vitamin A in the retinal visual cycle, Nature Genetics, vol. 20(4):344-51, Dec. 1998.
Seong et al., LCA5, a rare genetic cause of leber congenital amaurosis in Koreans, Ophthalmic Genetics, vol. 30(1):54-5, Mar. 2009.
Sochor et al., An Autogenously Regulated Expression System for Gene Therapeutic Ocular Applications, Scientific Reports, vol. 5:17105, Nov. 2015.
Su et al., In Vitro and in Vivo mRNA Delivery Using Lipid-Enveloped pH-responsive Polymer Nanoparticles, Molecular Pharmaceutics, vol. 8(3):774-87, Jun. 2011.
Sun et al., Gene Therapy with a Promoter Targeting Both Rods and Cones Rescues Retinal Degeneration Caused by AIPL1 Mutations, Gene Therapy, vol. 17(1): 117-131, Jan. 2010.
Thompson et al., A comprehensive comparison of multiple sequence alignments, Nucleic Acids Research, vol. 27(13):2682-2690, May 1999.
Vallespin et al., Novel human pathological mutations. Gene symbol: LCA5. Disease: Leber congenital amaurosis, Human Genetics, vol. 127(1):118, Jan. 2010.
Vandenberghe et al., Dosage Thresholds for AAV2 and AAV8 Photoreceptor Gene Therapy in Monkey, Science Translational Medicine, vol. 3(88):88ra54, Jun. 2011.
Weleber et al., Results at 2 Years after Gene Therapy for RPE65-Deficient Leber Congenital Amaurosis and Severe Early-Childhood-Onset Retinal Dystrophy, Opthalmology, vol. 123(7):1606-20, Apr. 2016.
Zhang et al., Adenovirus-adeno-associated virus hybrid for large-scale recombinant adeno-associated virus production, Human Gene Therapy, vol. 20:922-929, Sep. 2009.
International Search and Written Opinion dated May 18, 2018, issued in International Patent Application No. PCT/US2018/020470.
Song et al., "rAAV-mediated gene augmentation improves retinal and visual function and retinal structure in a mouse model for LCA5," Investigative Ophthalmology & Visual Science, vol. 57(12):5151, Sep. 2016.
Song et al., "Amelioration of Neurosensory Structure and Function in Animal and Cellular Models of a Congenital Blindness," Molecular Therapy, vol. 26(6):1581-1593, Jun. 2018.
Extended European Search Report issued in European Patent Application No. 8760861.7, dated Dec. 3, 2020.

* cited by examiner

FIG. 1A

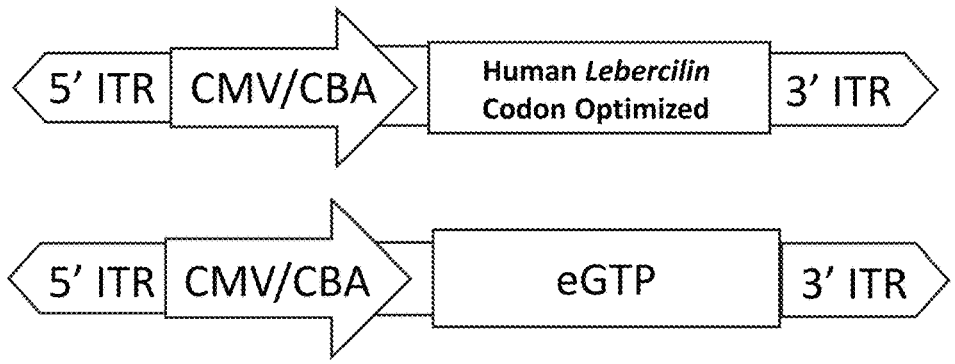

FIG. 1B

```
Native_LCAS              atggggaaagagcaggaagtccaggtactgaccaagaaagaaaggcaggcaaacaccat    60
Codon-optimized_LCAS     atgggagaacgagcaggcagccctggtacggaccaggaacgcaaggcggggaaacaccac    60
                         ****  *   ******  **  *  ****  **** ***  * *  ***  ** *******

Native_LCAS              tattcttacttatctgattttgaaacgccacagtcttctggccgatcatcgctggtcagt    120
Codon-optimized_LCAS     tatagctatttgtcagactttgagacaccgcagagctcgggtcggtcatccttggtgtcg    120
                         ***   **  **  ** ****** ** **  ***  ** ***  *  **** **** * *

Native_LCAS              tcttcacctgcaagtgttaggagaaaaaatcctaaaagacaaacttcagatggccaagta    180
Codon-optimized_LCAS     tcaagcccggctagcgtccggcgaaagaatccaaagcgccaaacgtcagatggccaggtg    180
                         **   * **  *  * **  ** ****  *****  ** ***** ************* * *

Native_LCAS              catcaccaagcccctcggaaaccaagccccaagggtctaccaaacagaaagggagtccga    240
Codon-optimized_LCAS     catcatcaggctccccggaaaccctcgccccaaaggattgccgaacagaaaggggggtccgg    240
                         *****  **   * ****** **  *  ** ** ** *  * *********** *  ****

Native_LCAS              gtgggatttcgctcccagagcctcaatagagagccacttcggaaagatactgatcttgtt    300
Codon-optimized_LCAS     gtagggtttagatcgcagagcctgaatcgcgagcctcttagaaaagatacagaccttgtg    300
                         ** ** *** *  * ******** *** * ***** ** *** ******* ** *****

Native_LCAS              acaaaacggattctgtctgcaagactgctaaaaatcaatgagttgcagaatgaagtatct    360
Codon-optimized_LCAS     actaagaggattctgtcggcacgactgttgaagattaacgaacttcagaatgaggtgtca    360
                         ** **  *********  ***  ***** *  *  ** *** ** ****** *  **  *

Native_LCAS              gaactccaggtcaagttagctgagctgctaaaagaaaataaatctttgaaaaggcttcag    420
Codon-optimized_LCAS     gaactccaagtaaaacttgcggaactgcttaaggagaacaaatcgctcaagcggcttcag    420
                         ********  * **  * *  ** *****  **  **  ***** * ** * *******

Native_LCAS              tacagacaggagaaagccctgaataagttgaagatgccgaaaatgaaatctcacaaactt    480
Codon-optimized_LCAS     tatcgccaagagaaagcgctcaacaagttcgaggacgcggaaaacgagatttcgcagttg    480
                         **  * ** ********* ** ** *****  ** **  *****  * **  *  * * *

Native_LCAS              atatttcgtcataacaatgagattacagcactcaaagaacgcttaagaaaatctcaagag    540
Codon-optimized_LCAS     atctttaggcataacaacgagatcaccgcccttaaagaacgcttgcgcaaaagccaggag    540
                         ** *** *  *******  ***** ** ** ** ********** *  *** **  ****

Native_LCAS              aaagaacgggcaactgagaaagggtaaaagatacagaaagtgaactatttaggacaaaa    600
Codon-optimized_LCAS     aaagaacgccgccacggagaagagggtcaaggacaccgaatcggaactgtttagaactaag    600
                         ********  * ** ****** ** * *  **** * *** *  *** **** ** ** *

Native_LCAS              ttttccttacagaaactgaaagagatctctgaagctagacacctacctgaacgagatgat    660
Codon-optimized_LCAS     tttcgcttcaaaagcttaaagaaatctcggaagcgaggcatctccctgagcgagatgat    660
                         **** * **  *  * * ****** *** *****  **  ** * ***** *********

Native_LCAS              ttggcaaagaaactagtttcagcagagttaaagttagatgacaccgagagaagaattaag    720
Codon-optimized_LCAS     ttggctaagaaacttgtatcggcagagctcaaattggatgatacggagaggaggattaag    720
                         ***** ****** * **  ** ******* ***  * ***** ** ***** ** *****
```

FIG. 1C

```
Native_LCAS            gagctatcgaaaaaccttgaactgagtactaacagtttccaacgacagttgcttgctgaa  780
Codon-optimized_LCAS   gaacttagcaaaaaccttgaattgtcaacgaactcgtttcaacggcagctgttggccgaa  780
                       ** **  ************ **   **  ***   ** *****  ***  **  *  ***

Native_LCAS            aggaaaagggcatatgaggctcatgatgaaaataaagttcttcaaaaggaggtacagcga  840
Codon-optimized_LCAS   agaaaacgggcttatgaagcgcacgatgaaaacaaggtgctgcagaaagaggtgcagagg  840
                       **  ***  ***  *****  **  ********  **  **  ** *****  *** * *

Native_LCAS            ctatatcacaaattaaaggaaaaggagagagaactggatataaaaaatatatattctaat  900
Codon-optimized_LCAS   ttgtaccataagctgaaagagaaggaaagagagctggacatcaaaaacatctacagcaac  900
                        * *  ** **    * **  ** ***** ***** ***  **  ***** * **   **

Native_LCAS            cgtctgccaaagtcctctccaaataaagagaaagaacttgcattaagaaaaaatgctgca  960
Codon-optimized_LCAS   cggctgcctaagtcatcgccaaacaaagagaaagagctggcattgagaaagaatgcagcc  960
                       **  *****  ****  *  **** ********** * ****** ****  *****  *

Native_LCAS            tgccagagtgattttgcagacctgtgtacaaaaggagtacaaaccatggaagacttcaag  1020
Codon-optimized_LCAS   tgccagtcggatttgcgatctgtgcacgaaaggagtacagaccatggaggactttaag  1020
                       ******   ****** *  ***** **  **********  ********* *** ***

Native_LCAS            ccagaagaatatcctttaactccagaaacaattatgtgttacgaaaacaaatgggaagaa  1080
Codon-optimized_LCAS   cccgaagaataccccacttacacccgagacaatcatgtgttacgagaacaagtgggaggag  1080
                       ** *********  *  * **  ****  *** **********  *****  *****  *

Native_LCAS            ccaggacatcttactttggacttgcaatctcaaaagcagacaggcatggagaagcaggg  1140
Codon-optimized_LCAS   ccgggacaccttactcttgatctccagagccaaaaacaggatcgccacggcgaggccggt  1140
                       ** *****  *****   **  *     * **** **  *      *   ****    **

Native_LCAS            attctaaacccaattatggaaagagaagaaaaatttgttacagatgaagaactccatgtc  1200
Codon-optimized_LCAS   attctcaacccgatcatggagagagaggagaagttcgtcacagatgaggagctccacgtc  1200
                       *****  ****  ** **** ******* **  *   **  ********  *****  **

Native_LCAS            gtaaaacaggaggttgaaaagctggaggatgaatgggaaagagaagaacttgataaaaag  1260
Codon-optimized_LCAS   gtgaaacaagaagtggagaagctcgaggacgaatgggaacgagaagagcttgataagaag  1260
                       ** *****  **  **  *****  *****  ******  ***** * ********   **

Native_LCAS            caaaaagaaaaggcatctttactggaaagagaagaaaaagccagagtgggaaactggaagg  1320
Codon-optimized_LCAS   cagaaggagaaagcatcgttgctggaacgcgaagagaaaccggagtgggagactggaagg  1320
                       **  **   ** ***   *  *****    **** **  * *********  *******

Native_LCAS            taccaactaggaatgtatccaattcagaatatggataaattgcaaggagaggaagaagaa  1380
Codon-optimized_LCAS   tatcagcttgggatgtacccaattcagaatatggacaaactccaggggaggaagaagag  1380
                       **  **   * *******  **  *********** **  *  **  ** *********

Native_LCAS            agactgaagagagaaatgctacttgctaaactgaatgaaattgacagagaactccaagat  1440
Codon-optimized_LCAS   aggctcaagagggaaatgctcctggccaagttgaatgagattgaccggagttgcaagac  1440
                       **  * ***** ******** ** **  **  ****** *****  *  *    *****

Native_LCAS            tctcgaaatctaaaataccctgttttgccattgttacctgattttgaatcaaaactacac  1500
Codon-optimized_LCAS   tcacgcaacctcaagtaccctgtactccccctgcttccggatttgaatcaaaacttcac  1500
                       **  *  ** **  * ********  ***   **  **  *****************  **

Native_LCAS            tccccagagagaagccccaaaacatacaggttctctgaatcctcagagagattatttaat  1560
Codon-optimized_LCAS   tccccgaacggagccccaagaccatcgattctcggaatcgtcggagagactcttcaat  1560
                       ***** **  * ********  ****  * ****   ****   ** ****    * ***

Native_LCAS            gggcatcatttgcaagacatcagtttctcaactccaaaaggagaaggtcagaattcagga  1620
Codon-optimized_LCAS   ggacaccatttgcaagacatctcctttcaacacccaaaggggaaggccagaattccgga  1620
                       **  ** ************    ** **  * ** ****** ****** ****** ***

Native_LCAS            aatgttagaagtccagcctcccctaatgagttcgcatttggtagctacgtgccttcgttt  1680
Codon-optimized_LCAS   aatgtgcggtcgccagcgtcgccaaatgagttcgcattcggttcgtacgtgccctcattc  1680
                       *****    *    ****  *   ****************  *  *******  **   *

Native_LCAS            gcaaaaacatcagagaggtcaaatccatttagtcaaaaaagtagtttttttggatttccaa  1740
Codon-optimized_LCAS   gcgaaaacctcggagagatccaaccccttcagccaaaagtcgtcattcttggatttccag  1740
                       ** *****  *  ****** *   * * ** ** ******  **  * * **********
```

FIG. 1D

```
Native_LCAS            agaaacagtatggaaaaacttagtaaagatggtgtagatttaattacaagaaaagagaaa  1800
Codon-optimized_LCAS   agaaactccatggaaaagctctccaaggatggagtcgatctcatcactagaaaagagaag  1800
                       ******  ********  **   ** *****  ** ***  ** ** ** *********

Native_LCAS            aaagctaatttgatggaacagttatttggtgccagtggtagcagccaccatttcctccaaa  1860
Codon-optimized_LCAS   aaggccaatctcatggaacagttgttcggagcgtcgggttcgtccaccatctcctccaag  1860
                       ** ** ***  * ***********  ** **  **          ***    ****** ********

Native_LCAS            agcagtgacccaaattctgtggcttccagtaaaggagacattgaccctctaaattttctc  1920
Codon-optimized_LCAS   tcatcagaccccaattcggtcgcatcctcaaagggagacatcgaccctttgaatttcctg  1920
                          *****  *****  **  ** ** *    ** ******** ***** * ***** **

Native_LCAS            cctgggaataaaggcagcagagatcaagaacatgatgaagatgaaggcttttttcctcagt  1980
Codon-optimized_LCAS   ccgggaaacaaggggttcgcgagatcaggaacatgacgaggacgaggggttttttcttgtcc  1980
                       ** ** ** ** **  ******* ******** ** ** ** ** ****** *

Native_LCAS            gaaggaagaagttttaatccaaataggcaccgattaaaaacatgcagacgataaaccagca  2040
Codon-optimized_LCAS   gaagggaggtccttcaatccgaatcgccacagattgaaacacgcggatgacaagcctgcg  2040
                       *****  **   ** ** ***  ***  *** ***** ***** ** ** ** ** **

Native_LCAS            gtaaaagcagctgattctgtagaagatgaaattgaagaagtagcactgagatga         2094
Codon-optimized_LCAS   gtgaaggctgcggactcagtagaggacgagatcgaggaagtggccctgagatga         2094
                       ** ** ** ** ** ** ** *****  ** ** ** ** ****** ** *********
```

| bla txn terminator | 4473...4773 | 301 | == |
| rpn txn terminator | 4780...4893 | 114 | == |
| lambda stuffer | 4909...9975 | 5067 | == |
| pUC ori | 10,267...10,855 | 589 | <= |
| KanR | 10,979...11,788 | 810 | <= |
| source | 10,980...10,979 | 12231 | == |
| AmpR promoter | 11,789...11,880 | 92 | <= |
| rrnB1 B2 T1 txn terminator | 11,967...12,141 | 175 | <= |
| FRT (minimal) | 12,173...12,206 | 34 | => |

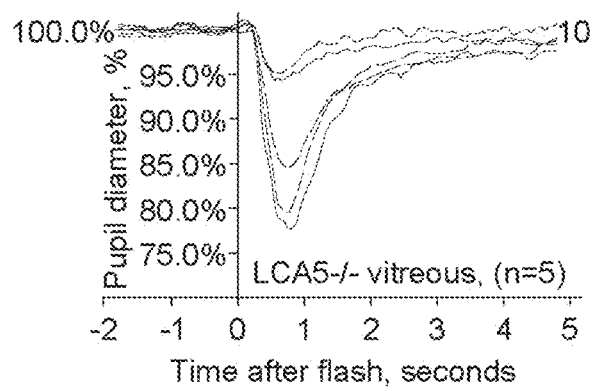
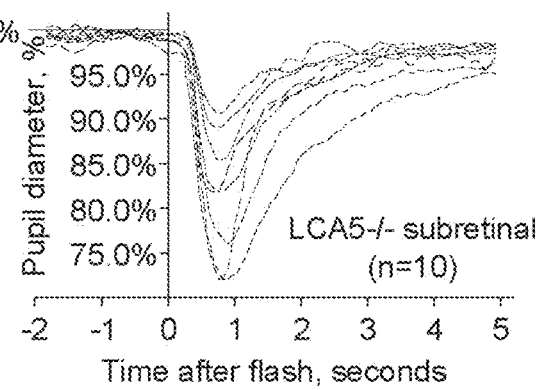
FIG. 2A          FIG. 2B
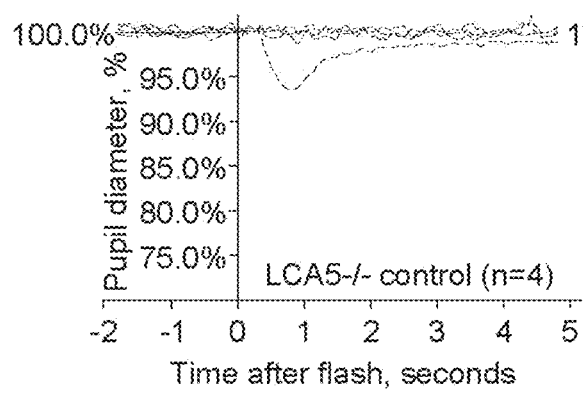
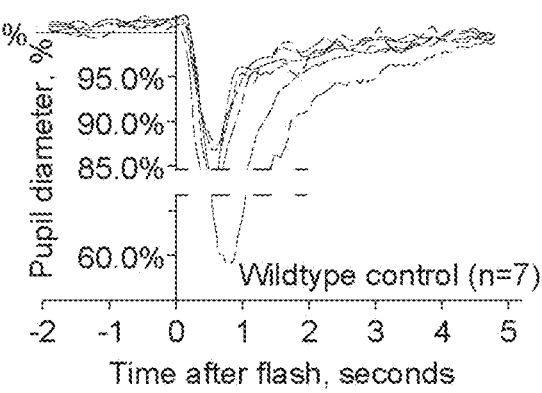
FIG. 2C          FIG. 2D
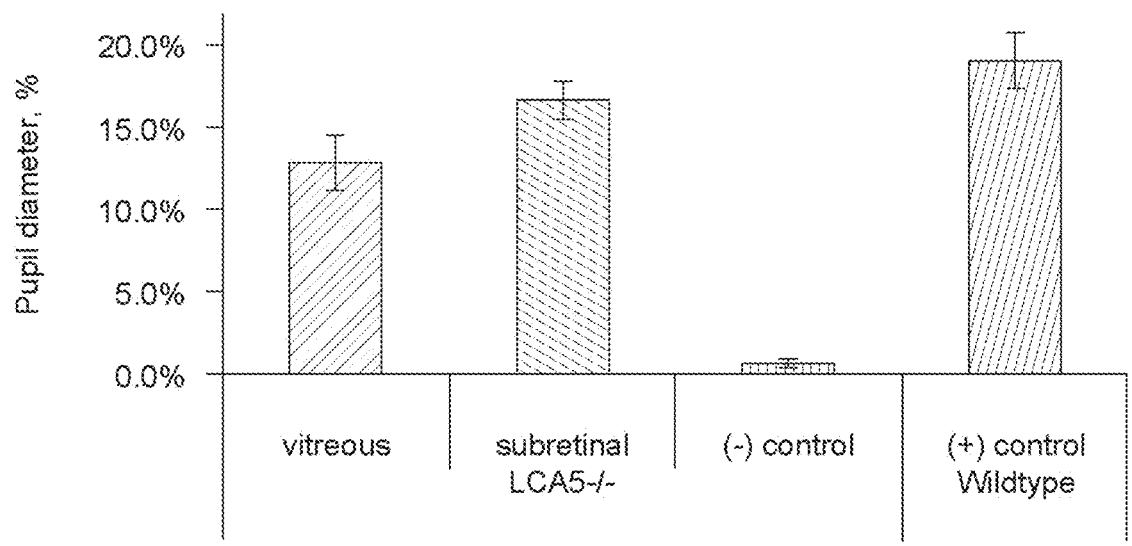
FIG. 2E

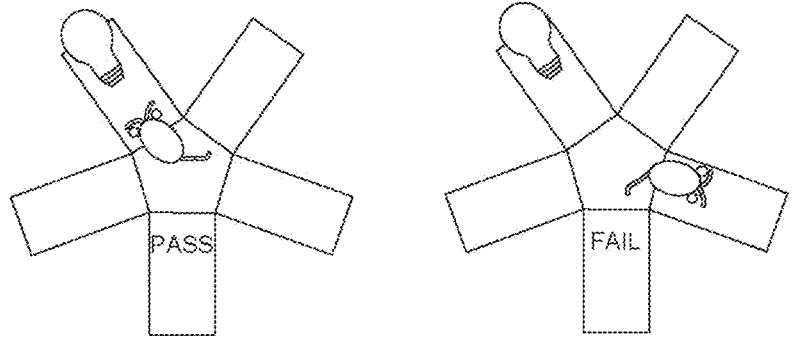
FIG. 3A
FIG. 3B
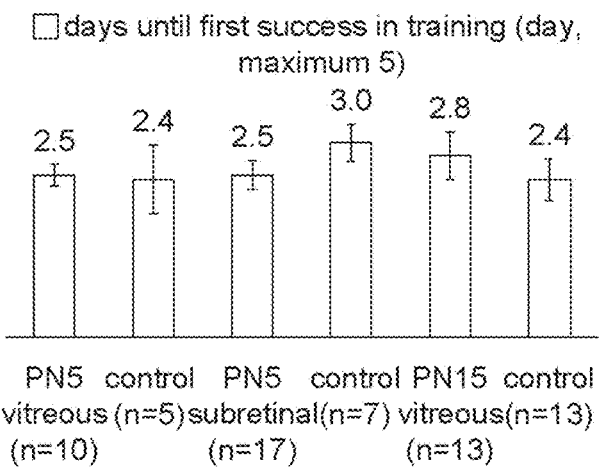
FIG. 3C
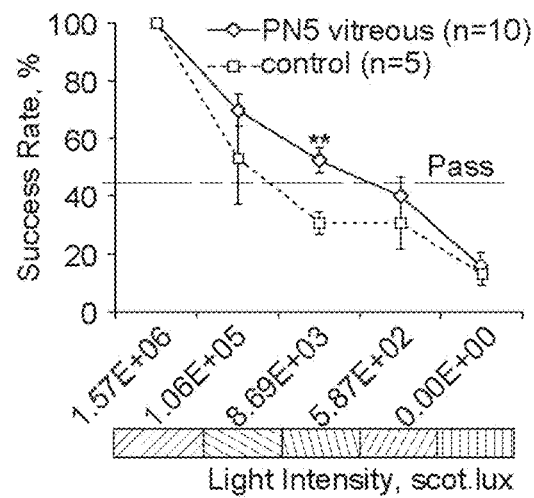
FIG. 3D
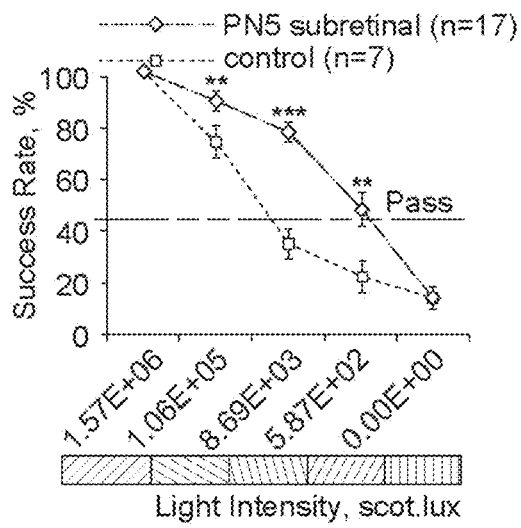
FIG. 3E
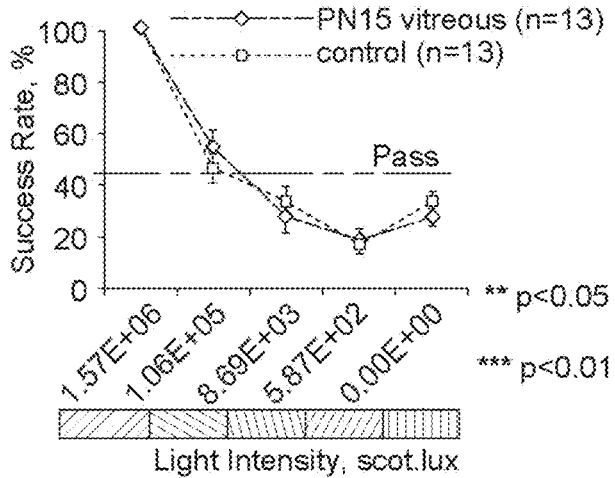
FIG. 3F
** $p<0.05$
*** $p<0.01$

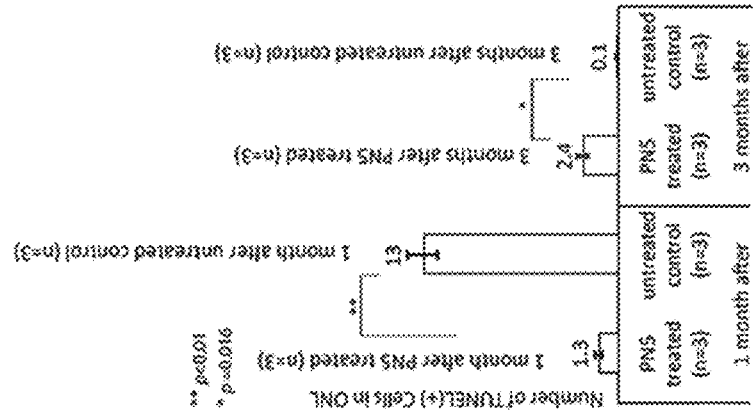
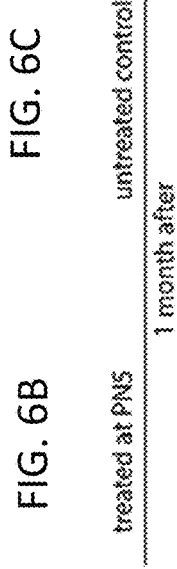
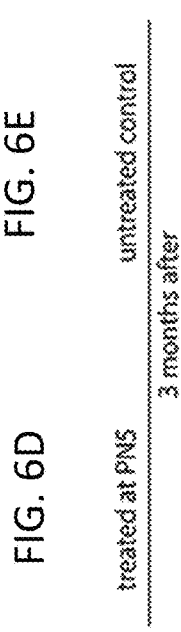
FIG. 6A
FIG. 6B  FIG. 6C  FIG. 6D  FIG. 6E

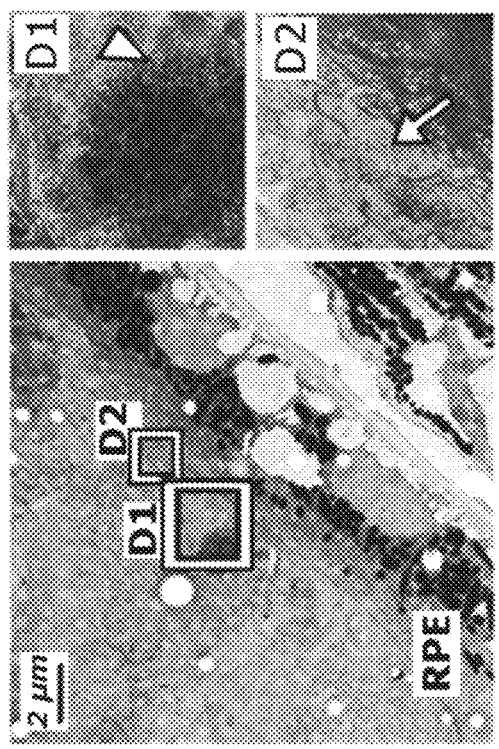
FIG. 7D
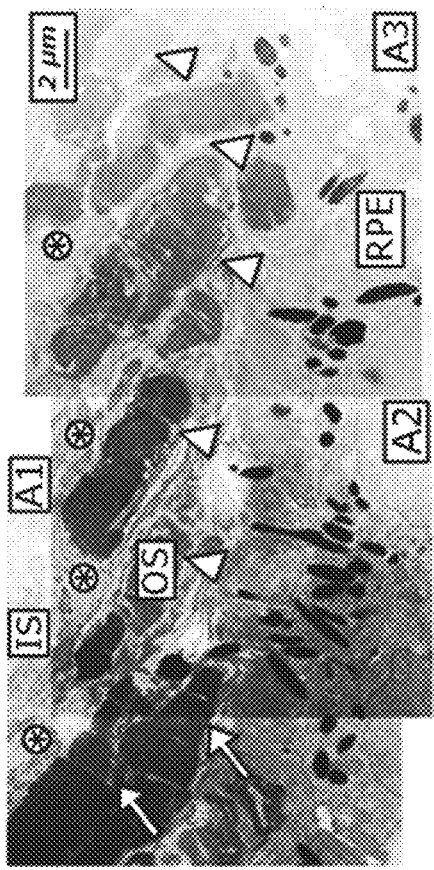
FIG. 7A
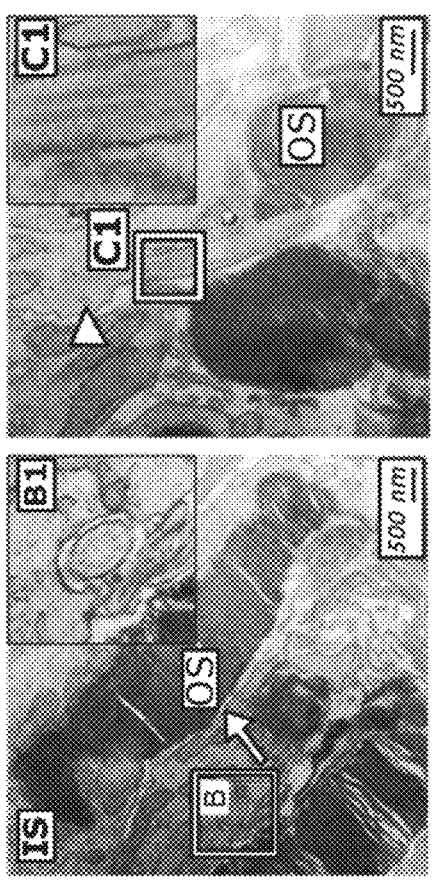
FIG. 7C
FIG. 7B

FIG. 11B

| Features | | | |
|---|---|---|---|
| 5' ITR | 1...130 | 130 | == |
| ITR D segment | 113...130 | 18 | == |
| CMV enhancer | 241...544 | 304 | == |
| chicken beta-actin promoter | 546...823 | 278 | => |
| CBA exon1 and intron | 824...1795 | 972 | == |
| human native Lebercilin | 1853...3970 | 2118 | == |
| bGH poly(A) signal | 3982...4189 | 208 | == |
| 3' ITR | 4239...4368 | 130 | == |
| ITR D segment | 4239...4256 | 18 | == |
| FRT (minimal) | 4396...4429 | 34 | <= |
| bla txn terminator | 4462...4762 | 301 | == |
| rpn txn terminator | 4769...4882 | 114 | == |
| lambda stuffer | 4898...9964 | 5067 | == |
| pUC ori | 10,256...10,844 | 589 | <= |

| | | | |
|---|---|---|---|
| KanR | 10,968...11,777 | 810 | <= |
| source | 10,969...10,968 | 12220 | == |
| AmpR promoter | 11,778...11,869 | 92 | <= |
| FRT (minimal) | 12,162...12,195 | 34 | => |

GENE THERAPY FOR OCULAR DISORDERS

CROSS-REFERENCE TO RELATED APPLICATIONS

This is a National Stage Entry under 35 U.S.C. 371 of International Patent Application No. PCT/US2018/020470, filed Mar. 1, 2018, which claims priority to U.S. Provisional Patent Application No. 62/465,649, filed Mar. 1, 2017 and U.S. Provisional Patent Application No. 62/469,642, filed Mar. 10, 2017. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7696PCT_Seq_Listing_ST25.txt".

BACKGROUND OF THE INVENTION

One of the most severe groups of inherited blinding diseases is Leber congenital amaurosis (LCA; OMIM 204000). LCA is rare, occurring in 1:50,000 individuals, is usually inherited in an autosomal recessive fashion, and can be caused by mutations in any of at least 22 different genes (sph.uth.edu/RetNet/sum-dis.htm). Clinical features include severely abnormal vision (visual acuity, reduced visual fields) in infancy or early childhood, nystagmus, and progressive loss of the poor vision that exists early in life. Clinical testing reveals extinguished scotopic and photopic electroretinogram (ERG) responses, amaurotic pupils, reduced light sensitivity, and pigmentary changes in the retina. There is currently no approved treatment for LCA.

A form of LCA that is caused by mutations in the retinal pigment epithelium 65 kDa protein-encoding gene, RPE65 (Redmond T M, Yu S, Lee E, Bok D, Hamasaki D, Chen N, et al. Rpe65 is necessary for production of 11-cis-vitamin A in the retinal visual cycle. Nat Genet (1998) 20(4):344-51; Redmond T, Hamel C. Genetic analysis of RPE65: from human disease to mouse model. Methods in Enzymol (2000) 317:705-24, both of which are incorporated herein by reference), has received a great deal of attention in recent years as it has been the target of multiple gene augmentation therapy clinical trials. Using adeno-associated virus (AAV) serotype 2, several groups have shown that delivery of the wildtype copy of the RPE65 cDNA to the retinal pigment epithelium (RPE) is safe, and that this can reverse many of the deficits, including nyctalopia.(3-9) A randomized, multi-center Phase 3 study testing AAV2-hRPE65v2 (or voretigene neparvovec, sponsored by Spark Therapeutics, Philadelphia, Pa.), has shown that subretinal injection of this reagent leads to improvements in light sensitivity, visual fields and even the ability to navigate accurately and quickly using visual cues over a range of luminance conditions.(10, 11) The US Food and Drug Administration (FDA) granted drug approval for Voretigene neparvovec-rzyl on Dec. 19, 2017, making this one of the first approved gene therapy drugs in the USA. The progress in developing a treatment for LCA caused by RPE65 mutations, LCA2, paves the way for development of treatments for other forms of early onset retinal degeneration, most of which are caused by mutations in photoreceptor-specific genes, not just RPE-specific genes.

One of the most severe forms of this already severe condition (LCA) is caused by mutations in the photoreceptor-specific gene encoding Lebercilin, LCA5 (12-20). LCA5 mutation is estimated to account for ~2% of cases of LCA although it may be more prevalent in populations that are genetically isolated.(16) LCA5 mutations have also been identified as the cause of other early onset forms of retinal degeneration, including cone dystrophy and autosomal recessive retinitis pigmentosa (ARRP).(15, 16, 21)

Therefore, compositions useful for expressing Lebercilin in subjects in need are needed.

SUMMARY OF THE INVENTION

The embodiments described herein are directed to compositions and methods relating to an AAV gene therapy vector for delivering human LCA5 to a subject in need thereof, following intravitreal or subretinal administration of the vector resulting in long-term, perhaps 10 years or more, of clinically meaningful correction of Leber congenital amaurosis (LCA).

In one aspect, a codon optimized, engineered nucleic acid sequence encoding human Lebercilin is provided. In one embodiment, the codon optimized nucleic acid sequence is a variant of SEQ ID NO: 3 or SEQ ID No: 2. In another embodiment, the codon optimized nucleic acid sequence is SEQ ID NO: 3. In another embodiment, the nucleic acid sequence is codon optimized for expression in humans.

In another aspect, an expression cassette comprising a codon optimized nucleic acid sequence that encodes Lebercilin is provided. In one embodiment, the expression cassette includes the nucleic acid sequence of SEQ ID NO: 3 encoding human Lebercilin. In still other embodiments, the Lebercilin encoding sequence is positioned between 5' and 3' AAV ITR sequences.

In yet another aspect, a recombinant adeno-associated virus (rAAV) vector is provided. The rAAV compromises an AAV capsid, and a vector genome packaged therein. In one embodiment, the vector genome comprises: (a) an AAV 5' inverted terminal repeat (ITR) sequence; (b) a promoter; (c) a coding sequence encoding a human Lebercilin; and (d) an AAV 3' ITR. In one embodiment, the rAAV vector further comprises expression control sequences that direct expression of the Lebercilin in a host cell. In further embodiment, the Lebercilin sequence is the protein sequence of SEQ ID NO: 1. In one embodiment, the vector genome is the sequence of nt 1-4379 of SEQ ID NO: 8. In another embodiment, the vector genome is the sequence of nt 1-4368 of SEQ ID NO: 9. In yet another embodiment, the LCA5 coding sequence in either of the identified vector genomes is swapped with another LCA5 coding sequence as described herein.

In another aspect, an aqueous suspension suitable for administration to an LCA patient is provided. In one embodiment, the suspension comprises an aqueous suspending liquid and about $1 \times 10^{10}$ GC or viral particles to about $1 \times 10^{13}$ GC or viral particles per eye of a recombinant adeno-associated virus (rAAV) described herein useful as a therapeutic for LCA.

In another aspect, a pharmaceutical composition comprises a pharmaceutically acceptable carrier, diluent, excipient and/or adjuvant and the nucleic acid sequence, a plasmid, a vector, or a viral vector, such as the rAAV, described specifically herein.

In another aspect, a method for treating Leber Congenital Amaurosis caused by a defect in the lebercilin gene (LCA5) and/or restoring visual function in a mammalian subject having LCA comprises delivering via intravitreal, subretinal or intravascular injection to a subject in need thereof a recombinant AAV vector which encodes Lebercilin, as described herein.

In another aspect, use of an AAV vector as described herein is provided in treating Leber Congenital Amaurosis caused by a defect in the lebercilin gene (LCA5) and/or restoring visual function in a mammalian subject having LCA. The use includes delivering via intravitreal, subretinal or intravascular injection to a subject in need thereof a recombinant AAV vector which encodes Lebercilin, as described herein.

Other aspects and advantages of the invention will be readily apparent from the following detailed description of the invention.

BRIEF DESCRIPTION OF THE DRAWINGS

FIG. 1A shows the transgene cassettes used to generate AAV7m8.CBA.hopt.LCA5 and AAV7m8.CBA.EGFP as described herein.

FIGS. 1B-1D provide an alignment of human nucleic acid sequence of LCA5 (Native_LCA5) of SEQ ID NO: 2 and the codon optimized LCA5 (Codon-optimized_LCA5) sequence of SEQ ID NO: 3.

FIGS. 2A-2I show normalized pupillary reflex amplitudes measured at 3 months of age of AAV7m8.hopt-LCA5-injected mice compared to control (sham-injected) eyes of Lca5−/− mice treated at PN5 and PN15. Results are shown after (A) intravitreal and (B) subretinal injection or (C) in untreated (−) control mice. (D) The relative pupillary reflex amplitudes (% of baseline pupil diameter) of the right eyes of animals in each of the sub-groups shown in (A-C) plus in wildtype (C57B16) positive (+) control mice are shown graphically (E). FIGS. 2F and 2G are representations of the testing scheme used to generate the results shown in FIGS. 2A-2D. FIGS. 2H and 2I show a comparison of normalized pupillary reflex amplitudes in experimental and control mice, shown in FIGS. 2A-2D, treated at PN5 vs PN15 via subretinal (SR, I) or intravitreal (IV, H) injection. *. $p<0.1$;  $p<0.05$; *$p<0.01$.

FIGS. 3A-3F show results of water maze test AAV7m8.hopt-LCA5-injected vs. control (sham-injected) eyes of Lca5−/− mice treated at PN5 and PN15 and measured at 3 months of age as described in Example 3. FIG. 3A is a table showing the statistical analysis result. FIG. 3B is an illustration of representative results of water maze test. FIG. 3D is a bar graph showing days until first success in training of Lca5−/− mice at PN5 or PN15 treated at birth with the AAV7m8.LCA5 vector intravitreally or subretinally at birth. Wild type mice were provided as controls. FIG. 3D is a line graph of success rates under various light intensities (x-axis) of Lca5−/− mice at PN5 treated at birth with the AAV7m8.LCA5 vector intravitreally. FIG. 3E is a line graph of success rates under various light intensities (x-axis) of Lca5−/− mice at PN5 treated at birth with the AAV7m8.LCA5 vector subretinally. FIG. 3F is a line graph of success rates under various light intensities (x-axis) of Lca5−/− mice at PN15 treated at birth with the AAV7m8.LCA5 vector intravitreally.

FIGS. 6A-6E show that there is massive cell death during photoreceptor degeneration early in life in the untreated Lca5−/− retina (and delay of this degeneration after treatment with AAV.hopt.LCA5) as evidenced by (A) TUNEL assay (FIG. 6A; FIG. 6B-E, third row) and (B) rhodopsin immunfluorescence analysis. (FIG. 6B-E, rows 1, 3 and 4).

FIGS. 7A-7D show that outer segments were present in AAV7m8.hopt.LCA5-treated Lca5−/− retinas but not in control Lca5−/− retinas. Transmission electron microscopic evaluation of the retinas injected with AAV7m8.hopt.LCA5 reveals both rod and cone photoreceptor outer segments with stacked discs and connecting cilia in 3 month old Lca5−/−. No such structures were present in untreated Lca5−/− retinas. (A, B) PN80 after intravitreal injection at PN5 with AAV7m8p643 (codon optimized Lebercilin), representative pictures; (A1-A3): 12K resolution, stitched pictures showing rows of phororeceptor cells, Rod cells (arrow heads), cone cells (arrows), many mitochondria of photoreceptor cells (asterisks); (B), 20K resolution; (B1) cross section of cilia showing 9+0 structure of microtubule, membraneous disc of OS from Rod cell (arrows); (C) 30K resolution, basal body (arrow head); (C1) sagital section of connecting cilium; (D) 12K resolution, no photoreceptor cells remained in ONL; (D1) pyknotic nuclei (arrow head) of a dying cell; (D2) floating remnants of dead cell organelles including rough ER (arrows).

FIGS. 11A-11B provide a plasmid map and a feature list of the pAAV.CMV.CBA.human native Lebercilin vector. The nucleic acid sequence is reproduced in SEQ ID NO: 9.

DETAILED DESCRIPTION OF THE INVENTION

Figure 1E:
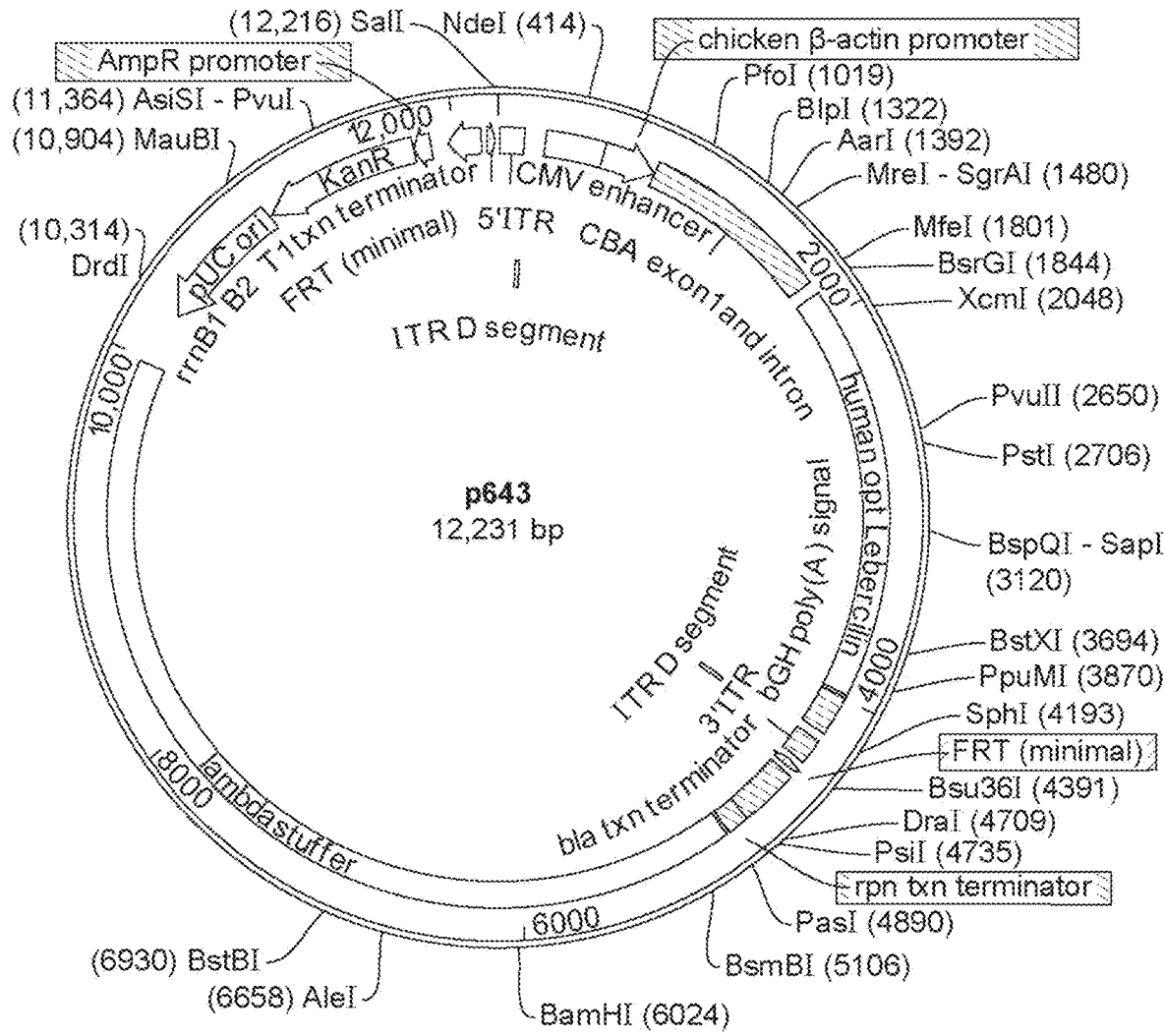
FIGS. 1E-1F provide a plasmid map and a feature list of the pAAV.CMV.CBA.human codon-optimized Lebercilin vector. The nucleic acid sequence is reproduced in SEQ ID NO: 8.

The methods and compositions described herein involve compositions and methods for delivering a LCA5 nucleic acid sequence encoding Lebercilin protein to subjects in need thereof for the treatment of Leber congenital amaurosis (LCA). In one embodiment, such compositions involve codon optimization of Lebercilin coding sequence. It is desirable to increase the efficacy of the product, and thus, increase safety, since a lower dose of reagent may be used. Also encompassed herein are compositions which include the native Lebercilin coding sequences, as shown in SEQ ID NO: 2.

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

"Lebercilin" is encoded by the LCA5 gene on chromosome 6q14 and is a ciliary protein that localizes to the connecting cilia of photoreceptors and to the microtubules, centrioles and primary cilia of cultured mammalian cells.

Lebercilin is expressed widely throughout development and is found in cilia of cultured cells as well as in the connecting cilium of mature photoreceptor cells. The connecting cilium is a narrow structure between the photoreceptor inner segment that harbors the biosynthetic machinery of the cell, and the outer segments that contain the opsin-driven visual cascade. The connecting cilium functions as a conduit, supporting the bi-directional trafficking of proteins and vesicles along ciliary microtubule tracks in a process known as intraflagellar transport (IFT). Applying quantitative affinity proteomics to a genetically engineered Lca5 mouse model, Boldt et al demonstrated that Lca5 loss of function disrupts IFT, thereby causing defects in photoreceptor outer segment development and failed arrestin and opsin trafficking. The Lca5 null (Lca5gt/gt) mice lack cone and rod ERG responses and undergo an early and progressive retinal degeneration with only a single row of dispersed nuclei (compared to 8-10 rows of contiguous cells in retinas of wildtype mice) present in the outer nuclear layer (ONL) by 2 months of age 19.

Mutations in LCA5 lead to an inherited form of retinal degeneration called Leber Congenital Amaurosis (LCA). The phenotype in affected individuals is limited to the eye and results in blindness. In 6 families studied by den Hollander, 5 had homozygous nonsense and frameshift mutations and in one family the LCA5 transcript was completely absent. The nucleic acids encoding the Lebercilin cDNA or a codon-optimized version thereof are of the appropriate size to fit into an adeno-associated virus (AAV) vector. See e.g., the sequences in FIGS. 1A and 1E to 1F and FIG. 11A-11B. As described in the examples, below, using a rAAV-mediated gene augmentation strategy, it is shown that retinal degeneration due to LCA5 mutations can be corrected. Such therapy is particularly advantageous if the wildtype or optimized copy of the gene is delivered early in life, e.g., in childhood or in early postnatal period. Further, this intravitreal or subretinal administration used in one embodiment, provides the gene efficiently to the target cells (e.g., photoreceptors).

The Lebercilin gene, LCA5, encodes Lebercilin, a 697 amino acid protein thought to be involved in centrosomal or cillary functions and minus end-directed microtubule transport. As used herein, the terms "LCA5" and "Lebercilin" are used interchangeably when referring to the coding sequence. The native nucleic acid sequences encoding human Lebercilin are reported at NCBI Reference Sequence NM_181714.3 (transcript variant 1), NM_001122769.2 (transcript variant 2), XM_011535504.1 (transcript variant X1) and XM_005248665.4 (transcript variant X2), and reproduced here in SEQ ID NO: 4, 5, 6 and 7, respectively.

The native human amino acid sequence of Lebercilin is reproduced here at SEQ ID NO: 1 (NCBI Reference Sequence: NP 001116241.1 or NP 859065.2, as well as UniProtKB/Swiss-Prot ID: Q86VQ0-1). Mutations in the LCA5 gene are associated with Leber's congenital amaurosis (LCA). In certain embodiments, the terms "LCA5" and "Lebercilin" are used interchangeably.

Leber congenital amaurosis (LCA) is an eye disorder that primarily affects the retina, which is the specialized tissue at the back of the eye that detects light and color. People with this disorder typically have severe visual impairment beginning in infancy. The visual impairment tends to be stable, although it may worsen very slowly over time. Leber congenital amaurosis is also associated with other vision problems, including an increased sensitivity to light (photophobia), involuntary movements of the eyes (nystagmus), and extreme farsightedness (hyperopia). The pupils, which usually expand and contract in response to the amount of light entering the eye, do not react normally to light. Instead, they expand and contract more slowly than normal, or they may not respond to light at all. Additionally, the clear front covering of the eye (the cornea) may be cone-shaped and abnormally thin, a condition known as keratoconus. A specific behavior called Franceschetti's oculo-digital sign is characteristic of Leber congenital amaurosis. This sign consists of poking, pressing, and rubbing the eyes with a knuckle or finger. Researchers suspect that this behavior may contribute to deep-set eyes and keratoconus in affected children. In rare cases, delayed development and intellectual disability have been reported in people with the features of Leber congenital amaurosis. However, researchers are uncertain whether these individuals actually have Leber congenital amaurosis or another syndrome with similar signs and symptoms. At least 13 types of Leber congenital amaurosis have been described. The types are distinguished by their genetic cause, patterns of vision loss, and related eye abnormalities.

The term "percent (%) identity", "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Identity may be determined by preparing an alignment of the sequences and through the use of a variety of algorithms and/or computer programs known in the art or commercially available [e.g., BLAST, ExPASy; ClustalO; FASTA; using, e.g., Needleman-Wunsch algorithm, Smith-Waterman algorithm]. Alignments are performed using any of a variety of publicly or commercially available Multiple Sequence Alignment Programs. Sequence alignment programs are available for amino acid sequences, e.g., the "Clustal Omega" "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

Multiple sequence alignment programs are also available for nucleic acid sequences. Examples of such programs include, "Clustal Omega" "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

In one aspect, a codon optimized, engineered nucleic acid sequence encoding human Lebercilin is provided. Preferably, the codon optimized Lebercilin coding sequence has less than about 80% identity, preferably about 75% identity or less to the full-length native Lebercilin coding sequence (FIGS. 1B-1D, SEQ ID NO: 2). In one embodiment, the codon optimized Lebercilin coding sequence has about 74% identity with the native Lebercilin coding sequence of SEQ ID NO: 2. In one embodiment, the codon optimized Lebercilin coding sequence is characterized by improved translation rate as compared to native Lebercilin following AAV-mediated delivery (e.g., rAAV). In one embodiment, the codon optimized Lebercilin coding sequence shares less than about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61% or less identity to the full length native Lebercilin coding sequence of SEQ ID NO: 2. In one embodiment, the codon optimized nucleic acid sequence is a variant of SEQ ID NO: 3. In another embodiment, the codon optimized nucleic acid sequence a sequence sharing about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61% or greater identity with SEQ ID NO: 3. In one embodiment, the codon optimized nucleic acid sequence is SEQ ID NO: 3. In another embodiment, the nucleic acid sequence is codon optimized for expression in humans. In another embodiment, the lebercilin coding sequence is nt 1883 to nt 3976 of SEQ ID NO: 8. In other embodiments, a different Lebercilin coding sequence is selected.

Codon-optimized coding regions can be designed by various different methods. This optimization may be performed using methods which are available on-line (e.g., GeneArt), published methods, or a company which provides codon optimizing services, e.g., DNA2.0 (Menlo Park, Calif.). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

By "engineered" is meant that the nucleic acid sequences encoding the Lebercilin protein described herein are assembled and placed into any suitable genetic element, e.g., naked DNA, phage, transposon, cosmid, episome, etc., which transfers the Lebercilin sequences carried thereon to a host cell, e.g., for generating non-viral delivery systems (e.g., RNA-based systems, naked DNA, or the like) or for generating viral vectors in a packaging host cell and/or for delivery to a host cells in a subject. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

As used herein, the term "host cell" may refer to the packaging cell line in which a recombinant AAV is produced from a production plasmid. In the alternative, the term "host cell" may refer to any target cell in which expression of the coding sequence is desired. Thus, a "host cell," refers to a prokaryotic or eukaryotic cell that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. In certain embodiments herein, the term "host cell" refers to the cells employed to generate and package the viral vector or recombinant virus. In other embodiments herein, the term "host cell" refers to cultures of ocular cells of various mammalian species for in vitro assessment of the compositions described herein. Still in other embodiments, the term "host cell" is intended to reference the ocular cells of the subject being treated in vivo for LCA.

As used herein, the term "ocular cells" refers to any cell in, or associated with the function of, the eye. The term may refer to any one of photoreceptor cells, including rod photoreceptors, cone photoreceptors and photosensitive ganglion cells, retinal pigment epithelium (RPE) cells, Mueller cells, choroidal cells, bipolar cells, horizontal cells, and amacrine cells. In one embodiment, the ocular cells are the photoreceptor cells. In another embodiment, the ocular cells are cone photoreceptors. In another embodiment, the ocular cells are rod photoreceptors.

In one embodiment, the nucleic acid sequence encoding Lebercilin further comprises a nucleic acid encoding a tag polypeptide covalently linked thereto. The tag polypeptide may be selected from known "epitope tags" including, without limitation, a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide.

In another aspect, an expression cassette comprising a nucleic acid sequence that encodes Lebercilin is provided. In one embodiment, the sequence is a codon optimized sequence. In another embodiment, the codon optimized nucleic acid sequence is SEQ ID NO: 3 encoding human Lebercilin.

As used herein, an "expression cassette" refers to a nucleic acid molecule which comprises the coding sequences for Lebercilin protein, promoter, and may include other regulatory sequences therefor, which cassette may be packaged into the capsid of a viral vector (e.g., a viral particle). Typically, such an expression cassette for generating a viral vector contains the LCA5 sequences described herein flanked by packaging signals of the viral genome and other expression control sequences such as those described herein. For example, for an AAV viral vector, the packaging signals are the 5' inverted terminal repeat (ITR) and the 3' ITR. When packaged into the AAV capsid, the ITRs in conjunction with the expression cassette may be referred to herein as the "recombinant AAV (rAAV) genome" or "vector genome". In one embodiment, an expression cassette comprises a codon optimized nucleic acid sequence that encodes Lebercilin protein. In one embodiment, the cassette provides the codon optimized LCA5 operatively associated with expression control sequences that direct expression of the codon optimized nucleic acid sequence that encodes Lebercilin in a host cell. In one embodiment, the vector genome is the sequence of nt 1-4379 of SEQ ID NO: 8. In another embodiment, the vector genome is the sequence of nt 1-4368 of SEQ ID NO: 9. In yet another embodiment, the LCA5 coding sequence in either of the identified vector genomes is swapped with another LCA5 coding sequence as described herein.

In another embodiment, an expression cassette for use in an AAV vector is provided. In that embodiment, the AAV expression cassette includes at least one AAV inverted terminal repeat (ITR) sequence. In another embodiment, the expression cassette comprises 5' ITR sequences and 3' ITR sequences. In one embodiment, the 5' and 3' ITRs flank the codon optimized nucleic acid sequence that encodes Lebercilin, optionally with additional sequences which direct expression of the codon optimized nucleic acid sequence that encodes Lebercilin in a host cell. Thus, as described herein, a AAV expression cassette is meant to describe an expression cassette as described above flanked on its 5' end by a 5'AAV inverted terminal repeat sequence (ITR) and on its 3' end by a 3' AAV ITR. Thus, this rAAV genome contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, the AAV vector genome comprises an AAV 5' ITR, the Lebercilin coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. Each rAAV genome can be then introduced into a production plasmid.

As used herein, the term "regulatory sequences", "transcriptional control sequence" or "expression control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "operably linked" or "operatively associated" refers to both expression control sequences that are contiguous with the nucleic acid sequence encoding the Lebercilin and/or expression control sequences that act in trans or at a distance to control the transcription and expression thereof.

In one aspect, a vector comprising any of the expression cassettes described herein is provided. As described herein, such vectors can be plasmids of variety of origins and are useful in certain embodiments for the generation of recombinant replication defective viruses as described further herein.

A "vector" as used herein is a nucleic acid molecule into which an exogenous or heterologous or engineered nucleic acid transgene may be inserted which can then be introduced into an appropriate host cell. Vectors preferably have one or more origin of replication, and one or more site into which the recombinant DNA can be inserted. Vectors often have means by which cells with vectors can be selected from those without, e.g., they encode drug resistance genes. Common vectors include plasmids, viral genomes, and (primarily in yeast and bacteria) "artificial chromosomes." Certain plasmids are described herein.

In one embodiment, the vector is a non-viral plasmid that comprises an expression cassette described thereof, e.g., "naked DNA", "naked plasmid DNA", RNA, and mRNA; coupled with various compositions and nano particles, including, e.g., micelles, liposomes, cationic lipid—nucleic acid compositions, poly-glycan compositions and other polymers, lipid and/or cholesterol-based—nucleic acid conjugates, and other constructs such as are described herein. See, e.g., X. Su et al, Mol. Pharmaceutics, 2011, 8 (3), pp 774-787; web publication: Mar. 21, 2011; WO2013/182683, WO 2010/053572 and WO 2012/170930, all of which are incorporated herein by reference. Such non-viral Lebercilin vector may be administered by the routes described herein. The viral vectors, or non-viral vectors, can be formulated with a physiologically acceptable carrier for use in gene transfer and gene therapy applications.

In another embodiment, the vector is a viral vector that comprises an expression cassette described therein. "Virus vectors" are defined as replication defective viruses containing the exogenous or heterologous LCA5 nucleic acid transgene. In one embodiment, an expression cassette as described herein may be engineered onto a plasmid which is used for drug delivery or for production of a viral vector. Suitable viral vectors are preferably replication defective and selected from amongst those which target ocular cells. Viral vectors may include any virus suitable for gene therapy, including but not limited to adenovirus; herpes virus; lentivirus; retrovirus; parvovirus; etc. However, for ease of understanding, the adeno-associated virus is referenced herein as an exemplary virus vector.

A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In another embodiment, a recombinant adeno-associated virus (rAAV) vector is provided. The rAAV compromises an AAV capsid, and a vector genome packaged therein.

The vector genome comprises, in one embodiment: (a) an AAV 5' inverted terminal repeat (ITR) sequence; (b) a promoter; (c) a coding sequence encoding a human Lebercilin; and (d) an AAV 3' ITR. In another embodiment, the vector genome is the expression cassette described herein. In one embodiment, the LCA5 sequence encodes a full length Lebercilin protein. In one embodiment, the Lebercilin sequence is the protein sequence of SEQ ID NO: 1. In another embodiment, the coding sequence is SEQ ID NO: 3 or a variant thereof.

Adeno-associated virus (AAV), a member of the Parvovirus family, is a small nonenveloped, icosahedral virus with single-stranded linear DNA genomes of 4.7 kilobases (kb) to 6 kb. Among known AAV serotypes are AAV1, AAV2, AAV3, AAV4, AAV5, AAV6, AAV7, AAV8, AAV9 and others. The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, Va.). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

Fragments of AAV may be readily utilized in a variety of vector systems and host cells. Among desirable AAV fragments are the cap proteins, including the vp1, vp2, vp3 and hypervariable regions, the rep proteins, including rep 78, rep 68, rep 52, and rep 40, and the sequences encoding these proteins. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. In one embodiment, a vector contains the AAV8 cap and/or rep sequences of the invention. See e.g., US patent application publication No. US2009/02270030, incorporated by reference herein.

The term "AAV" or "AAV serotype" as used herein refers to the dozens of naturally occurring and available adeno-associated viruses, as well as artificial AAVs. Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, AAV1, AAV2, AAV3, AAV4, AAV5, AAV6, AAV7, AAV8, AAV9, AAV8 bp, AAV7M8 and AAVAnc80, variants of any of the known or mentioned AAVs or AAVs yet to be discovered or variants or mixtures thereof. See, e.g., WO 2005/033321, which is incorporated herein by reference. In another embodiment, the AAV capsid is an AAV8 bp capsid, which preferentially targets bipolar cells. See, WO 2014/024282, which is incorporated herein by reference. In another embodiment, the AAV capsid is an AAV7m8 capsid, which has shown preferential delivery to the outer retina. The AAV7m8 capsid nucleic acid sequence is reproduced in SEQ ID NO: 11 and amino acid sequence at SEQ ID NO: 12. See, Dalkara et al, In Vivo—Directed Evolution of a New Adeno-Associated Virus for Therapeutic Outer Retinal Gene Delivery from the Vitreous, Sci Transl Med 5, 189ra76 (2013), which is incorporated herein by reference.

As used herein, an "AAV7m8 capsid" is a self-assembled AAV capsid composed of multiple AAV7m8 vp (variable protein) proteins. The AAV7m8 vp proteins are typically expressed as alternative splice variants encoded by a nucleic acid sequence of SEQ ID NO: 11 or a sequence at least 70%, at least 75%, at least 80%, at least 85%, at least 90%, at least 95%, at least 97%, at least 99% thereto, which encodes the vp1 amino acid sequence of SEQ ID NO: 12. These splice variants result in proteins of different length of SEQ ID NO: 12. In certain embodiments, "AAV7m8 capsid" includes an AAV having an amino acid sequence which is 99% identical to SEQ ID NO: 12.

In another embodiment, the rAAV capsid is selected from an AAV8 capsid or variant thereof, an AAV6 capsid or variant thereof, an AAV9 capsid or variant thereof, an AAV7 capsid or variant thereof, an AAV5 capsid or variant thereof, an AAV2 capsid or variant thereof, an AAV1 capsid or variant thereof, an AAV3 capsid or variant thereof, and an AAV4 capsid or variant thereof. In one embodiment, a recombinant adeno-associated virus (rAAV) vector is provided which comprises an AAV7m8 capsid and an expression cassette described herein, wherein said expression cassette comprises nucleic acid sequences encoding Lebercilin, inverted terminal repeat sequences and expression control sequences that direct expression of Lebercilin in a host cell.

In still a further embodiment, a recombinant adeno-associated virus (AAV) vector is provided for delivery of the LCA5 constructs and optimized sequences described herein. An adeno-associated virus (AAV) viral vector is an AAV DNase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10) and (Dalkara D, Byrne L C, Klimczak R R, Visel M, Yin L, Merigan W H, et al. In vivo-directed evolution of a new adeno-associated virus for therapeutic outer retinal gene delivery from the vitreous. Sci Transl Med (2013) 5(189):189ra76. doi: 10.1126/scitranslmed.3005708.) (AAV7m8). Each of these documents is incorporated herein by reference. These documents also describe other AAV capsids which may be selected for generating AAV and are incorporated by reference. In some embodiments, an AAV cap for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

As used herein, relating to AAV, the term variant means any AAV sequence which is derived from a known AAV sequence, including those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV7m8 over the vp1, vp2 or vp3. In another embodiment, the capsid is an AAV8 capsid with Y447F, Y733F and T494V mutations (also called "AAV8(C&G+T494V)" and "rep2-cap8(Y447F+733F+T494V)"), as described by Kay et al, Targeting Photoreceptors via Intravitreal Delivery Using Novel, Capsid-Mutated AAV Vectors, PLoS One. 2013; 8(4): e62097. Published online 2013 Apr. 26, which is incorporated herein by reference.

In one embodiment, it is desirable to utilize an AAV capsid, which shows tropism for the desired target cell, e.g., photoreceptors (e.g., rods and/or cones), RPE or other ocular cells. In one embodiment, the AAV capsid is a tyrosine capsid-mutant in which certain surface exposed tyrosine residues are substituted with phenylalanine (F). Such AAV variants are described, e.g., in Mowat et al, Tyrosine capsid-mutant AAV vectors for gene delivery to the canine retina from a subretinal or intravitreal approach, Gene Therapy 21, 96-105 (January 2014), which is incorporated herein by reference.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors.

In another embodiment, a self-complementary AAV is used. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

The term "exogenous" as used herein to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

In still another embodiment, the expression cassette, including any of those described herein is employed to generate a recombinant AAV genome.

In one embodiment, the expression cassette described herein is engineered into a suitable genetic element (vector) useful for generating viral vectors and/or for delivery to a host cell, e.g., naked DNA, phage, transposon, cosmid, episome, etc., which transfers the LCA5 sequences carried thereon. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

For packaging an expression cassette or rAAV genome or production plasmid into virions, the ITRs are the only AAV components required in cis in the same construct as the expression cassette. In one embodiment, the coding sequences for the replication (rep) and/or capsid (cap) are removed from the AAV genome and supplied in trans or by a packaging cell line in order to generate the AAV vector.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

In yet another system, the expression cassette flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

"Plasmids" generally are designated herein by a lower case p preceded and/or followed by capital letters and/or numbers, in accordance with standard naming conventions that are familiar to those of skill in the art. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

In one embodiment, the production plasmid is that described herein, or as described in WO2012/158757, which is incorporated herein by reference. Various plasmids are known in the art for use in producing rAAV vectors, and are useful herein. The production plasmids are cultured in the host cells which express the AAV cap and/or rep proteins. In the host cells, each rAAV genome is rescued and packaged into the capsid protein or envelope protein to form an infectious viral particle.

In one aspect, a production plasmid comprising an expression cassette described above is provided. In one embodiment, the production plasmid is that shown in SEQ ID NO: 8, and FIG. 1E-1F, which is termed p643. This plasmid is used in the examples for generation of the rAAV-human codon optimized Lebercilin vector. Such a plasmid is one that contains a 5' AAV ITR sequence; a selected promoter; a polyA sequence; and a 3' ITR; additionally, it also contains a stuffer sequence, such as lambda. In a further embodiment, the stuffer sequence keeps the rAAV vector genome with a size between about 3 kilobases (kb) to about 6 kb, about 4.7 kb to about 6 kb, about 3 kb to about 5.5 kb, or about 4.7 kb to 5.5 kb. In one embodiment, a non-coding lambda stuffer region is included in the vector backbone. An example of p643 which includes the Lebercilin encoding sequence can be found in SEQ ID NO: 8. In another embodiment, the production plasmid is that shown in FIG. 11A-11B and SEQ ID NO: 9. In another embodiment, the production plasmid is modified to optimized vector plasmid production efficiency. Such modifications include addition of other neutral sequences, or deletion of portion(s) of or the entire lambda stuffer sequence to modulate the level of supercoil of the vector plasmid. Such modifications are contemplated herein. In other embodiments, terminator and other sequences are included in the plasmid.

In certain embodiments, the rAAV expression cassette, the vector (such as rAAV vector), the virus (such as rAAV), the production plasmid comprises AAV inverted terminal repeat sequences, a codon optimized nucleic acid sequence that encodes Lebercilin, and expression control sequences that direct expression of the encoded proteins in a host cell. In other embodiments, the rAAV expression cassette, the virus, the vector (such as rAAV vector), the production plasmid further comprise one or more of an intron, a Kozak sequence, a polyA, posttranscriptional regulatory elements and others. In one embodiment, the posttranscriptional regulatory element is Woodchuck Hepatitis Virus (WHP) Posttranscriptional Regulatory Element (WPRE).

The expression cassettes, vectors and plasmids include other components that can be optimized for a specific species using techniques known in the art including, e.g, codon optimization, as described herein. The components of the cassettes, vectors, plasmids and viruses or other compositions described herein include a promoter sequence as part of the expression control sequences. In another embodiment, the promoter is cell-specific. The term "cell-specific" means that the particular promoter selected for the recombinant vector can direct expression of the optimized Lebercilin coding sequence in a particular ocular cell type. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones. In one embodiment, the photoreceptor-specific promoter is a human rhodopsin kinase promoter. The rhodopsin kinase promoter has been shown to be active in both rods and cones. See, e.g., Sun et al, Gene Therapy with a Promoter Targeting Both Rods and Cones Rescues Retinal Degeneration Caused by AIPL1 Mutations, Gene Ther. 2010 January; 17(1): 117-131, which is incorporated herein by reference in its entirety. In one embodiment, the promoter is modified to add one or more restriction sites to facilitate cloning.

In another embodiment, the promoter is a human rhodopsin promoter. In one embodiment, the promoter is modified to include restriction on the ends for cloning. See, e.g, Nathans and Hogness, Isolation and nucleotide sequence of the gene encoding human rhodopsin, PNAS, 81:4851-5 (August 1984), which is incorporated herein by reference in its entirety. In another embodiment, the promoter is a portion or fragment of the human rhodopsin promoter. In another embodiment, the promoter is a variant of the human rhodopsin promoter.

Other exemplary promoters include the human G-protein-coupled receptor protein kinase 1 (GRK1) promoter (Genbank Accession number AY327580). In another embodiment, the promoter is a 292 nt fragment (positions 1793-2087) of the GRK1 promoter (See, Beltran et al, Gene Therapy 2010 17:1162-74, which is hereby incorporated by reference in its entirety). In another preferred embodiment, the promoter is the human interphotoreceptor retinoid-binding protein proximal (IRBP) promoter. In one embodiment, the promoter is a 235 nt fragment of the hIRBP promoter. In one embodiment, the promoter is the RPGR proximal promoter (Shu et al, IOVS, May 2102, which is incorporated by reference in its entirety). Other promoters useful in the invention include, without limitation, the rod opsin promoter, the red-green opsin promoter, the blue opsin promoter, the cGMP-β-phosphodiesterase promoter (Qgueta et al, IOVS, Invest Ophthalmol Vis Sci. 2000 December; 41(13):4059-63), the mouse opsin promoter (Beltran et al2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PLoS One, October 2010, 5(10): e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Each of these documents is incorporated by reference herein in its entirety. In another embodiment, the promoter is selected from human human EFla promoter, rhodopsin promoter, rhodopsin kinase, interphotoreceptor binding protein (IRBP), cone opsin promoters (red-green, blue), cone opsin upstream sequences containing the red-green cone locus control region, cone transducing, and transcription factor promoters (neural retina leucine zipper (Nr1) and photoreceptor-specific nuclear receptor Nr2e3, bZIP).

In another embodiment, the promoter is a ubiquitous or constitutive promoter. An example of a suitable promoter is a hybrid chicken β-actin (CBA) promoter with cytomegalovirus (CMV) enhancer elements, such as the sequence shown in FIG. 1E-1F. In another embodiment, the promoter is the CB7 promoter. Other suitable promoters include the human β-actin promoter, the human elongation factor-1α promoter, the cytomegalovirus (CMV) promoter, the simian virus 40 promoter, and the herpes simplex virus thymidine kinase promoter. See, e.g., Damdindorj et al, (August 2014) A Comparative Analysis of Constitutive Promoters Located in Adeno-Associated Viral Vectors. PLoS ONE 9(8): e106472. Still other suitable promoters include viral promoters, constitutive promoters, regulatable promoters [see, e.g., WO 2011/126808 and WO 2013/04943]. Alternatively a promoter responsive to physiologic cues may be utilized in the expression cassette, rAAV genomes, vectors, plasmids and viruses described herein. In one embodiment, the promoter is of a small size, under 1000 bp, due to the size limitations of the AAV vector. In another embodiment, the promoter is under 400 bp. Other promoters may be selected by one of skill in the art.

In a further embodiment, the promoter is selected from SV40 promoter, the dihydrofolate reductase promoter, and the phosphoglycerol kinase (PGK) promoter, rhodopsin kinase promoter, the rod opsin promoter, the red-green opsin promoter, the blue opsin promoter, the inter photoreceptor binding protein (IRBP) promoter and the cGMP-β-phosphodiesterase promoter, a phage lambda (PL) promoter, a herpes simplex viral (HSV) promoter, a tetracycline-controlled trans-activator-responsive promoter (tet) system, a long terminal repeat (LTR) promoter, such as a RSV LTR, MoMLV LTR, BIV LTR or an HIV LTR, a U3 region promoter of Moloney murine sarcoma virus, a Granzyme A promoter, a regulatory sequence(s) of the metallothionein gene, a CD34 promoter, a CD8 promoter, a thymidine kinase (TK) promoter, a B19 parvovirus promoter, a PGK promoter, a glucocorticoid promoter, a heat shock protein (HSP) promoter, such as HSP65 and HSP70 promoters, an immunoglobulin promoter, an MMTV promoter, a Rous sarcoma virus (RSV) promoter, a lac promoter, a CaMV 35S promoter, a nopaline synthetase promoter, an MND promoter, or an MNC promoter. The promoter sequences thereof are known to one of skill in the art or available publically, such as in the literature or in databases, e.g., GenBank, PubMed, or the like.

In another embodiment, the promoter is an inducible promoter. The inducible promoter may be selected from known promoters including the rapamycin/rapalog promoter, the ecdysone promoter, the estrogen-responsive promoter, and the tetracycline-responsive promoter, or heterodimeric repressor switch. See, Sochor et al, An Autogenously Regulated Expression System for Gene Therapeutic Ocular Applications. Scientific Reports, 2015 Nov. 24; 5:17105 and Daber R, Lewis M., A novel molecular switch. J Mol Biol. 2009 Aug. 28; 391(4):661-70, Epub 2009 Jun. 21 which are both incorporated herein by reference in their entirety.

In a further embodiment, the promoter is a chicken beta-actin promoter with a nucleic acid sequence from nt 546 to nt 283 of SEQ ID NO. 8.

In other embodiments, the expression cassette, vector, plasmid and virus described herein contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein.

Examples of suitable polyA sequences include, e.g., a synthetic polyA or from bovine growth hormone (bGH), human growth hormone (hGH), SV40, rabbit β-globin (RGB), or modified RGB (mRGB). In a further embodiment, the poly A has a nucleic acid sequence from nt 3993 to nt 4200 of SEQ ID NO:8.

Examples of suitable enhancers include, e.g., the CMV enhancer, the RSV enhancer, the alpha fetoprotein enhancer, the TTR minimal promoter/enhancer, LSP (TH-binding globulin promoter/alphal-microglobulin/bikunin enhancer), an APB enhancer, ABPS enhancer, an alpha mic/bik enhancer, TTR enhancer, en34, ApoE amongst others. In one embodiment, the enhancer has a nucleic acid sequence from nt 241 to nt 544 of SEQ ID NO: 8.

In one embodiment, a Kozak sequence is included upstream of the Lebercilin coding sequence to enhance translation from the correct initiation codon. In another embodiment, CBA exon 1 and intron are included in the expression cassette. In one embodiment, the Lebercilin coding sequence is placed under the control of a hybrid chicken β actin (CBA) promoter. This promoter consists of the cytomegalovirus (CMV) immediate early enhancer, the proximal chicken β actin promoter, and CBA exon 1 flanked by intron 1 sequences.

In another embodiment, the intron is selected from CBA, human beta globin, IVS2, SV40, bGH, alpha-globulin, beta-globulin, collagen, ovalbumin, p53, or a fragment thereof.

In one embodiment, the expression cassette, the vector, the plasmid and the virus contain a 5' ITR, chicken beta-actin (CBA) promoter, CMV enhancer, CBA exon 1 and intron, human codon optimized Lebercilin sequence, bGH poly A and 3' ITR. In a further embodiment, the expression cassette includes nt 1 to 4379 of SEQ ID NO: 8. In yet a further embodiment, the 5' ITR has a nucleic acid sequence from nt 1 to nt 130 of SEQ ID NO: 8 and the 3'ITR has a nucleic acid sequence from nt 4250 to nt 4379 of SEQ ID NO: 8. In a further embodiment, the CBA exon1 and intron has a nucleic acid sequence from nt 824 to nt 1795 of SEQ ID NO:8. In a further embodiment, the production plasmid has a sequence of SEQ ID NO: 8, also shown in FIGS. 1E-1F. In a further embodiment, the production plasmid has a sequence of SEQ ID NO: 9, also shown in FIGS. 1A-11B.

In another aspect, a method for treating Leber Congenital Amaurosis caused by a defect in the lebercilin gene and/or restoring visual function in a subject having LCA comprises delivering to a subject in need thereof a vector (such as rAAV) which encodes Lebercilin, as described herein. In one embodiment, a method of treating a subject having LCA with a rAAV described herein is provided.

By "administering" as used in the methods means delivering the composition to the target selected cell which is characterized by LCA. In one embodiment, the method involves delivering the composition by subretinal injection to the RPE, photoreceptor cells or other ocular cells. In another embodiment, intravitreal injection to the subject is employed. In another embodiment, subretinal injection to the subject is employed. In still another method, intravascular injections, such as injection via the palpebral vein may be employed. Still other methods of administration may be selected by one of skill in the art given this disclosure.

By "administering" or "route of administration" is delivery of composition described herein, with or without a pharmaceutical carrier or excipient, of the subject. Routes of administration may be combined, if desired. In some embodiments, the administration is repeated periodically. The pharmaceutical compositions described herein are designed for delivery to subjects in need thereof by any suitable route or a combination of different routes. In some embodiments, direct delivery to the eye (optionally via ocular delivery, subretinal injection, intra-retinal injection, intravitreal, topical), or delivery via systemic routes is employed, e.g., intravascular, intraarterial, intraocular, intravenous, intramuscular, subcutaneous, intradermal, and other parental routes of administration. The nucleic acid molecules, the expression cassette and/or vectors described herein may be delivered in a single composition or multiple compositions. Optionally, two or more different AAV may be delivered, or multiple viruses [see, e.g., WO20 2011/126808 and WO 2013/049493]. In another embodiment, multiple viruses may contain different replication-defective viruses (e.g., AAV and adenovirus), alone or in combination with proteins.

Also provided herein are pharmaceutical compositions. The pharmaceutical compositions described herein are designed for delivery to subjects in need thereof by any suitable route or a combination of different routes. These delivery means are designed to avoid direct systemic delivery of the suspension containing the AAV composition(s) described herein. Suitably, this may have the benefit of reducing dose as compared to systemic administration, reducing toxicity and/or reducing undesirable immune responses to the AAV and/or transgene product.

In yet other aspects, these nucleic acid sequences, vectors, expression cassettes and rAAV viral vectors are useful in a pharmaceutical composition, which also comprises a pharmaceutically acceptable carrier, excipient, buffer, diluent, surfactant, preservative and/or adjuvant, etc. Such pharmaceutical compositions are used to express the optimized Lebercilin in the host cells through delivery by such recombinantly engineered AAVs or artificial AAVs.

To prepare these pharmaceutical compositions containing the nucleic acid sequences, vectors, expression cassettes and rAAV viral vectors, the sequences or vectors or viral vector is preferably assessed for contamination by conventional methods and then formulated into a pharmaceutical composition suitable for administration to the eye. Such formulation involves the use of a pharmaceutically and/or physiologically acceptable vehicle or carrier, particularly one suitable for administration to the eye, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, surfactant, or excipient etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravitreal or subretinal delivery, a pH of 6.8 to about 7.2 may be desired. However, other pHs within the broadest ranges and these subranges may be selected for other route of delivery.

A suitable surfactant, or combination of surfactants, may be selected from among nonionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate.7H2O), potassium chloride, calcium chloride (e.g., calcium chloride.2H2O), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/article/2093316-overview. Optionally, for intrathecal delivery, a commercially available diluent may be used as a suspending agent, or in combination with another suspending agent and other optional excipients. See, e.g., Elliotts B® solution [Lukare Medical]. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intravitreal delivery. In one example, the composition is formulated for subretinal delivery.

In one exemplary specific embodiment, the composition of the carrier or excipient contains 180 mM NaCl, 10 mM NaPi, pH7.3 with 0.0001%-0.01% Pluronic F68 (PF68). The exact composition of the saline component of the buffer ranges from 160 mM to 180 mM NaCl. Optionally, a different pH buffer (potentially HEPES, sodium bicarbonate, TRIS) is used in place of the buffer specifically described. Still alternatively, a buffer containing 0.9% NaCl is useful.

In the case of AAV viral vectors, quantification of the genome copies ("GC"), vector genomes ("VG"), or virus particles may be used as the measure of the dose contained in the formulation or suspension. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal). In another method the effective dose of a recombinant adeno-associated virus carrying a nucleic acid sequence encoding the optimized Lebercilin coding sequence is measured as described in S. K. McLaughlin et al, 1988 J. Virol., 62:1963, which is incorporated by reference in its entirety.

As used herein, the term "dosage" can refer to the total dosage delivered to the subject in the course of treatment, or the amount delivered in a single unit (or multiple unit or split dosage) administration. The pharmaceutical virus compositions can be formulated in dosage units to contain an amount of replication-defective virus carrying the codon optimized nucleic acid sequences encoding Lebercilin as described herein that is in the range of about $1.0 \times 10^9$ GC to about $1.0 \times 10^{15}$ GC per dose including all integers or fractional amounts within the range. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range. All dosages may be measured by any known method, including as measured by oqPCR or digital droplet PCR (ddPCR) as described in, e.g., M. Lock et al, Hum Gene Ther Methods. 2014 April; 25(2):115-25. doi: 10.1089/hgtb.2013.131, which is incorporated herein by reference.

In one embodiment, an aqueous suspension suitable for administration to an LCA patient is provided. The suspension comprises an aqueous suspending liquid and about $1\times10^{10}$ GC or viral particles to about $1\times10^{12}$ GC or viral particles per eye of a recombinant adeno-associated virus (rAAV) described herein useful as a therapeutic for LCA.

It may also be desirable to administer multiple "booster" dosages of the pharmaceutical compositions of this invention. For example, depending upon the duration of the transgene within the ocular target cell, one may deliver booster dosages at 6 month intervals, or yearly following the first administration. The fact that AAV-neutralizing antibodies were not generated by administration of the rAAV vector should allow additional booster administrations.

Such booster dosages and the need therefor can be monitored by the attending physicians, using, for example, the retinal and visual function tests and the visual behavior tests described in the examples below. Other similar tests may be used to determine the status of the treated subject over time. Selection of the appropriate tests may be made by the attending physician. Still alternatively, the method of this invention may also involve injection of a larger volume of virus-containing solution in a single or multiple infection to allow levels of visual function close to those found in wildtype retinas.

In another embodiment, the amount of the vectors, the virus and the replication-defective virus described herein carrying the codon optimized nucleic acid sequences encoding Lebercilin are in the range of about $1.0\times10^7$ VG per eye to about $1.0\times10^{15}$ VG per eye including all integers or fractional amounts within the range. In one embodiment, the amount thereof is at least $1\times10^7$, $2\times10^7$, $3\times10^7$, $4\times10^7$, $5\times10^7$, $6\times10^7$, $7\times10^7$, $8\times10^7$, or $9\times10^7$ VG per eye including all integers or fractional amounts within the range. In one embodiment, the amount thereof is at least $1\times10^8$, $2\times10^8$, $3\times10^8$, $4\times10^8$, $5\times10^8$, $6\times10^8$, $7\times10^8$, $8\times10^8$, or $9\times10^8$ VG per eye including all integers or fractional amounts within the range. In one embodiment, the amount thereof is at least $1\times10^9$, $2\times10^9$, $3\times10^9$, $4\times10^9$, $5\times10^9$, $6\times10^9$, $7\times10^9$, $8\times10^9$, or $9\times10^9$ VG per eye including all integers or fractional amounts within the range. In one embodiment, the amount thereof is at least $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ VG per eye including all integers or fractional amounts within the range. In one embodiment, the amount thereof is at least $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ VG per eye including all integers or fractional amounts within the range. In one embodiment, the amount thereof is at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ VG per eye including all integers or fractional amounts within the range. In one embodiment, the amount thereof is at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ VG per eye including all integers or fractional amounts within the range. In one embodiment, the amount thereof is at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ VG per eye including all integers or fractional amounts within the range. In one embodiment, the amount thereof is at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range. In one embodiment, the methods comprises dose ranging from $1\times10^9$ to about $1\times10^{13}$ VG per eye per dose including all integers or fractional amounts within the range. In another embodiment, the method comprises delivery of the vector in an aqueous suspension. In another embodiment, the method comprises administering the rAAV described herein in a dosage of from $1\times10^9$ to $1\times10^{13}$ GC in a volume about or at least 150 microliters, thereby restoring visual function in said subject. All dosages may be measured by any known method, including as measured by oqPCR or digital droplet PCR (ddPCR) as described in, e.g., M. Lock et al, Hum Gene Ther Methods. 2014 April; 25(2):115-25. doi: 10.1089/hgtb.2013.131, which is incorporated herein by reference.

These above doses may be administered in a variety of volumes of carrier, excipient or buffer formulation, ranging from about 25 to about 1000 microliters, including all numbers within the range, depending on the size of the area to be treated, the viral titer used, the route of administration, and the desired effect of the method. In one embodiment, the volume of carrier, excipient or buffer is at least about 25 µL. In one embodiment, the volume is about 50 µL. In another embodiment, the volume is about 75 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 225 µL. In yet another embodiment, the volume is about 250 µL. In yet another embodiment, the volume is about 275 µL. In yet another embodiment, the volume is about 300 µL. In yet another embodiment, the volume is about 325 µL. In another embodiment, the volume is about 350 µL. In another embodiment, the volume is about 375 µL. In another embodiment, the volume is about 400 µL. In another embodiment, the volume is about 450 µL. In another embodiment, the volume is about 500 µL. In another embodiment, the volume is about 550 µL. In another embodiment, the volume is about 600 µL. In another embodiment, the volume is about 650 µL. In another embodiment, the volume is about 700 µL. In another embodiment, the volume is about 800 µL. In another embodiment, the volume is between about 150 and 800 µL. In another embodiment, the volume is between about 700 and 1000 µL. In another embodiment, the volume is between about 250 and 500 µL.

In one embodiment, the viral constructs may be delivered in doses of from at least $1\times10^9$ to about least $1\times10^{11}$ GCs in volumes of about 1 µL to about 3 µL for small animal subjects, such as mice. For larger veterinary subjects having eyes about the same size as human eyes, the larger human dosages and volumes stated above are useful. See, e.g., Diehl et al, J. Applied Toxicology, 21:15-23 (2001) for a discussion of good practices for administration of substances to various veterinary animals. This document is incorporated herein by reference.

It is desirable that the lowest effective concentration of virus or other delivery vehicle be utilized in order to reduce the risk of undesirable effects, such as toxicity, retinal dysplasia and detachment. Still other dosages in these ranges may be selected by the attending physician, taking into account the physical state of the subject, preferably human, being treated, the age of the subject, the LCA and the degree to which the disorder, if progressive, has developed.

Yet another aspect described herein is a method for treating, retarding or halting progression of LCA in a mammalian subject. In one embodiment, an rAAV carrying the Lebercilin native, modified or codon optimized sequence, preferably suspended in a physiologically compatible carrier, diluent, excipient and/or adjuvant, may be administered to a desired subject including a human subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of LCA, and may also involve administration via the palpebral vein or other intravenous or conventional administration routes.

For use in these methods, the volume and viral titer of each dosage is determined individually, as further described herein, and may be the same or different from other treatments performed in the same, or contralateral, eye. The dosages, administrations and regimens may be determined by the attending physician given the teachings of this specification. In one embodiment, the composition is administered in a single dosage selected from those above listed in an affected eye. In another embodiment, the composition is administered as a single dosage selected from those above listed in a both affected eyes, either simultaneously or sequentially. Sequential administration may imply a time gap of administration from one eye to another from intervals of minutes, hours, days, weeks or months. In another embodiment, the method involves administering the compositions to an eye two or more dosages (e.g., split dosages). In another embodiment, multiple injections are made in different portions of the same eye. In another embodiment, a second administration of an rAAV including the selected expression cassette (e.g., LCA5 containing cassette) is performed at a later time point. Such time point may be weeks, months or years following the first administration. Such second administration is, in one embodiment, performed with an rAAV having a different capsid than the rAAV from the first administration. In another embodiment, the rAAV from the first and second administration have the same capsid.

In still other embodiments, the compositions described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

In certain embodiments of the invention, it is desirable to perform non-invasive retinal imaging and functional studies to identify areas of the rod and cone photoreceptors to be targeted for therapy as well as to test the efficacy of treatment. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, Multi-electrode array (MEA), Pupillary Light Responses, etc, depending upon the species of the subject being treated, their physical status and health and the dosage. In view of the imaging and functional studies, in some embodiments of the invention one or more injections are performed in the same eye in order to target different areas of the affected eye. The volume and viral titer of each injection is determined individually, as further described herein, and may be the same or different from other injections performed in the same, or contralateral, eye.

In another embodiment, a single, larger volume injection is made in order to treat the entire eye. In one embodiment, the volume and concentration of the rAAV composition is selected so that only the region of damaged ocular cells is impacted. In another embodiment, the volume and/or concentration of the rAAV composition is a greater amount, in order reach larger portions of the eye, including non-damaged photoreceptors.

In another embodiment, the method includes performing additional studies, e.g., functional and imaging studies to determine the efficacy of the treatment. For examination in animals, such tests include retinal and visual function assessment via electroretinograms (ERGs) looking at rod and cone photoreceptor function, optokinetic nystagmus, pupillometry, water maze testing, light-dark preference, optical coherence tomography (to measure thickness of various layers of the retina), histology (retinal thickness, rows of nuclei in the outer nuclear layer, immunofluorescence to document transgene expression, cone photoreceptor counting, staining of retinal sections with peanut agglutinin—which identifies cone photoreceptor sheaths).

Specifically for human subjects, following administration of a dosage of a compositions described in this specification, the subject is tested for efficacy of treatment using electroretinograms (ERGs) to examine rod and cone photoreceptor function, pupillometry visual acuity, contrast sensitivity color vision testing, visual field testing (Humphrey visual fields/Goldmann visual fields), perimetry mobility test (obstacle course), and reading speed test. Other useful post-treatment efficacy test to which the subject is exposed following treatment with a pharmaceutical composition described herein are functional magnetic resonance imaging (fMRI), full-field light sensitivity testing, retinal structure studies including optical coherence tomography, fundus photography, fundus autofluorescence, adaptive optics laser scanning ophthalmoscopy, mobility testing, test of reading speed and accuracy, microperimetry and/or ophthalmoscopy. These and other efficacy tests are described in U.S. Pat. No. 8,147,823; in co-pending International patent application publication WO 2014/011210 or WO 2014/124282, incorporated by reference.

In one embodiment of the methods described herein, a one-time intra-ocular delivery of a composition as described herein, e.g., an AAV delivery of an optimized LCA5 cassette, is useful in treating LCA in a subject. In another embodiment of the methods described herein, a one-time intra-ocular delivery of a composition as described herein, e.g., an AAV delivery of an optimized LCA5 cassette, is useful in treating LCA in a subject at risk.

Thus, in one embodiment, the composition is administered before disease onset. In another embodiment, the composition is administered prior to the initiation of vision impairment or loss. In another embodiment, the composition is administered after initiation of vision impairment or loss. In yet another embodiment, the composition is administered when less than 90% of the rod and/or cones or photoreceptors are functioning or remaining, as compared to a non-diseased eye. In one embodiment, neonatal treatment is defined as being administered a Lebercilin coding sequence, expression cassette or vector as described herein within 8 hours, the first 12 hours, the first 24 hours, or the first 48 hours of delivery. In another embodiment, particularly for a primate (human or non-human), neonatal delivery is within the period of about 12 hours to about 1 week, 2 weeks, 3 weeks, or about 1 month, or after about 24 hours to about 48 hours. In another embodiment, the composition is delivered after onset of symptoms. In one embodiment, treatment of the patient (e.g., a first injection) is initiated prior to the first year of life. In another embodiment, treatment is initiated after the first 1 year, or after the first 2 to 3 years of age, after 5 years of age, after 11 years of age, or at an older age. In one embodiment, treatment is initiated from ages about 4 years of age to about 12 years of age. In one embodiment, treatment is initiated on or after about 4 years of age. In one embodiment, treatment is initiated on or after about 5 years of age. In one embodiment, treatment is initiated on or after about 6 years of age. In one embodiment, treatment is initiated on or after about 7 years of age. In one embodiment, treatment is initiated on or after about 8 years of age. In one embodiment, treatment is initiated on or after about 9 years of age. In one embodiment, treatment is initiated on or after about 10 years of age. In one embodiment, treatment is initiated on or after about 11 years of age. In one embodiment, treatment is initiated on or after about 12 years of age. However, treatment can be initiated on or after about 15, about 20, about 25, about 30, about 35, or about 40 years of age. In one embodiment, treatment in utero is defined as administering the composition as described herein in the fetus. See, e.g., David et al, Recombinant adeno-associated virus-mediated in utero gene transfer gives therapeutic transgene expression in the sheep, Hum Gene Ther. 2011 April; 22(4):419-26. doi: 10.1089/hum.2010.007. Epub 2011 Feb. 2, which is incorporated herein by reference.

In another embodiment, the composition is readministered at a later date. Optionally, more than one readministration is permitted. Such readministration may be with the same type of vector, a different viral vector, or via non-viral delivery as described herein. In one embodiment, the vector is readministered to the patient to a different portion of the initially injected retina. In one embodiment, the vector is readministered to the patient to the same portion of the initially injected retina.

In yet another embodiment, any of the above described methods is performed in combination with another, or secondary, therapy. The secondary therapy may be any now known, or as yet unknown, therapy which helps prevent, arrest or ameliorate these mutations or defects or any of the effects associated therewith. The secondary therapy can be administered before, concurrent with, or after administration of the compositions described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In one embodiment, a method of generating a recombinant rAAV comprises obtaining a plasmid containing an AAV expression cassette as described above and culturing a packaging cell carrying the plasmid in the presence of sufficient viral sequences to permit packaging of the AAV viral genome into an infectious AAV envelope or capsid. Specific methods of rAAV vector generation are described above and may be employed in generating a rAAV vector that can deliver the codon optimized LCA5 in the expression cassettes and genomes described above and in the examples below.

In certain embodiments of this invention, a subject has Leber congenital amaurosis (LCA), for which the components, compositions and methods of this invention are designed to treat. As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, non-human primate and others. As used herein, the term "subject" is used interchangeably with "patient".

As used herein, the term "treatment" or "treating" is defined encompassing administering to a subject one or more compounds or compositions described herein for the purposes of amelioration of one or more symptoms of LCA. "Treatment" can thus include one or more of reducing onset or progression of LCA, preventing disease, reducing the severity of the disease symptoms, or retarding their progression, including the progression of blindness, removing the disease symptoms, delaying onset of disease or monitoring progression of disease or efficacy of therapy in a given subject.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, "disease", "disorder" and "condition" are used interchangeably, to indicate an abnormal state in a subject.

As used herein, the term "about" or "~" means a variability of 10% from the reference given, unless otherwise specified.

The term "regulation" or variations thereof as used herein refers to the ability of a composition to inhibit one or more components of a biological pathway.

Unless defined otherwise in this specification, technical and scientific terms used herein have the same meaning as commonly understood by one of ordinary skill in the art and by reference to published texts, which provide one skilled in the art with a general guide to many of the terms used in the present application.

EXAMPLES

The following examples are illustrative only and are not intended to limit the present invention.

Example 1: Recombinant rAAV and In Vitro Expression Studies

Retinal gene transfer using the most thoroughly studied recombinant AAV serotype, AAV2, has been carried out in >310 eyes in human subjects, and in 29 different clinical trials (clinicaltrials.gov). These trials target diverse diseases including autosomal defects (RPE65 deficiency, retinitis pigmentosa due to MERTK mutations, choroideremia, achromatopsia), a mitochondrial disease (Leber's hereditary optic neuropathy), a complication of age-related macular degeneration (choroidal neovascularization) and end-stage retinal degeneration (using optogenetic therapy). In the majority of these studies (18/29 or 18 of the 22 studies that employed AAV and subretinal injection), the goal was to target RPE cells efficiently. The net result has been a large body of safety data with respect to intra-ocular delivery of AAV. Subretinal injection is the same surgical approach that will be necessary to target photoreceptors in LCA5 patients.

Tremendous efforts have been made to develop a path to treat LCA5 and other diseases involving primary photoreceptor defects based on the information obtained. Unfortunately, AAV2 vectors do not target photoreceptors efficiently, and, as mentioned above, photoreceptors comprise the primary cell type in LCA5 and most other inherited retinal degenerations. For this reason, AAV7m8, a vector generated by evolutionary design was selected. This vector has been shown to target photoreceptors efficiently in diverse species (mice and non-human primates (NHPs)) and using different routes of administration.

The efficacy reported herein includes improvements in the ability of treated animals to navigate using visual cues, the restoration of visual pathways to the brain as shown by pupillometry, a reduction in photoreceptor apoptosis, and the preservation of functional photoreceptors with morphology and markers characteristic of this cell type, including presence of rhodopsin in the outer retina. The treated Lca5gt/gt photoreceptors show thick outer nuclear layers with preserved outer segments with stacked outer segment discs. This is in marked contrast to the untreated Lca5gt/gt retinas, which were reduced to a single row of non-contiguous photoreceptor nuclei by 3 months of age 19. The improvements were not permanent. However, they persisted for at least 3 months at which point there are no remaining photoreceptors in the untreated Lca5gt/gt mouse. Electroretinography and MEA results show that with successful transduction of photoreceptors, LCA5 gene therapy is capable of at least partially restoring responses mediated by both rod and cone photoreceptors. The responses of the cells have near normal kinetics, including responses reflecting the activity of a variety of ganglion cell types as well as a reversal of the dominating melanopsin responses observed in the untreated Lca5gt/gt retinas. The results are complementary with the pupillometry and visual behavior findings and will provide the framework for future studies aiming to further characterize and optimize the treatment effects (including studies of visual behavior in low illuminance conditions). These data provide hope that a similar gene augmentation approach in humans as that used in the Lca5gt/gt mouse could result in improved vision. It may be possible to further optimize the intervention to obtain an even more durable rescue effect. Alterations of components of the transgene cassette (promoter, etc.), and areas of retina treated may lead to additional benefit. Dosing studies should identify the optimal dose for therapeutic effect. The fact that LCA5 null patients may retain photoreceptors through adulthood (whereas photoreceptors are lost early in life in mice) suggests that there may be a wider window of opportunity in LCA5 humans compared to Lca5−/− mice. Photoreceptors have been documented in LCA5 null humans in the foveal outer nuclear layer, for up to 3 decades. This is important since successful gene therapy requires that the affected cells be present. We were able to demonstrate that the retained photoreceptors in an adult with LCA5 mutations showed a similar temporal pattern of light responsiveness (albeit reduced in amplitude) as photoreceptors from a normal-sighted individual. These results indicate that the residual photoreceptors in LCA5 patients are functional, despite the structural and physiological deficits. The primary cilia of iPSC-RPE derived from LCA5 mutant patients were much less numerous than those from the control cells. The facts that the ciliary defect in photoreceptors in the Lca5gt/gt mouse can be corrected by gene augmentation therapy and that the numbers of cilia can be increased to normal levels, suggest that it may be possible to ameliorate the ciliary defect present in humans with this condition.

A. Recombinant AAV

Recombinant AAVs were generated in the Center for Advanced Retinal and Ocular Therapeutics (CAROT) using AAV7m8 capsid, which is known to infect photoreceptors more efficiently than AAV2 (Dalkara D, Byrne L C, Klimczak R R, Visel M, Yin L, Merigan W H, et al. In vivo-directed evolution of a new adeno-associated virus for therapeutic outer retinal gene delivery from the vitreous. Sci Transl Med (2013) 5(189):189ra76. doi: 10.1126/scitranslmed.3005708.) The human (h) wildtype lebercilin-encoding optimized cDNA (hopt.LCA5) was custom-designed for optimal codon usage and synthesized by DNA2.0 (Menlo Park, Calif.). The LCA5 cDNA was placed under the control of a hybrid chicken β-actin (CBA) exon 1 flanked by intron 1 sequences and with cytomegalovirus (CMV) immediate early enhancer (FIGS. 1A and 1E). A bovine growth hormone poly(A) followed the cDNA. A long stuffer sequence was included to prevent reverse packaging (i.e. of non-transgene containing) vector from the AAV2 inverted terminal repeats. The vectors were made by triple transfection and formulated in excipient consisting of phosphate-buffered saline (PBS) containing and 0.001% Pluronic F68 (PF68). See, e.g. Mizukami, Hiroaki, et al. A Protocol for AAV vector production and purification. Diss. Di-vision of Genetic Therapeutics, Center for MolecularMedicine, 1998. Control vectors incorporated the enhanced green fluorescent protein (eGFP) cDNA in place of the LCA5 cDNA.

The rAAVs were tested for expression of the appropriate sized transgenic protein by Western blot. 8431 cells were plated at $2 \times 10^6$ cells per well. Two days after plating, cells were transduced with AAV7m8.hopt.LCA5 (or AAV7m8.CBA.EGFP as control) at $1 \times 10^5$ or $5 \times 10^5$ vg. 48 hours later, cells were harvested and processed for electrophoresis and Western blot. Antibodies include an LCA5 rabbit polyclonal antibody (Proteintech, Rosemont, Ill.) and the signals are quantified, with each value is corrected for background and protein loading differences through normalization with the GAPDH immunosignal.

The AAV7m8.CBA.hopt.LCA5 virus is able to drive efficient expression of the LCA5 transgene in 8431 cells. Production of the predicted ~81 kDA Lebercilin protein after infection with AAV7m8.CBA.hopt.LCA5 demonstrates a dose-dependent responses.

Example 2: LCA Mouse Model Lca5−/− Mouse Studies

Development of a proof-of-concept of gene augmentation therapy in the Lca5gt/gt mouse model entails several challenges: 1) because retinal degenerative changes begin very early and progress rapidly, intervention must be carried out in neonatal mice; 2) since this is a photoreceptor-specific disease, recombinant AAV vectors must be employed that target photoreceptors efficiently. The AAV2 vector used extensively in animal and human studies to target RPE cells does not target photoreceptors as efficiently as other AAV serotypes as shown by transduction comparisons of different serotypes after infection with equivalent doses. Ideally, therapeutics should be developed that could ultimately progress to human clinical trials; and 3) outcome measures must be developed that accurately identify and quantify improvements in retinal and visual function, which is so low at baseline that it is difficult to score. Here we used a recombinant AAV vector (AAV7m8) designed by directed evolution, to deliver a codon optimized human lebercilin-encoding cDNA. By using AAV7m8 to deliver LCA5 to the diseased photoreceptors early in life, we show that gene augmentation therapy results in both structural improvement of the Lca5gt/gt mouse retina and functional improvement of its vision.

Lebercilin localizes to connecting cilia of photoreceptor cells (22). The connecting cilium is a transition zone between the photoreceptor cell body inner segment and the antennae-like outer segments that supports selective transport of proteins and membrane vesicles. The connecting cilium is thus the conduit supporting bi-directional protein trafficking along ciliary microtubule tracks, or intraflagellar transport (IFT). Using both quantitative affinity proteomics (affinity purification, mass spectrometry and bioinformatics analyses) and a genetically engineered mouse model, Boldt et al demonstrated that LCA5 mutations interfere with IFT,(22) thereby causing an early-onset defect in photoreceptor outer segment development and a failure to correctly traffic two different proteins expressed specifically in photoreceptors, arrestin and opsin. Knockout of the Lca5 gene in mice resulted in a retinal degeneration phenotype. The Lca5−/− mice develop patches of de-pigmented retina, never develop outer segments and lack cone and rod ERG responses to light. There is an early and rapidly progressive retinal degeneration and only a single (sickly) row of nuclei is present in the ONL by 2 months of age. (22) Thus, the Lca5−/− mice were utilized as an animal model for LCA.

Adult Lca5$^{gt/gt}$ (Lca5−/−) mice were purchased from Jackson Labs (Bar Harbor, Me.) and a line was generated by brother-sister crossings. Verification of the genotype of all animals used in the study was performed (see Supplementary Methods). Mice were on a 12-hour light/12-hour dark cycle, and food/water was provided ad libitum. The studies were performed in compliance with federal and institutional regulations.

Subretinal injections were carried out unilaterally in neonatal mice as described previously (28) in cohorts of pups. Anesthesia in mice at postnatal day 5 (PN5) was hypothermia. At postnatal day 15 (PN15), animals were anesthetized with ketamine/xylazine. Table 1 shows the number of animals used per cohort.

Intravitreal injections of AAV7m8 were also carried out since this vector had been shown previously to penetrate the mouse retina from the vitreal aspect to target photoreceptors. (25) AAV7m8.CBA.hopt.LCA5 was injected at a total of $9.20 \times 10^9$ vg in 1 µl in cohort 1 (Table 1). The injection solution contained 5% v/v of AAV7m8.CBA.EGFP so that the area of injection could be identified with certainty at later time points through presence of enhanced green fluorescent protein (EGFP). Additional animals received sham injection (cohort 2), received injection of AAV7m8.CBA.EGFP alone (cohort 3), or were maintained uninjected as controls (cohort 4). After injection, pups were returned to their mothers until the time of weaning.

TABLE 1

Cohorts of neonatal Lca5−/− mice injected at the designated postnatal day (PN) and studied in vivo.

| Group Number | Testing material | ROA | Testing material | ROA | Animal Number |
|---|---|---|---|---|---|
| | | Eye #1 | | Eye #2 | |
| | | PN5 | | | |
| 1 | excipient | intravitreal | NA | sham | 5 + 4 |
| 2 | excipient | subretinal | NA | sham | 7 + 4 |
| 3 | AAV7m8.hopt.LCA5 (+5% AAV7m8.GFP) | intravitreal | NA | sham | 10 + 8 |
| 4 | AAV7m8.hopt.LCA5 + 5% AAV7m8.GFP) | subretinal | NA | sham | 17 + 8 |
| | | PN15 | | | |
| 5 | excipient | intravitreal | NA | sham | 13 |
| 6 | excipient | subretinal | NA | sham | 6 |
| 7 | AAV7m8.hopt.LCA5 (+5% AAV7m8.GFP) | intravitreal | NA | sham | 13 |
| 8 | AAV7m8.hopt.LCA5 (+5% AAV7m8.GFP) | subretinal | NA | sham | 11 |

ROA—route of administration.

Ophthalmoscopy was carried out about 1 month post injection to verify that media were clear, retinas were not detached, and thus that there had been no surgical complications. Any animals that had corneal or vitreal opacities were excluded from further study.

Cohorts of mice were bred and studied, and injections were carried out at early postnatal (PN5) and juvenile (PN15) time points (Table 1). Injections were found largely without complications. After injections at PN5, the majority of the animals were found to be free of corneal or vitreal opacities that would interfere with further testing. The few animals with opacities were excluded from further analyses.

Figures 1F, 1G:
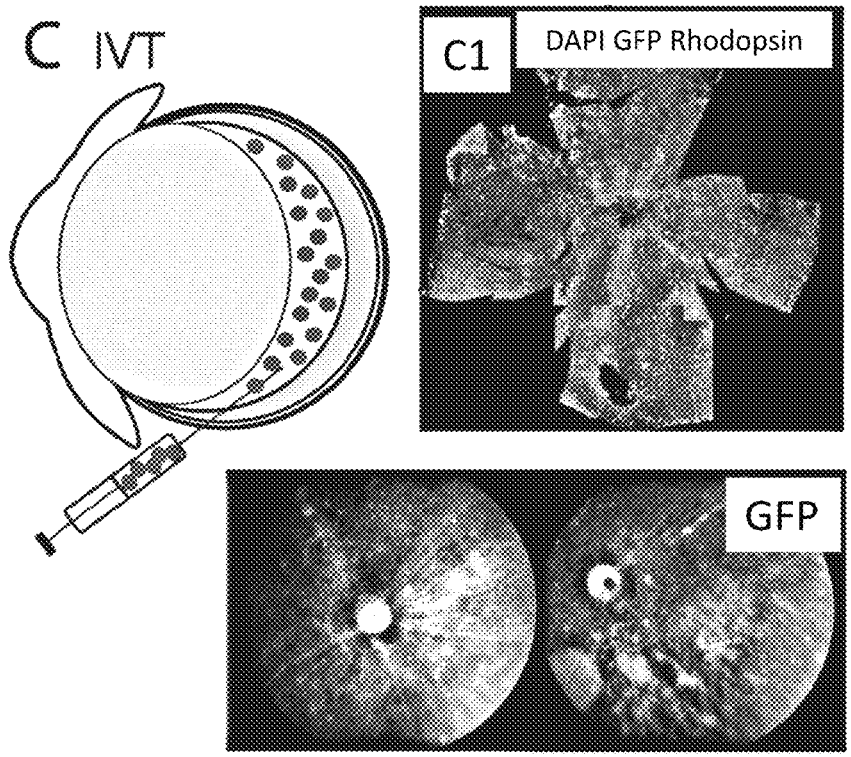
FIGS. 1G-1H provide immunofluorescence analysis of eyes injected with AAV7m8-hopt-LCA5 at P5 and analyzed at P15 shows Lebercilin co-localizing with the base of tubulin-positive outer segments as described in Examples 1, 2 and 4. After intravitreal injection (IVT, FIG. 1G) or subretinal injection (SR, FIG. 1L), Lebercilin was distributed throughout the retina, which was nearly devoid of photoreceptors at P95. In contrast, lebercilin is absent in untreated P15 and P95 Lca5−/− retinas. SR, subretinal; IVT, intravitreal; (−) Untreated Lca5−/−. Cartoons are provided showing the intravitreal injection scheme (FIG. 1G) and subretinal injection scheme (FIG. 1H).
Figure 1H:
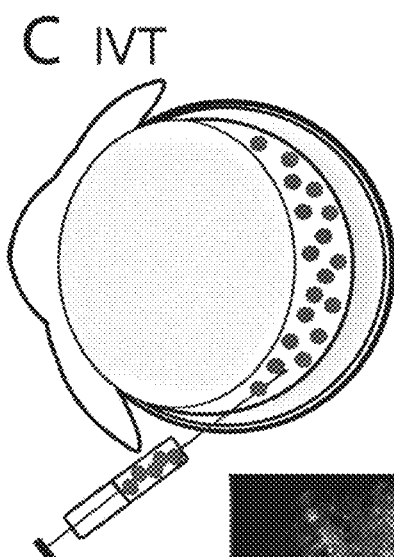
Figure 1H:
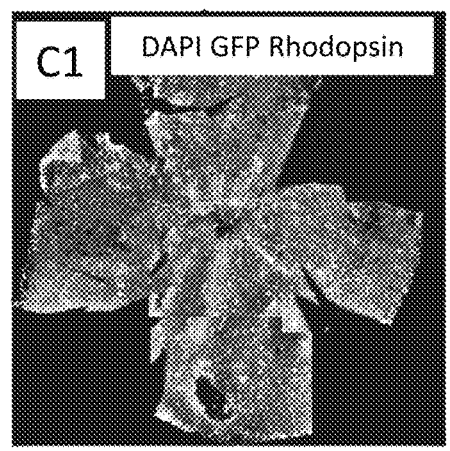
Figure 1H:
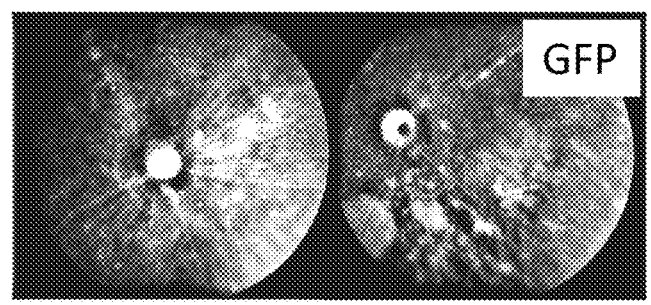
Figure 1I:
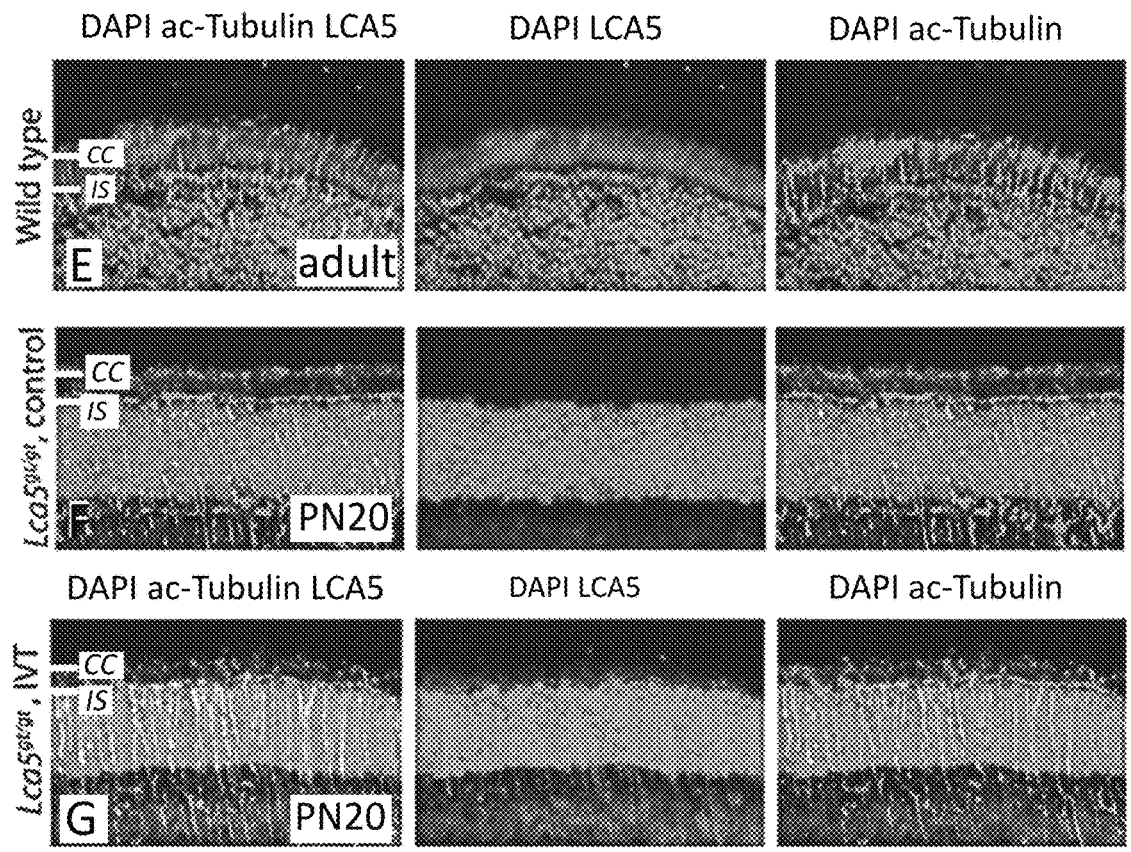
FIG. 1I shows expression of Lebercilin in both wild type mouse and Lca5−/− mice at P20 injected with the AAV.LCA5 vector subretinally.

The AAV7m8.CβA.hopt-LCA5 virus was able to drive efficient expression of the human LCA5 transgene in mouse retina (FIGS. 1A and 1B) following both intravitreal (IVT) and subretinal (SR) administration (FIGS. 1C and 1D, respectively). Western blot analysis shows production of the predicted ~81 kDa LCA5 protein after intra-ocular delivery with AAV7m8.CβA.hopt-LCA5 in Lca5gt/gt and wild type mice at PN20 (FIG. 1B). Immunofluorescence analysis shows presence of lebercilin protein in the ONL, inner segments (IS) and connecting cilia (CC) in wild type adult retina (FIG. 1E). After injecting AAV7m8.CβA.hopt-LCA5 intravitreally or subretinally in Lca5gt/gt retinas, lebercilin is found in CC as well as IS and ONL (FIGS. 1G and 1H). In contrast, in sham-injected Lca5gt/gt retina, there is no lebercilin (FIG. 1F). In addition, after IVT injection, a substantial number of Muller cells produce lebercilin (FIG. 1G).

Example 3: Tests of Retinal/Visual Function

Tests of visual and retinal function included a light-cued water maze (2-3 months post injection), pupillometry (2.5 months post injection), multi-electrode array (3 months post injection) and electroretinography utilizing the mice indicated or described in Example 2. Retinas were then evaluated for histopathology and immunofluorescence as described in Example 4. A thorough tissue analysis was also followed.

A. Electroretinography

We recorded ERGs from 8 Lca5gt/gt mice, 5 wild-type animals, and 16 Lca5gt/gt mice whose left eyes had been injected with excipient and the right eyes with AAV7m8. CβA.hopt-LCA5 on PN5 intravitreally. None of the eyes of Lca5gt/gt uninjected controls or Lca5gt/gt eyes injected with excipient (a total of 32 eyes) produced detectable ERG responses. Out of 16 eyes injected with AAV7m8. CβA.hopt-LCA5, four showed ERG responses to dim flashes of light in the dark-adapted state consistent with rod-mediation of the signals, as well as mixed rod-cone responses to brighter flashes of light that resembled a smaller, scaled version of wild-type (WT) mixed rod-cone ERG waveforms (Figure S2). Light-adapted ERGs were also detectable in these eyes suggesting cone-mediation of the photopic responses. Detectable ERGs post-treatment ranged in amplitude from 20 to 25% the WT amplitudes (Figure S2). The results suggest restoration of both rod and cone photoreceptor function after gene therapy in some of the animals. The inconsistency of the full-field ERG findings likely reflect incomplete retinal coverage and/or tissue damage (cataracts, unresolved detachment, etc.) sustained after these technically challenging subretinal injections, performed in the early post-natal period. The results, however variable in magnitude or infrequent, were dramatically different from the undetectable ERGs observed in untreated Lca5gt/gt eyes. B. Water maze navigation study Water maze testing was performed to evaluate each animal's ability to identify the chamber containing a submerged platform in a 5-chamber water maze (FIG. 11). The apparatus was maintained in a room without extraneous light and the light source was placed directly over the platform prior to the test. The dark-adapted mouse was released in the center of the maze and given 60 seconds, without interruption, to find and place all four paws on the lit platform.

Training was carried out in room light (about 200 Lux) prior to dark adapting the mice and carrying out the test under dim light procedures. During the training, if the mouse was unable to find the platform at the end of the 60 seconds, the experimenter guided the mouse to the platform. For each trial, the light and platform were placed in a different chamber using random selection.

Training pass criteria were defined as the ability of the mouse to independently enter the correct chamber, without deviating into a different chamber, and mount the platform within 60 seconds in more than 5 of 9 sequential trials. All mice were trained for 5 days regardless of the day that training pass criteria were met. Testing was carried out for 4 days using the same procedure as that used in training but with a series of filters to further dim the light source. Through use of filters the luminances were: $1.06 \times 10^5$, $8.69 \times 10^3$, $5.87 \times 10^2$ scot cd m$^2$, or with the light off, the luminance was 0 scot cd m$^2$.

Animals were trained and then tested with the light-cued water maze at 2-2.5 months of age. Light-cued water maze test results showed that the AAV7m8.CBA.hopt.LCA5 subretinally or intravitreally injected groups performed significantly better than controls. (Table 2B; see values in BOLD; FIG. 3). Table 2A shows the raw data, which are numbers of animals analyzed in each cohort and then tested under the designated light levels using the water maze. Table 2B shows the results of statistical analyses using one-way analysis of variance (ANOVA). The treated animals were able to pass the test at $8.69 \times 10^2$ scot cd m$^2$ whereas animals from the control excipient-injected cohort were not ($p<0.01$).

TABLE 2

Results of water maze testing in Lca5−/− mice.

| | | Mean (SD) for Pass % Light Level (scot cd m$^2$) | | | |
|---|---|---|---|---|---|
| (A) Intervention | n | $1.06 \times 10^5$ | $8.69 \times 10^3$ | $5.87 \times 10^2$ | 0 |
| Excipient (PBS) Intravitreal at PN5 | 5 | 53.3 (36.36) | 31.1 (9.29) | 31.1 (21.38) | 13.3 (9.29) |
| Excipient (PBS) Intravitreal at PN15 | 13 | 46.15 (17.5) | 33.31 (17.57) | 17.08 (9.74) | 33.32 (13.64) |
| Excipient (PBS) Subretinal at PN5 | 7 | 73.0 (16.78) | 34.9 (16.28) | 22.2 (16.96) | 14.3 (12.35) |
| AAV7m8-hopt-LCA5 (+5% GFP) intravitreal at PN5 | 10 | 70.0 (17.43) | 52.3 (13.93) | 40.0 (21.09) | 15.5 (13.03) |
| AAV7m8-hopt-LCA5 (+5% GFP) intravitreal at PN15 | 13 | 53.85 (24.80) | 28.19 (17.35) | 18.78 (11.45) | 27.75 (11.64) |
| AAV7m8-hopt-LCA5 (+5% GFP) subretinal at PN5 | 17 | 88.9 (16.2) | 77.1 (15.9) | 47.7 (23.8) | 14.4 (8.6) |
| (B) P-value for Pairwise comparison | | Light Level (scot cd m$^2$) | | | |
| with PBS control group† | | $1.06 \times 10^5$ | $8.69 \times 10^3$ | $5.87 \times 10^2$ | 0 |
| AAV7m8-hopt-LCA5 intravitreal at PN5 vs. Excipient intravitreal at PN5 | | 0.24 | 0.01 | 0.46 | 0.74 |

TABLE 2-continued

Results of water maze testing in Lca5−/− mice.

| | | | | |
|---|---|---|---|---|
| AAV7m8-hopt-LCA5 intravitreal at PN15 vs. Excipient intravitreal at PN15 | 0.37 | 0.46 | 0.69 | 0.48 |
| AAV7m8-hopt-LCA5 subretinal at PN5 vs. Excipient subretinal at PN5 | 0.042 | 0.00001 | 0.018 | 0.981 |

C. Pupillary Light Reflex

The amplitudes of pupillary constriction were measured during a series of 10 light flashes per eye. Flash intensity was 1,000 scot lux. PLRs were defined as having a maximum amplitude of pupil constriction response within the 0.6-1.2 second interval following the flash that was more than 3 standard deviations of the pre-stimulus diameter. A scientist masked to the treatment paradigm evaluated the data from each animal prior to analyses to be sure that each pupil was tracked accurately. If not, that particular animal was excluded from further analyses.

For statistical analyses, normalized pupil diameters from the treated (right) and contralateral sham-injected control (left) Lca5−/− eyes were compared at each light intensity. By dividing the normalized amplitude of constriction of the treated eye with that of the untreated eye, the percentage of the Maximum Differential Amplitude of Response (MDAR) could be obtained. Higher percentage of the MDAR indicated a stronger response to intervention. Additional age-matched untreated Lca5−/− and wildtype (C57Bl/6) mice were used as positive and negative controls, respectively. The MDARs of untreated Lca5−/− and C57Bl/6 mice were about 0 since there was minimal difference between the two eyes.

Additional analyses evaluated the magnitudes of amplitude of pupillary constriction in the right eyes of the different cohorts of mice. Thus, the amplitudes of constriction could be compared between treated and untreated Lca5−/− mice and untreated C57Bl/6 mice.

Analyses of amplitudes of the pupillary light reflex generated by stimulation of the treated vs control eyes revealed a significant ($p<0.05$) improvement in amplitude of the pupillary reflex in eyes of Lca5−/− mice that were treated either subretinally or intravitreally with AAV7m8.hopt-LCA5 compared to untreated control Lca5−/− animals (FIG. 2). There was significantly improved Pupillary Light Reflex (PLR) was detected in animals injected at PN5 by either route of delivery (FIGS. 2A, 2B, 2H, and 2I) and at PN15 with subretinal delivery, although there was also a trend to improvement with intravitreal delivery (FIGS. 2H and 2I).

D. Multi-Electrode Array

Multi-electrode array (MEA) testing was carried out on 5 animals 2.5-3.5 months after they had received unilateral intravitreal injection with AAV7m8.CMV/CBA.hopt.LCA5 (about $9.87 \times 10^{10}$ vg/eye) spiked with 5% (v/v) AAV7m8.CBA.GFP. Contralateral eyes were sham-injected and used as negative controls. Five untreated age-matched wildtype (WT) C57Bl/6 mice served as positive controls. Retinas from light-adapted mice were dissected under red light and mounted ganglion cell side down in the perforated MEA chamber. Presence of GFP in the explants confirmed exposure of photoreceptors to AAV. Calibrated full field flashes of 455 nm light (efficiency of pigment excitation about 40%:rhodopsin and M-opsin; about 0.2%:S-opsin) of different intensities were used for light stimulation (2 s flashes at 0.1 Hz or 50 ms flashes at 4 Hz). Data were analyzed using custom code in Matlab (MatLab, Natick, Mass.); spike sorting was performed in Plexon Offline Sorter (Plexon, Dallas, Tex.). AAV7m8.CβA.hopt-LCA5 at PN5 were probed using multi-electrode array (MEA) analyses. The rationale for using MEA is that it measures the output signal of the retina sent to the brain and thus, in addition to testing photoreceptor function, also provides information about retinal wiring. Of the five retinas/animals tested with MEA, two had had clearly detectable rod and cone ERGs (see a representative record in Figure S2), one had a residual small, ~10 □V ERG, and two did not have any detectable ERG. Three out of 5 AAV7m8.CBA.hopt.LCA5-injected retinas had strong light responses, one showed median responses and 1 showed minimal response in MEA testing (FIG. 5A-D). Responses became detectable at scotopic intensities (42-112 photons*s$^{-1}$*μm$^{-2}$, or on average, 8.28e1 hv/μm$^2$; 455 nm) and strong responses were observed through the brightest photopic intensity of 2.00e9 photons*s$^{-1}$*m$^{-2}$. Assuming collecting area for rods and cones for end-on illumination to be around 1 μm2 at the wavelength of peak sensitivity 23, 24 (note that both in ERG and our MEA experiments light enters the retina from the ganglion cell side) and efficiency of stimulation by 455 nm light of rhodopsin and of M- and S-cone opsins to be around 60%, 50% and 0.3% respectively 25-27 the dim light generating clearly detectable responses in our experiments should produce less than 70 photoisomerizations per second per cell in rods, less than 60 in M-cones, and around 0.3 photoisomerizations per second in S-cones. Data from suction pipette recording show that at this rate of pigment excitation rods can generate detectable light responses (response amplitude above 20% of the maximum) while cone response is expected to be at least 20 times smaller under the most favorable conditions (dark adapted Mcones in rod-transducin knockout retinas) and should be undetectable in rod dominated mouse retina 25, 26, 28 (note that collecting area for side-on illumination in suction pipette recording is around 0.5 μm-2 for rods and 0.2 μm-2 for cones). Thus observation of light responses at the dimmer intensity range in our experiments proves recovery of rod function in the treated Lca5gt/gt retinas. Responses at the brighter end of intensities should originate in cones (the brightest intensity should be more than capable of driving both M- and S-cones by producing around 1.00e9 and 6.00e6 photoisomerizations per second per cell in M- and S-cones respectively). As expected for rod/cone driven responses, after exposure to the brightest stimulation series at the end of the 1st intensity series run (light sensitive retinas were subjected to at least 2 intensity series runs ranging from the dim scotopic to the brightest photopic intensities in ~0.5 log increments), scotopic responses disappeared, but photopic responses were not significantly affected (FIGS. 5 C and D). WT and treated Lca5gt/gt retinas were also responsive to 4 Hz flicker stimulation at the intensities expected to drive cone responses (Data not shown). Retinas from sham-injected contralateral eyes showed minimal to abolished responses with high spontaneous firing and prominent melanopsin responses.

Slow melanopsin driven responses were also detected in both AAV7m8.CβA.hopt-LCA5-treated Lca5gt/gt retinas and retinas from wild type mice (manifesting as elevated firing rate at the start of the 2nd flash due to the slow recovery after the 1st flash in a series) of melanopsin response appears to be muted in treated retinas compared to the untreated ones.

TABLE 3

Summary of MEA responses in treated and control Lca5−/− mice

| treatment/outcome | number of records | comments |
| --- | --- | --- |
| treated Lca5−/− retina/ light responsive | 4 | 3 retina with responses nearly undistinguishable from WT, one with weaker but still prominent responses |
| treated Lca5−/−retina/ not light responsive | 2 | one with weaker spontaneous firing |
| untreated Lca5−/− (left retina control)/not light responsive | 6 | all responding Lca5−/− retinas (right) have corresponding control from the left eye |
| WT/light responsive | 5 | intensity range from 40 to 2e9 photons per um^2 per second |

All retinas (except one treated Lca5−/− retina) demonstrated strong spontaneous firing, when tested for melanopsin-driven responses (long interflash interval to allow for slow recovery). Untreated Lca5−/− retinas demonstrated strong melanopsin-driven responses.

Two of the treated Lca5−/− retinas had signs of post-injection injury and did not show light responses despite strong spontaneous firing.

Responses of the AAV7m8.CBA.hopt.LCA5-treated retinas were similar to those of untreated wildtype retinas. One treated retina tested after the shortest post injection period demonstrated reduced light sensitivity and absence of OFF- and sustained ON-responses (red downward triangles on FIG. 5D). Development of the OFF-responses appears to require longer time post injection compared to the ON-responses, consistent with increased variability in the OFF-response amplitudes observed for 10 the treated retinas. Function of all ganglion cell types identifiable in the WT retinas under fullfield stimulation was detected in the Lca5gt/gt AAV-treated retinas after spike sorting (Figure S10). Strong responses were observed under scotopic and photopic stimulation, up to the brightest intensities (almost 100 mW/cm$^2$). As expected for rod/cone driven responses, after exposure to the brightest light, scotopic responses disappeared but photopic responses were not significantly affected (data not shown).

Responses in AAV7m8.hopt.LCA5-treated retinas became detectable at scotopic intensities (42-112 photons*s-1*μm-2, or on average, 8.28e1 hv/μm2; 455 nm) and strong responses were observed through the brightest photopic intensity of 2.00e9 photons*s-1*μm-2. Retinas from sham-injected contralateral eyes showed minimal to abolished responses (Data not shown. Control Lca5−/−). Responses in AAV7m8.hopt.LCA5-treated retinas were similar to those in retinas of wildtype mice. Flicker responses showing that after exposure to the brightest light (2E9 hv/cm2), photopic responses were not significantly affected (Data not shown, Lca5−/− treated). Flicker response intensity series (going from 3.53E2-1.52E6 hv/cm2 of representative AAV7m8.CBAhopt.LCA5-treated retina showed that as the light intensity increases, the amplitude of response increases. Testing of rod and cone endurance responses after the brightest flashes showed persistence of the cone response, similar to that found in wildtype retinas. Flicker response testing shows similar responses in treated Lca5−/− retinas compared to retinas of wildtype mice. Firing rate of rods and cones in treated Lca5−/− retinas approaches that of wildtype retinas (as opposed to the control untreated Lca5−/− retinas) as a function of light intensity.

Response kinetics were similar to those in WT retinas (Data not shown). Light sensitivity was slightly lower in treated Lca5−/− vs the most sensitive WT retinas where first responses were detected at 8-21 photons*s$^{-1}$*μm$^{-2}$ (Data not shown.). All ganglion cell types identifiable in the WT retinas under full field stimulation (ON-, OFF and ON/OFF-types) were detected in the Lca5−/− treated retinas after spike sorting. WT and treated Lca5−/− retinas were responsive to 4 Hz flicker stimulation at 3.53e2-2.00e9 photons*s$^{-1}$*μm$^{-2}$ (Data not shown.). All untreated Lca5−/− retinas showed slow melanopsin driven responses at brighter intensities which were absent in the light sensitive treated Lca5−/− retinas. A summary of the findings is shown in Table 3.

Though results obtained with electroretinography and MEA experiments demonstrated restoration of rod and cone function in at least some animals, these methods were inadequate for assessment of intervention efficiency in a majority of animals since only a quarter of treated mice produced useful ERG signals. Therefore we based assessment of intervention efficacy on two additional approaches, analyses of pupillary light reflexes (PLR) and visual behavior, which offered, first, higher sensitivity than electrophysiology, and, second, proof that treatment of the Lca5gt/gt retina with AAV7m8. CβA.hopt-LCA5 results in light-induced signal relayed beyond the retina, through visual pathways to the brain.

Figure 2F:
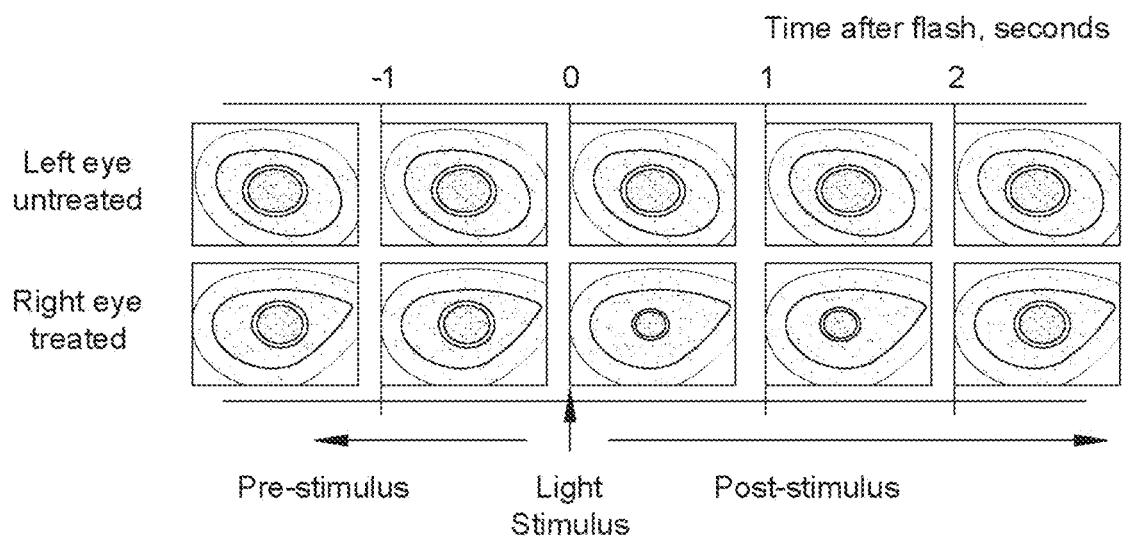
Figure 2G:
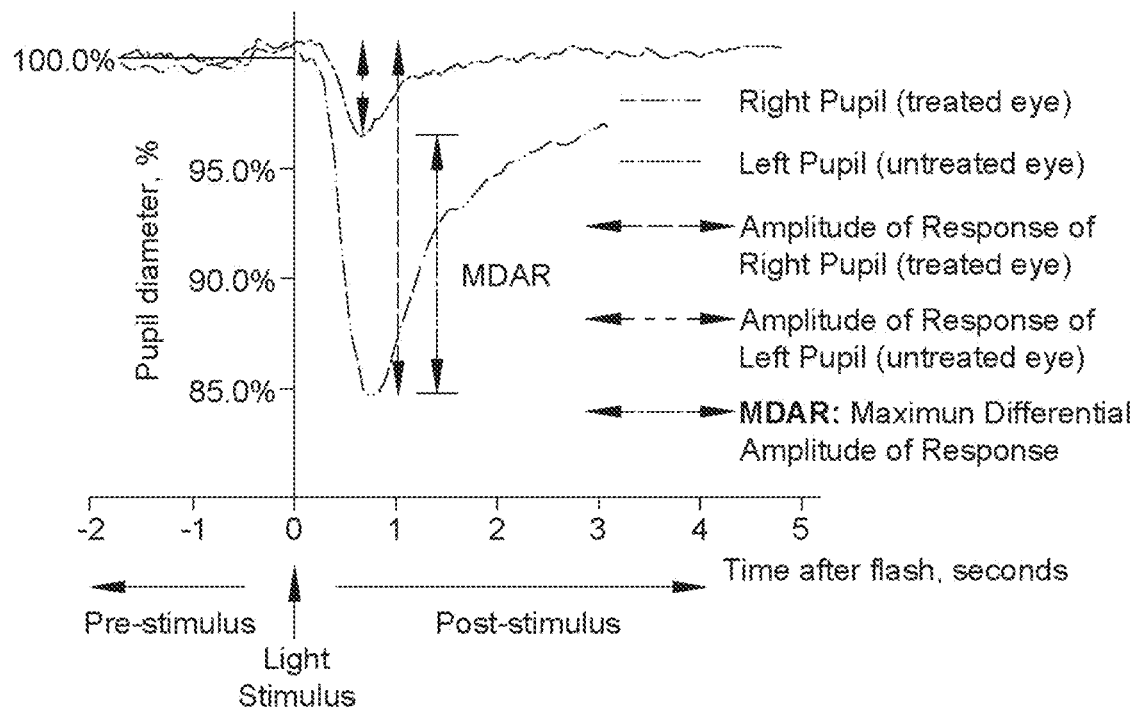
Figure 2H:
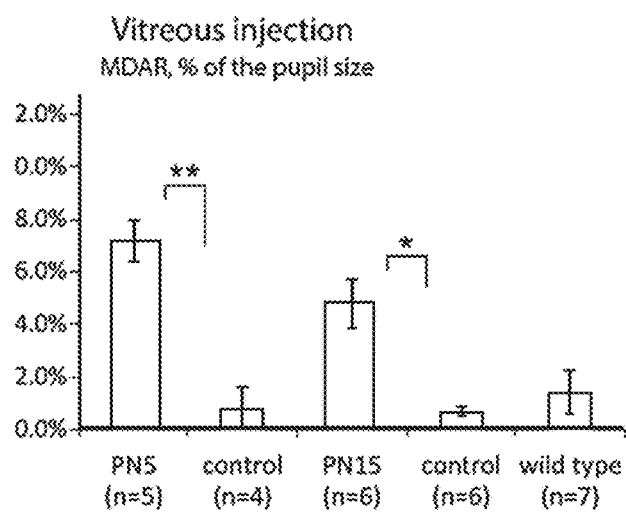
Figure 2I:
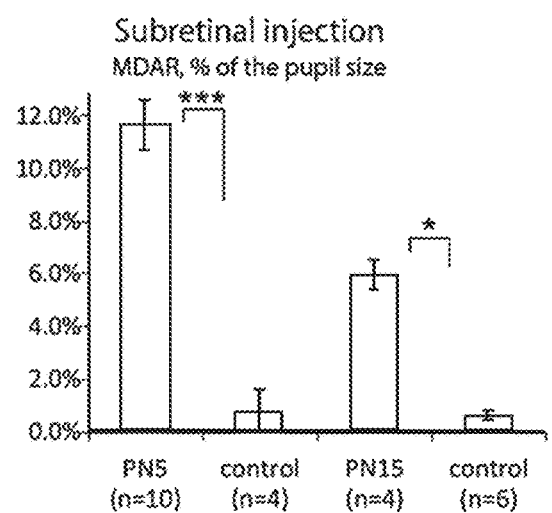

Pupillary light reflexes (PLR) are dependent upon relay of signals initially from photoreceptors to retinal ganglion cells, then to the Edinger-Westphal nucleus in the brain, and finally back to the pupillary sphincter muscle via the ciliary ganglion, which controls iris diameter. Analyses of the PLR following stimulation of the treated vs. control eyes revealed a significant (p<0.05) increase in amplitude of the PLR in eyes of Lca5gt/gt mice treated with AAV7m8.CβA.hopt-LCA5 compared to sham-injected controls (FIG. 2C). There was a significantly improved PLR detected in animals injected at PN5 either intravitreally or subretinally (FIGS. 2A-2B and 2E-2F) such that near-wild type responses were observed (FIG. 2D). Statistically significant improvement of the amplitude of the PLR was also demonstrated through comparisons of the maximum differential amplitude of response (MDAR; FIG. 2G-2I; FIG. 5I). Animals receiving AAV7m8.CβA.hopt-LCA5 by either IVT or SR delivery also showed significantly improved PLR as quantified by MDAR (FIGS. 2H and 2I).

Since PLRs demonstrate retinal signaling and function but do not provide information on formed vision, we used a light-cued water maze test to measure functional vision as described above. The majority of untreated wildtype (normal-sighted) mice were able to navigate the water maze successfully at all light levels whereas untreated Lca5gt/gt were severely impaired (Table 2, FIG. 3A). Results from water maze testing showed that both IVT and subretinally AAV7m8.CβA.hopt-LCA5 injected Lca5gt/gt animals performed better than uninjected controls in a statistically significant manner under at least one light condition. (Table 2; FIG. 3). The animals treated subretinally at PN5 showed a significantly improved pass rate at every lighting test condition (1.06E+05, 8.69E+03, and 5.87E+02 scot cd m-2), than control excipient-injected cohort (p<0.01). When animals were injected at PN15 (IVT or SR), improvements were minimal (FIG. 3). To confirm that mice used only the given light cue, testing was performed under no light condition (0.00 scot cd m2) and over 90% of mice failed the test (including normal-sighted mice; FIG. 3B).

Example 4: Ocular Histology, Histopathology, Immunofluorescence and TUNEL Assay

Histologic rescue of Lca5gt/gt photoreceptors after treatment with AAV7m8.CβA.hopt-LCA5 at PN5 was assessed both through evaluation of molecules relevant to proper function of the phototransduction cascade and though structural measures. Animals as described in Example 2 and 3 were euthanized at 3 months of age. Eyes were enucleated and retinal sections evaluated by modifications of methods described by Boldt et al.(22) Tissue was fixed with 4% paraformaldehyde in PBS and then cryoprotected in 30% sucrose/PBS prior to freezing and generating cryosections. Histopathology was analyzed by examination of 4',6-diamidino-2-phenylindole (DAPI, Thermo Fisher Scientific, Philadelphia, Pa.)-stained sections and/or by staining with hematoxylin and eosin. For immunofluorescence studies, sections were incubated with anti-lebercilin (1:300, (12, 22) in the presence of blocking solution, washed and then treated with Cy3-conjugatioed secondary antibodies. Additional antibodies used were anti-rhodopsin (1:500, Leico Technologies), anti-red/green cone opsin (1:250, Chemicon), anti-acetylated tubulin (1:1,000, Sigma-Aldrich). Stained sections were cover-slipped with Citifluor mounting medium containing DAPI (Electron Microscopy Services, Hatsfield, Pa.). TUNEL staining was carried out using a terminal deoxynucleotidyl transferase (TdT) dUTP nick-end labeling (TUNEL) assay kit following manufacturer's recommendations (Vector Laboratories, Burlingame, Calif.). Sections were evaluated with a Zeiss Axio Imager M2 microscope equipped with epifluorescence and Axio-Vision 4.6 software and with a confocal laser-scanning microscope (Olympus Fluoview 1000, Center Valley, Pa., USA). Transmission electron microscopy (TEM) was carried out on designated tissue samples using a FEI-Tecnai T12 S/TEM.

Immunofluorescence analysis of eyes injected with AAV7m8-hopt-LCA5 at PN5 and analyzed at PN15 showed Lebercilin co-localized with the base of tubulin-positive outer segments. After intravitreal injection, Lebercilin was distributed throughout the retina, which was nearly devoid of photoreceptors at PN95. In contrast, Lebercilin was absent in untreated PN15 and PN95 Lca5−/− retinas.

Hematoxylin and eosin-stained treated and control retinal sections at PN40 vs. PN99 comparing results after intravitreal (IVT) or subretinal (SR) injection of AAV7m8.hopt-LCA5 (with 5% v/v AAV7m8.eGFP) were compared with sham injection. Micrographs of hematoxylin and eosin-stained (H&E) retina showed that inner/outer segments (IS/OS) and ONL are preserved through the 3 months timepoint (PN99) after either IVT or SR injection of AAV7m8.hopt-LCA5 (Data not shown). In contrast, sham-injected control retinas lack such layers at PN99 (Data not shown). Further, lebercilin was detected in the treated, but not in sham treated control retinas (Data not shown). Persistent expression of rhodopsin in the ONL was also confirmed by immunofluorescence analysis (Data not shown) but only seen in treated eyes.

Figure 4:
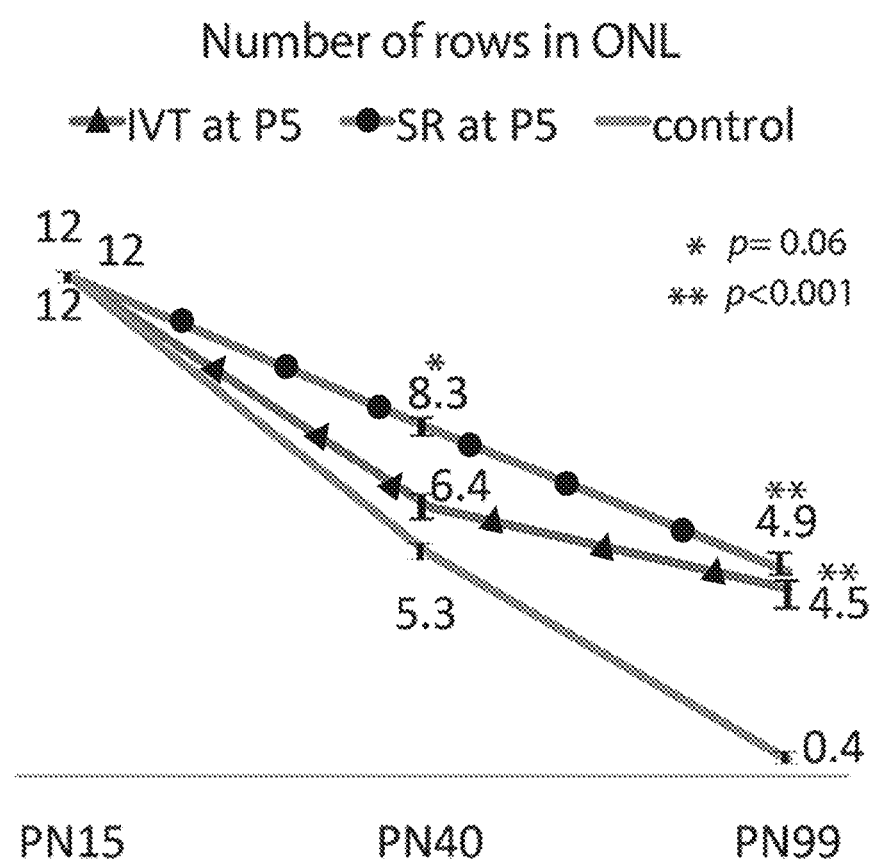
FIG. 4 is a graph providing results of representative histology after AAV7m8.hopt-LCA5 delivery to the Lca5gt/gt retina at postnatal day (PN)5. The graph shows the number of rows in the outer nuclear layer (ONL) after IVT or SR treatment with AAV.LCA5 vs. sham-injection.

The thickness of photoreceptor cell layers in retinas that were treated by IVT or SR injection with AAV7m8.CβA.hopt-LCA5 at PN5 was significantly greater than in control retinas (FIG. 4). There was also a noticeable border in thickness between the areas of retinas exposed to or unexposed to AAV in retinas treated by subretinal injection (Data not shown). The preservation of photoreceptor layers persisted through the latest timepoint (PN99). The increased thickness was due to an increased number of rows in the outer nuclear layer, and presence of inner and outer segments (FIG. 4). Consistent with this, there was a much higher proportion of dying photoreceptors in control compared to AAV.LCA5-treated retinas as judged by TUNEL labeling, particularly within the first month after intervention (Data not shown).

Figure 5A:
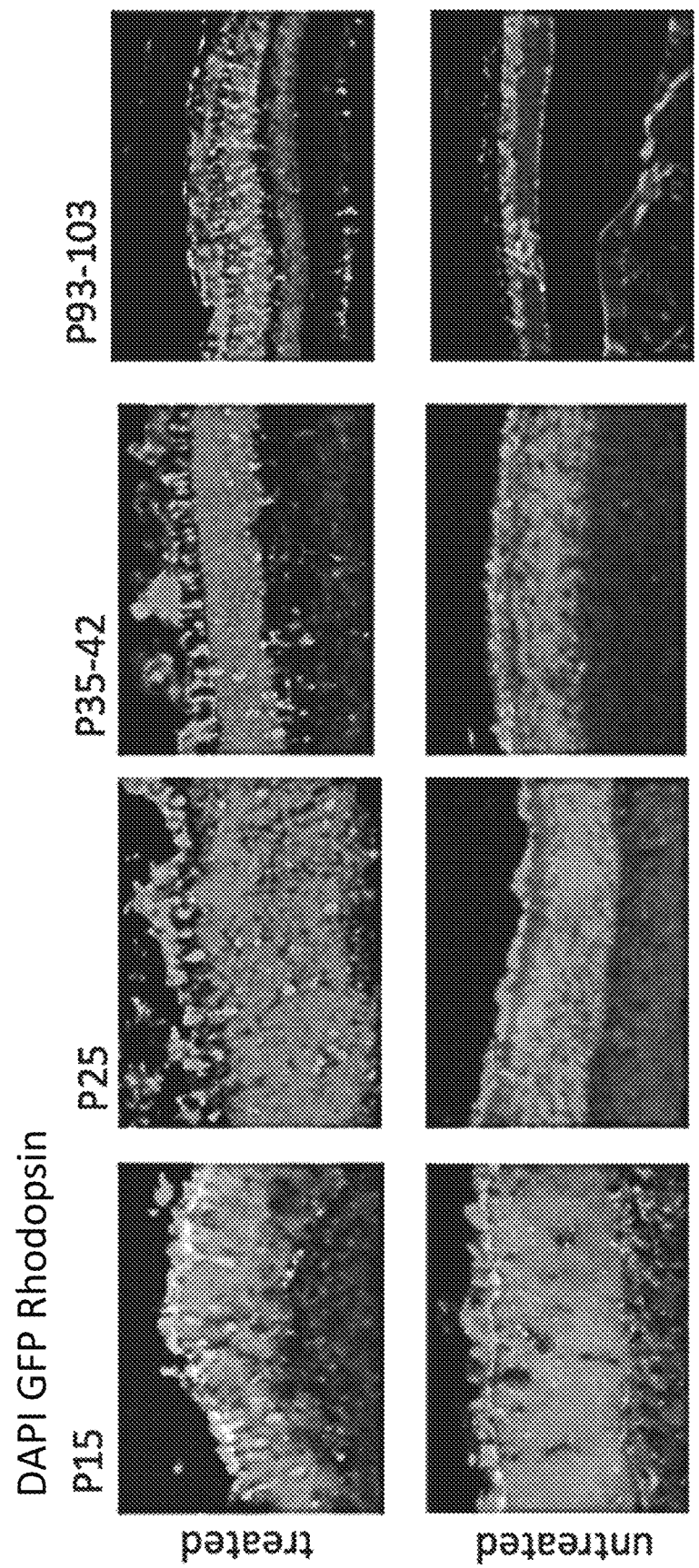
FIG. 5A provides result of immunofluorescence shows that rhodopsin persists in the treated (but not control untreated) photoreceptors through the 3 month timepoint. Occasional photoreceptor cells are eGFP-positive (region of injection identified through co-injection with AAV7m8.eGFP).
Figure 5B:
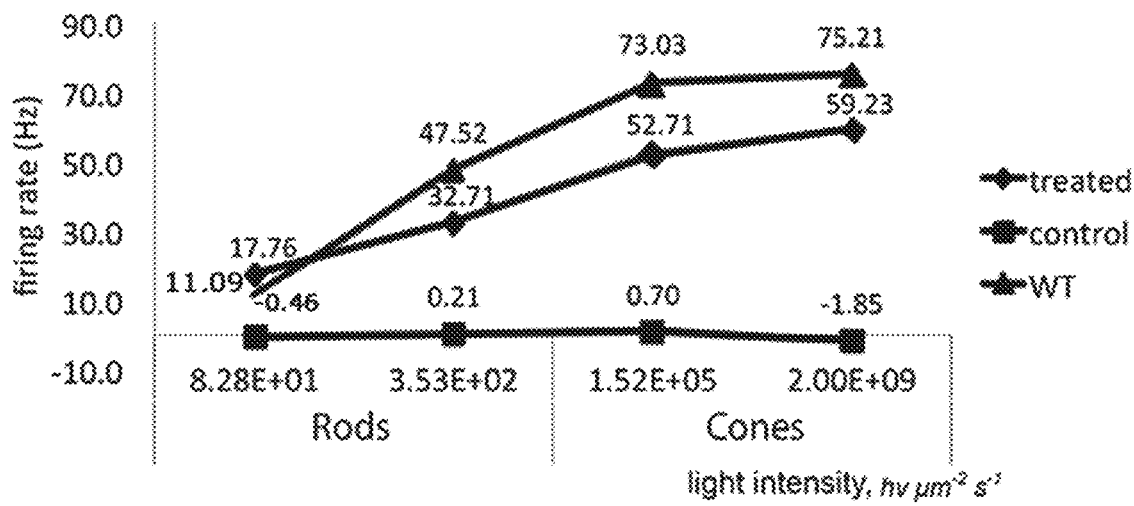
FIGS. 5B-5D provide Multi-electrode array (MEA) responses from Lca5gt/gt AAV7m8.hopt-LCA5-treated rods and cones are similar to those of wild type (WT) retinas. (B) Response amplitude (difference in firing rates before and after flash onset) vs. flash intensity data measured from per flash averaged traces (not shown). Responses from treated retinas are as high as 70% of the response from WT retina; there is minimal to abolished response from untreated retina. (C) Response amplitudes from retinas of panel A for the 1st and 2nd intensity series runs (before/during and after brightest exposures at the end of the 1st run, during each intensity series run stimulation series intensity was increased from scotopic to the brightest photopic values in −0.5 log increments) (D) Amplitudes of transient ON-(difference in firing rates before and after flash onset), sustained ON- (difference before flash onset and offset) and OFF-responses (difference before and after flash offset) as functions of the flash intensity for the 1st and 2nd intensity series runs. Shaded areas represent range of WT responses (4 retinas, MEAN±STD), line-only traces give averaged WT response amplitudes. Horizontal arrows illustrate rightward shift in sensitivity caused by exposure to the brightest flashes at the end of the 1st intensity series run. Treated Lca5gt/gt s and WT retinas show similar response/intensity dependencies before and after bleaching, while untreated Lca5gt/gt. retina responses are flattened. Circles connected by lines represent treated LCA5gt/gt. Triangles connected by lines represent control LCA5gt/gt.
Figure 5C:
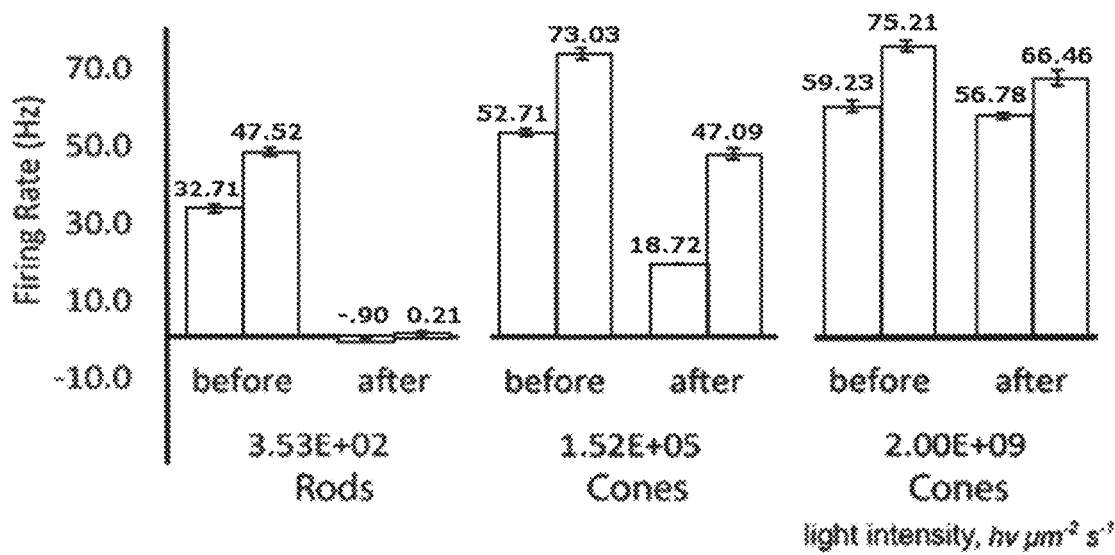
Figure 5D:
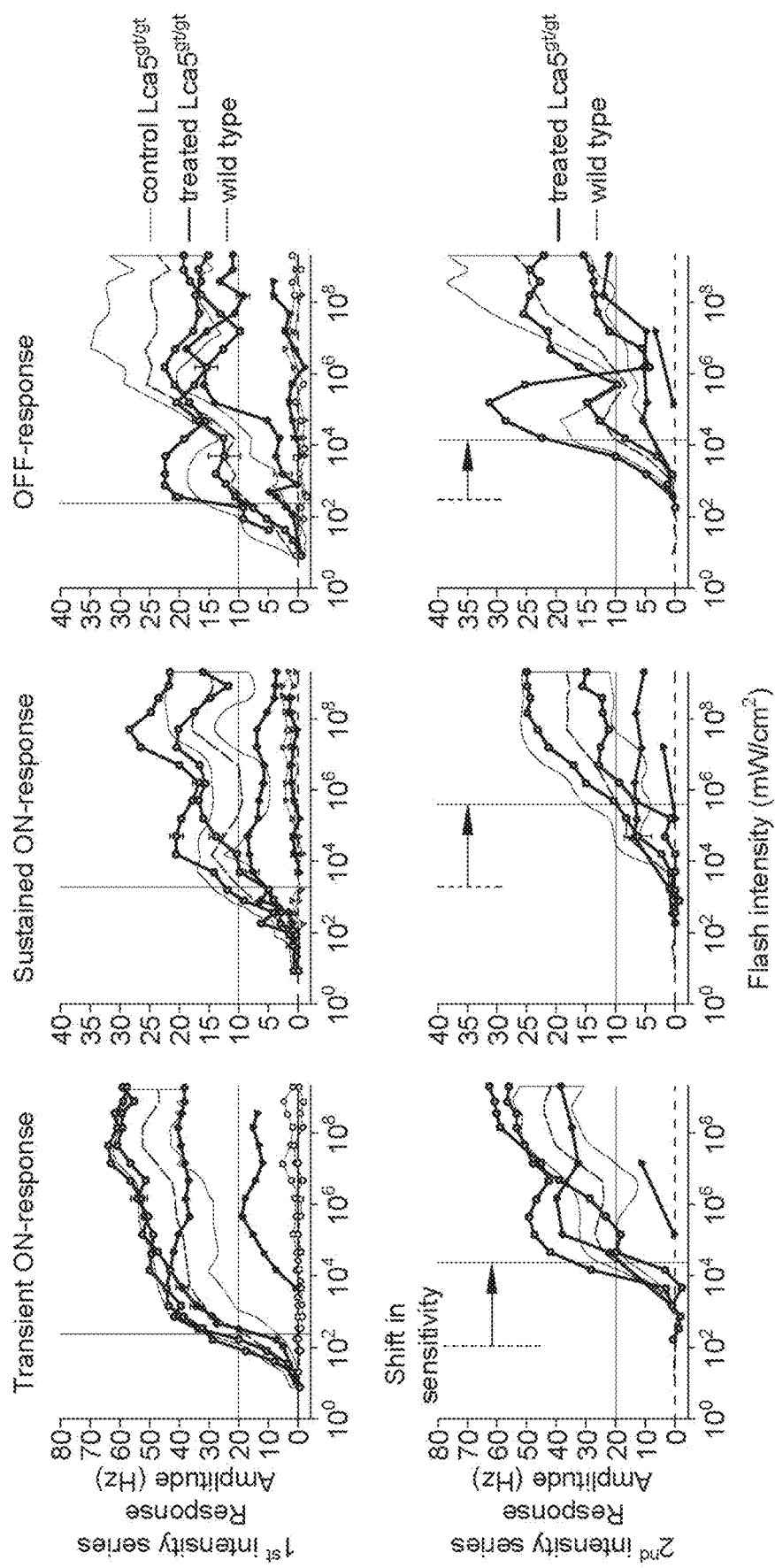
Figure 9:
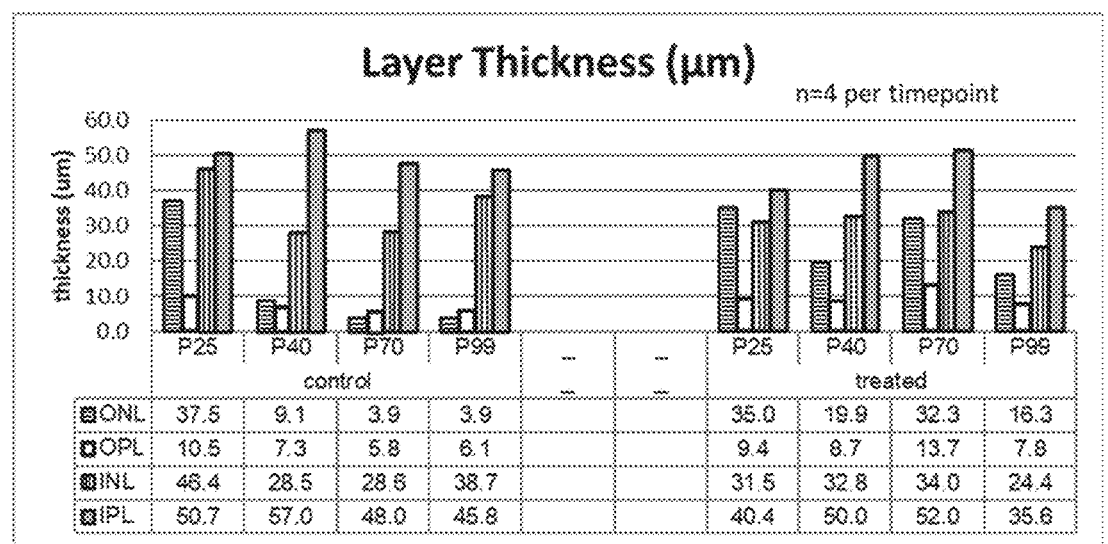
FIG. 9 is a table of the thickness of various retinal layers showing that outer nuclear layer (ONL) thickness remains thicker over at least 3 months in the treated (*) compared to the control retinas. There was not such a clear trend in the other retinal layers (outer plexiform layer, OPL; inner nuclear layer, INL, inner plexiform layer, IPL). For each time point, bars from left to right represent thicknesses of ONL, OPL, INL and IPL, respectively.
Figure 10:
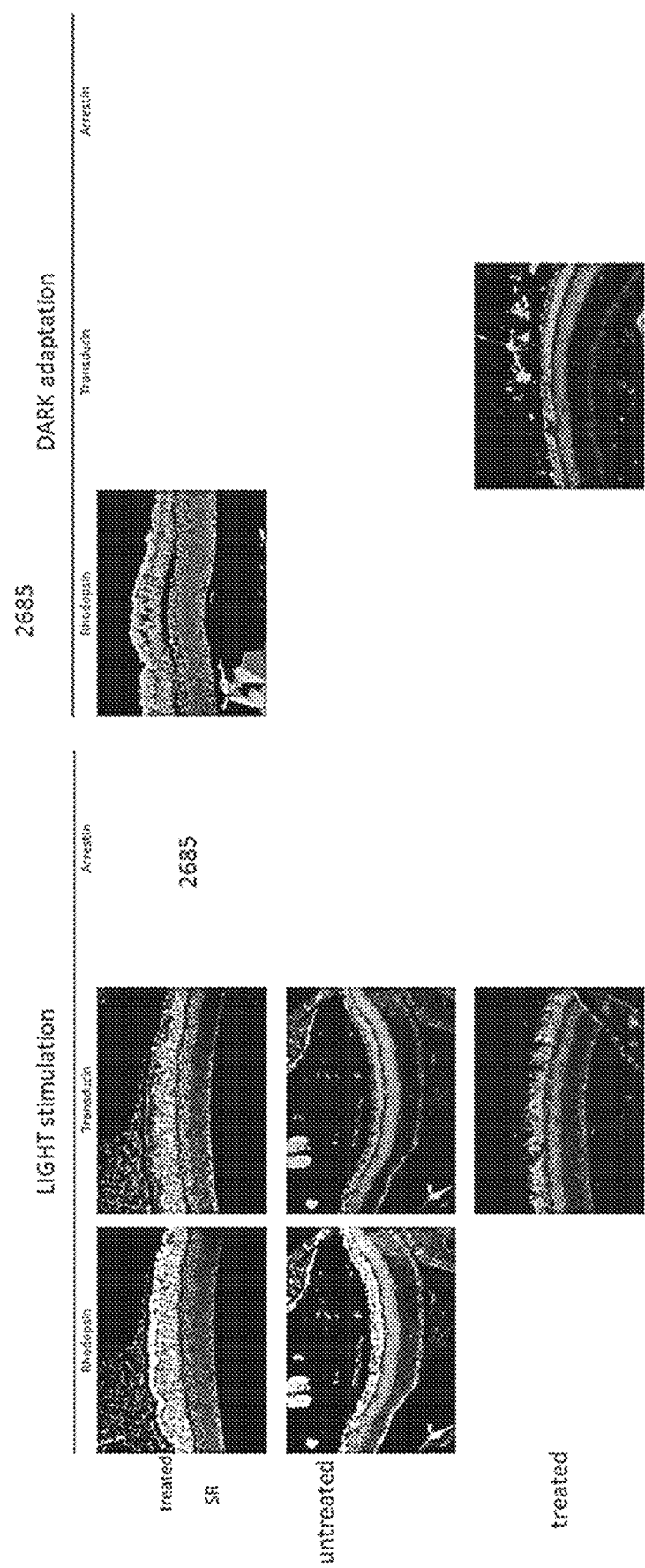
FIG. 10 provides results of Light-mediated changes in position of phototransduction-specific molecules after injection with AAV7m8.hopt.LCA5.
Figure 11A:
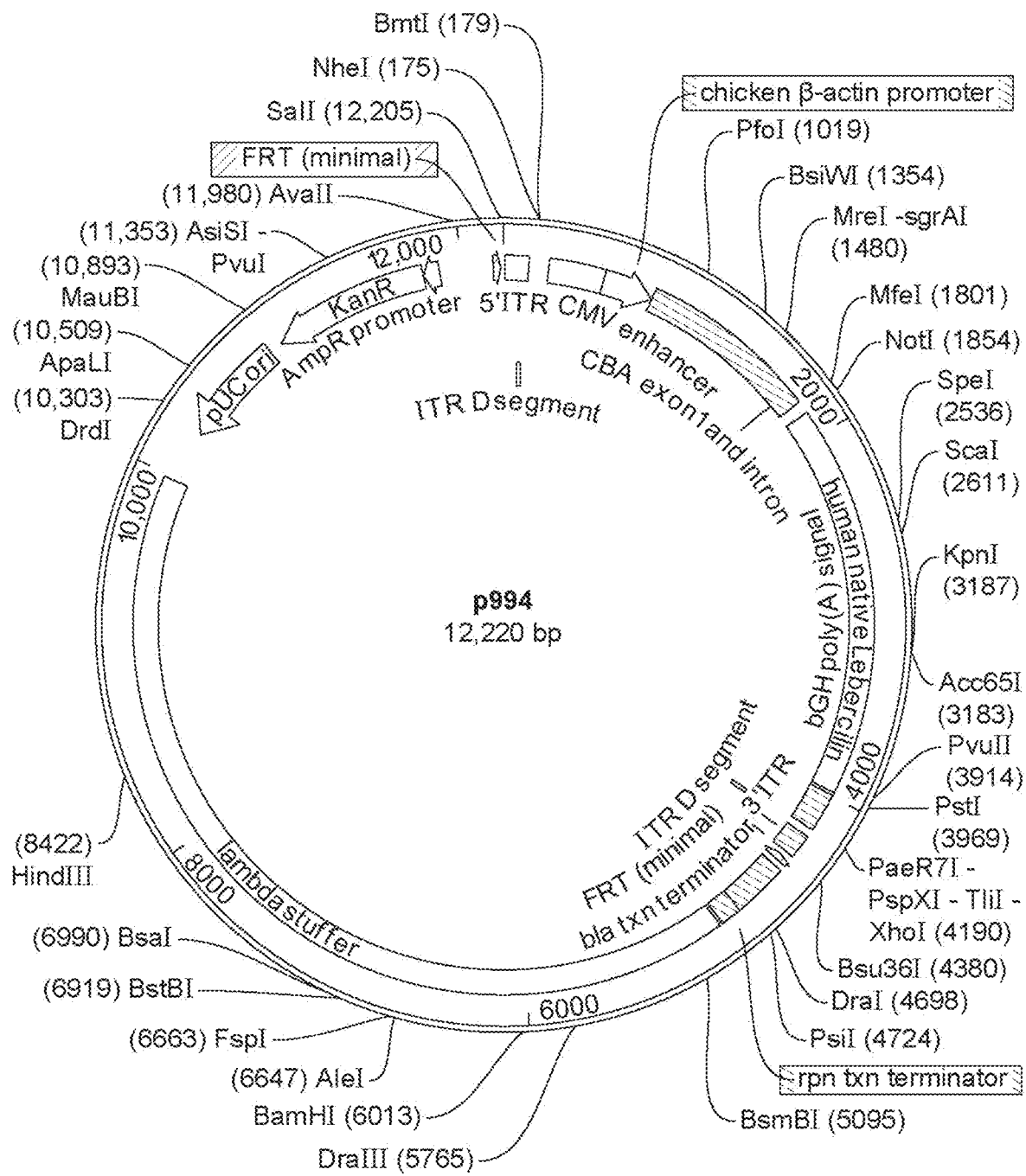

Evaluation of Lca5−/− mouse retinas injected on PN5 with AAV7m8.hLCA5 at 1-3 months post injection reveals increased thickness of the outer nuclear layer (FIG. 5A and FIG. 9). Immunofluorescence analysis revealed that Lebercilin co-localized with the base of tubulin-positive outer segments in AAV7m8.hOP.LCA5-treated Lca5−/− retinas (FIG. 1M). There were numerous TUNEL-positive cells in the first month of life in untreated Lca5−/− retinas, but significantly fewer in AAV7m8.hOPT.LCA5-treated retinas (FIGS. 6B and 6C). The number of TUNEL-positive cells decreased by the time the animals are 3 months of age (FIGS. 6D and 6E). The majority of cells that degenerate in the untreated Lca5−/− retina over time in control (untreated) retinas were photoreceptors, as shown by the fact that rhodopsin-positive cells were found only in the AAV-treated retinas (FIG. 6B). Immunofluorescence analysis confirmed this result (see DAPI-stained ONL), and showed increased rhodopsin persisting through the 3 month time point (FIG. 6D). There was evidence of light-mediated changes in position of phototransduction-specific molecules after injection with AAV7m8.hopt.LCA5 (FIG. 10).

Transmission electron microscopy (TEM) of AAV7m8.hopt.LCA5-treated retinas showed elaboration of outer segments complete with stacked outer segment disks, 9+0 microtubule arrays typical of primary cilia (FIG. 7B) and connecting cilia (FIG. 7). In contrast, untreated Lca5−/− retinas lacked both connecting cilia and outer segments. The untreated retinas lack outer segments and show massive degeneration of photoreceptors with only pyknotic nuclei and remnants of photoreceptor organelles. Only disorganized, degenerating photoreceptor cell bodies were present in control untreated or sham-injected retinas.

Light stimulation of dark-adapted adult Lca5gt/gt retinas treated at PN5 with AAV7m8.hopt-LCA5 resulted into normal translocation patterns of phototransduction proteins into outer segments. Arrestin translocates properly after light exposure in AAV7m8.hopt-LCA5-treated retinas. Such activity cannot be assessed in the control retinas due to the degeneration of IS/OS. The data reflect restoration of the intraflagellar transport defect in the mouse retina after delivery of the wild type (WT) hLCA5 cDNA.

Development of proof-of-concept of gene augmentation therapy in the Lca5−/− mouse model entails several challenges: 1) Because retinal degenerative changes progress rapidly and early in life, intervention must be carried out in neonatal mice; 2) Since this is a photoreceptor-specific disease, recombinant AAV vectors must be employed that target photoreceptors efficiently. The AAV2 vector that has been used extensively in animal and human studies to target RPE cells, does not target photoreceptors as efficiently as other AAVs.(23, 24). Ideally, reagents should be used that could ultimately be used in human clinical trials; and 3) Outcome measures must be developed that reflect improvements in retinal and visual function, levels that are so low at baseline that they are difficult to measure. Here a recombinant AAV designed by directed evolution, AAV7m8,(25)

was used to test for efficacy after delivery of the native human Lebercilin-encoding cDNA. This vector has been shown by others to efficiently target photoreceptors after intra-vitreal delivery.(25-27). By using AAV7m8 to deliver the hLCA5 cDNA to the diseased photoreceptors early in life, gene augmentation therapy resulted in both structural and functional improvement of the Lca5−/− mouse retina and of vision.

In Examples 3 and 4, it was demonstrated that AAV7m8-mediated gene augmentation therapy in the Lca5−/− mouse rescued retinal and visual function and also retinal structure.

The efficacy reported in the present example included the improved ability of this model to navigate using visual cues, restoration of rod and cone photoreceptor responses as shown by Multi-electrode array (MEA), a reduction in apoptotic cell death (and thus preservation of photoreceptors), and presence of cell biologic and physical features characteristic of normally functioning photoreceptors, such as presence of rhodopsin in the outer retina and development of normal-appearing outer segments, with stacked outer segment discs. MEA results showed that given successful injection and enough post injection time to express the transgenic protein and restore function of rod/cone outer segments, gene therapy restored degenerated retinal cells to a state nearly indistinguishable from the WT conditions. Further, delivery of wildtype LCA5 protected against degeneration of photoreceptors. While untreated Lca5−/− retina was reduced to a single row of sickly photoreceptors by 3 months of age, the AAV-treated regions had a thick outer nuclear later complete with inner and outer segments. The gains persisted at least 3 months—a very significant finding especially considering that by this age, there were no remaining photoreceptors in the untreated Lca5−/− mouse retina. The data suggested that a similar gene augmentation approach in humans as that used in the Lca5−/− mouse could result in improved vision.

Example 5: Human Studies: Pupillary Light Reflex Testing

Testing was carried out after obtaining written informed consent on an IRB approved protocol (#815348). Pupil responses were recorded simultaneously in both eyes with a Procyon P3000 pupillometer and PupilFit6 software (Monmouthshire, UK). Pupillary responses to light were recorded after presentation of 10 lux green light stimuli to the right eye for 0.2 seconds followed by dark intervals. An infrared sensitive camera that captures video images at 25 frames per second, allowing the pupil diameter of both eyes to be measured every 40 ms.

Figure 8:
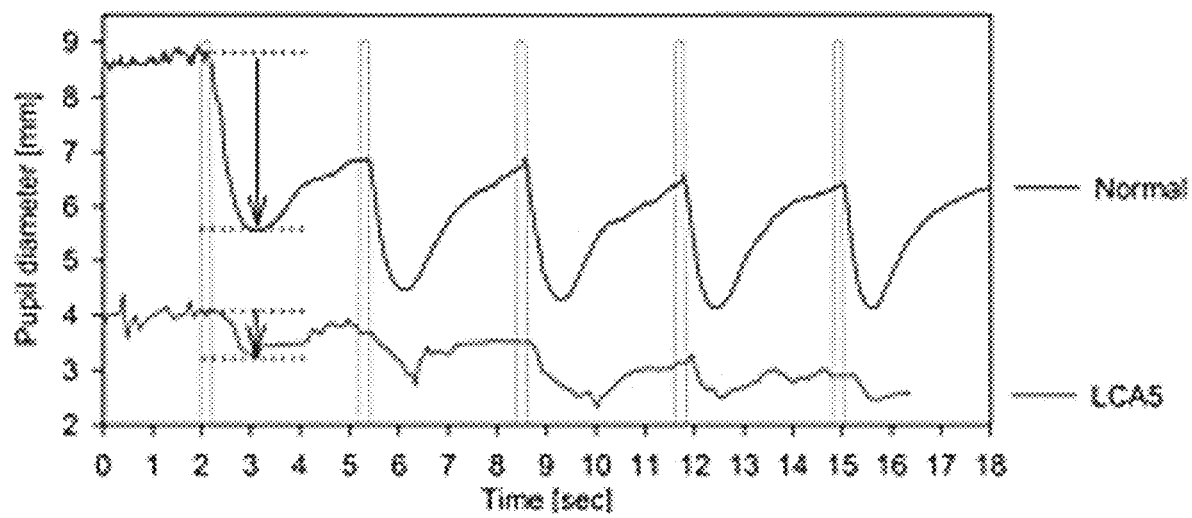
FIG. 8 shows result of Pupillary Light Responses of one retina of an adult man with LCA5 (top line) having similar temporal characteristics as those of an age-comparable normal-sighted man (bottom line). The amplitude of constriction was reduced in the LCA5 patient compared to the normal individual.

Pupillary light reflex testing was carried out to determine whether there was any evidence of function in the residual photoreceptors present in an adult with homozygous LCA5 mutations. As shown in FIG. 8, pupillary light reflexes were present in this individual with the same temporal sequence as those in a normal-sighted individual. However, the amplitudes of response were diminished considerably compared to the normal-sighted individual.

Example 6: Induced Pluripotent Stem Cell (iPSC) Models of LCA5

Figure 12A:
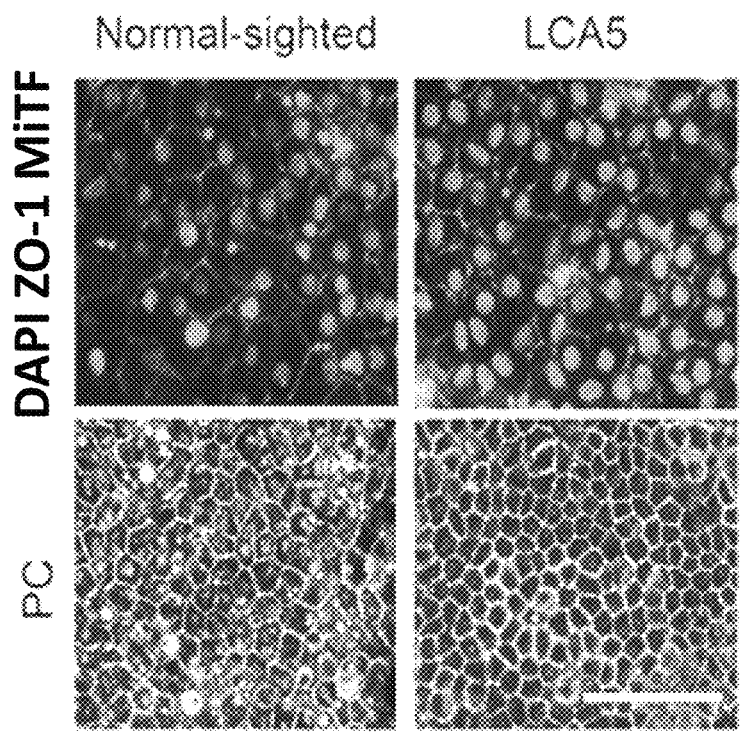
FIGS. 12A-12F demonstrate cilia phenotype rescued in homozygous human LCA5 p.(Q279*) iPSC-RPE after treatment with AAV7m8.hopt-LCA5. (A) Confocal images show hexagonal morphology of mature RPE cells along with the immunofluorescently detectable RPE markers; ZO-1 and MITF. Phase contrast (PC) images display the architecture of iPSC-RPE cultures of RPE derived from both the normal-sighted person and LCA5 patient; (B) Quantitative real-time PCR (qRT-PCR) of LCA5 mRNA expression in normal-sighted control RPEs and LCA5 patient-derived RPEs. GAPDH is used to normalize expression levels. (C) Western blot analyses show endogenous (*) Lebercilin protein in normal-sighted control cells that are untreated ("-") or treated with AAV7m8.eGFP ("G"). There is no endogenous lebercilin in untreated or AAV7m8.GFP-treated LCA5-affected cells. There are robust levels of lebercilin after infection of cells from both normal-sighted and LCA5 individuals with AAV7m8.LCA5 ("L") Immunofluorescence analyses show presence of Arl13b-positive primary cilia in normal-sighted (D) and LCA5-derived (E) iPSC-RPE. Lebercilin is present in normal-sighted control and AAV7m8.LCA5-treated (but not AAV7m8.eGFP-treated) LCA5-affected cells. (F) Quantitative analysis of number of cilia per cell in normal-sighted- vs. LCA5-iPSC-RPE shows rescue effect of cilia formation after treatment of LCA5-iPSC-RPE cells with AAV7m8.LCA5 (but not with AAV7m8.eGFP).
Figure 12B:
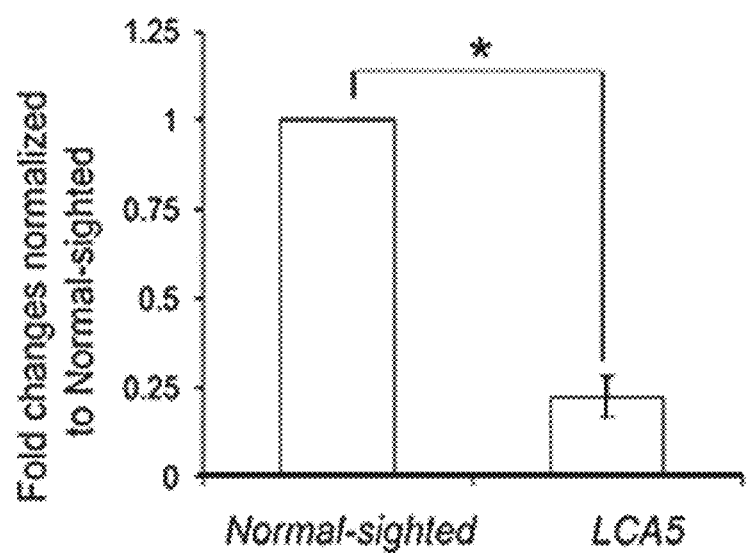
Figure 12C:
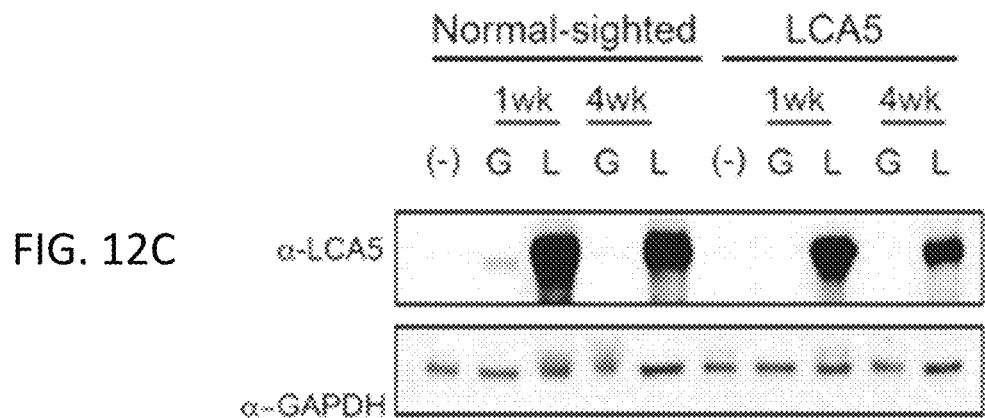
Figure 12D:
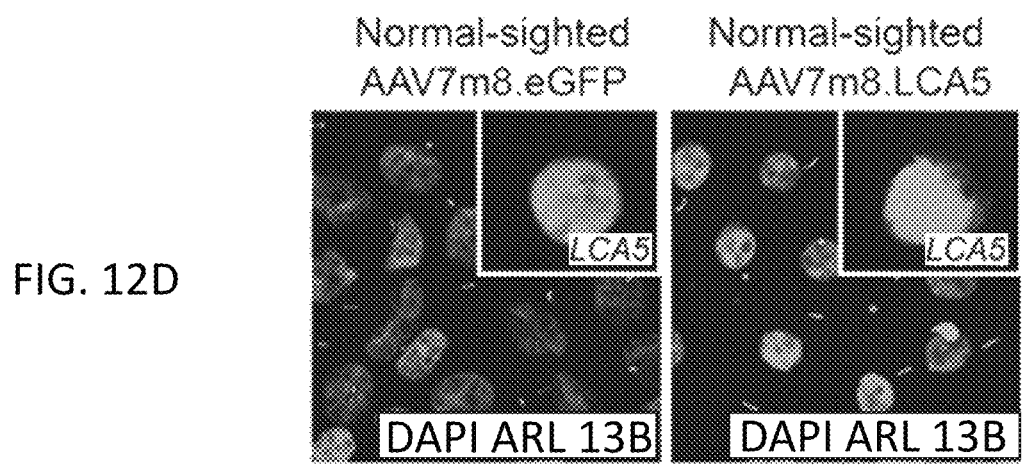
Figure 12E:
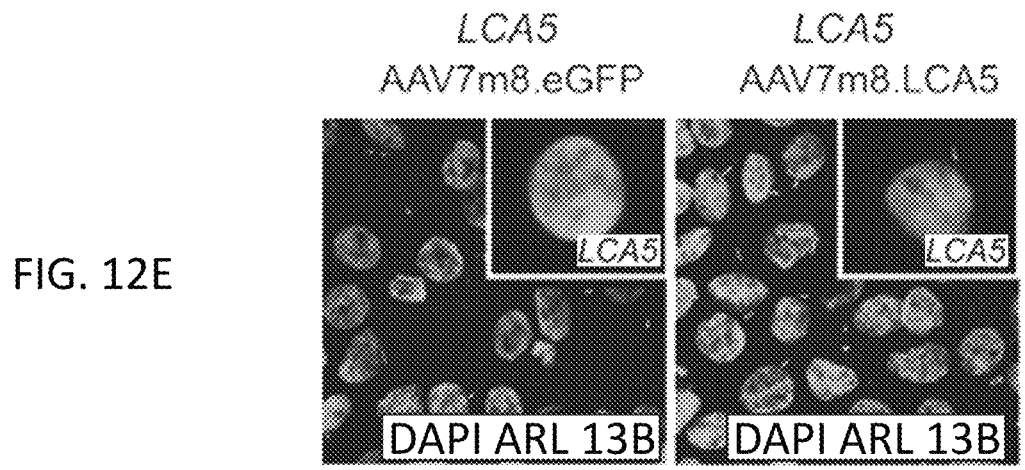
Figure 12F:
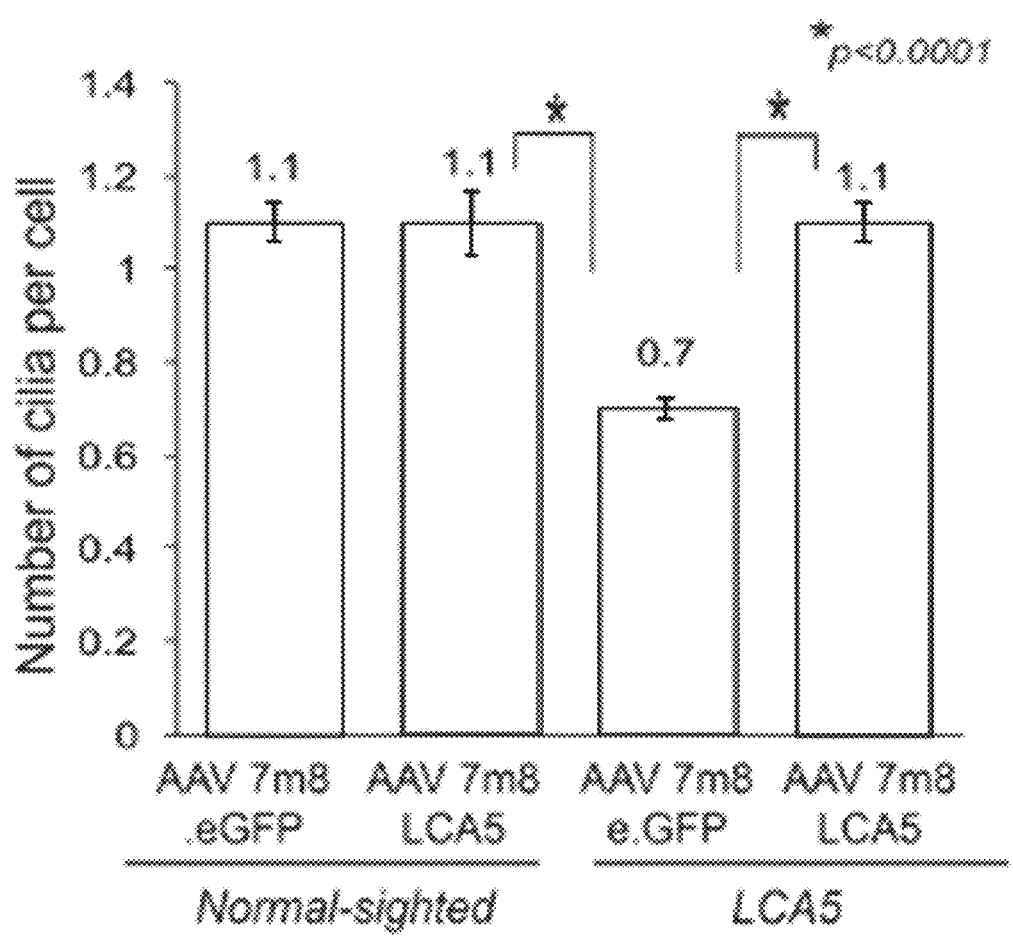

To aid in translating the mouse rescue studies to human, we studied human induced pluripotent stem cell (iPSC) lines that were generated for study from individuals with normal vision and those affected with LCA due to LCA5 mutations. Recently, iPSC-derived retinal pigmented epithelium (RPE) has been shown to recapitulate the functional phenotype of polarized epithelium, with secretion, gene expression and maturation characteristics comparative to fetal and adult RPEs 29. These cells show great promise for understanding disease mechanisms associated with defects in cilia biology 30, 31. Here, we differentiated iPSCs into RPE cells (FIG. 12A), a process which allowed evaluation of ciliated cells in a shorter timespan and more efficiently than if neuronal/photoreceptor cells had been generated (Figure S12). We evaluated LCA5 gene expression and show that LCA5 mRNA is expressed in unaffected iPSC-derived RPEs and the level of expression of LCA5 in LCA patient RPEs is significantly reduced compared to controls (FIG. 12B). When ciliary distribution was measured, there were significantly fewer cilia present on the iPSC-RPE derived from the LCA5 patient than on the RPEs from the normal-sighted individual (FIG. 12D-E). Treatment of the LCA5-iPSC-RPE with AAV7m8.hopt-LCA5 led to production of lebercilin protein (FIG. 12C) and resulted in comparable cilia numbers in the AAV7m8.LCA5 treated and normal-sighted individual RPE cells (FIG. 12D-F).

Peripheral blood monocytes (PBMCs) were collected after signed informed consent (IRB approved protocol #808828) from two different probands with LCA5 mutations. One proband, JB605, was a compound heterozygote for LCA5 Gln279Stop CAG>TAG het and Lys172del4ctcAAAG het; The other, JB590, was homozygous for LCA5 c.835C>T p.Q279X. The wildtype cells were from individual PBWT4.6. Induced pluripotent stem cell lines were generated from each of the three individuals. PBMCs were cultured in expansion media consisting of QBSF-60 (Invitrogen, Carlsbad, Calif.) media supplemented with cytokines and hormone. The media was replenished every 2-3 days for a period of 7-9 days until the cells entered a stage of exponential growth.

For reprogramming, expanded PBMCs were transduced with the rTTA lentivirus and doxycycline inducible "stem cell cassette" in the lentivirus vector delivering OCT4, KLF4, SOX2, and cMyc cDNA and microRNA 302/367 cluster driven by the TetO/CMV promoter. Cells were grown in expansion media supplemented with polybrene (5 µg/ml; Sigma-Aldrich, St. Louis, Mo.). The cells were incubated for 20-24 h at 37° C. Infected cells were then washed, and placed in expansion media supplemented with 1 µg/ml of doxycycline (DOX). After 48 h, cells were resuspended in Iscove's modified Dolbecco's medium (IMDM) with 10% fetal bovine serum(FBS), penicillin/streptomycin, L-glutamine, beta-mercaptoethanol, nonessential amino acids, 4 ng/ml of basic fibroblast growth factor (bFGF), and 1 µg/ml of DOX (Sigma-Aldrich, St. Louis, Mo.) then moved onto matrigel-coated (BD Biosciences, San Jose, Calif.) mouse embryonic fibroblast plates (MEF plates). Cells remained in this media for 10 days, then were transferred to human embryonic stem cell (hESC) media (DMEM/F12, 20% knockout serum replacement, nonessential amino acid, 4 ng/ml bFGF, 0.001% beta-mercaptoethanol, penicillin/streptomycin, L-glutamine, and 1 µg/ml of DOX (Invitrogen, Carlsbad, Calif.). After 4 weeks, iPSC-like colonies were manually picked and expanded on matrigelcoated MEF plates for 6 passages, then transitioned to 0.1% gelatin-coated MEF plates for a minimum of 15 passages. Characterization of iPSCs was based on surface antigen expression measured by flow cytometry using antibodies against SSEA3+, SSEA4+, TRA-1-60, and TRA-1-81 (Biolegend, San Diego, Calif.), and RT-qPCR analysis included pluripotency expression markers: DMNT3B, ABCG2, REX1, OCT4, SOX2, NANOG, cMYC, KLF4. Karyotyping of iPSCs was carried out by G banding to produce a visible karyotype. The ability of the cells to differentiate into multiple different lineages was carried out using a PCR germ layer assay (Qiagen. Germantown, Md., USA).

The characterized iPSCs were differentiated into RPE by activation of the Wnt signaling pathway, inhibition of the fibroblast growth factor signaling pathway, and inhibition of the Rho-associated, coiled-coil containing protein kinase signaling pathway. Expanded pigmented cells were purified by plate adhesion on 8-chamber slides on geltrex matrix. Enriched cells were cultured until they developed a cobblestone appearance with cuboidal shape. The characteristics of iPS-RPE were confirmed by gene expression, immunocytochemistry, and microscopy. Cilia lengths were measured after fixing and staining for ARL13B and Pericentrin. Cilia lengths were measured in three dimensions using custom-designed software designed by the Wistar Imaging Facility (Wistar Institute, Philadelphia, Pa.)

Cilia are evaluated in the control and LCA5 iPSC-RPE cell lines for density and length. There are significantly fewer cilia present on the RPE cells derived from the two LCA5 patients than on the wildtype cell line. In addition, the cilia on the LCA5-derived lines are significantly shorter than those in the wildtype cells.

It was previously observed that LCA5 patients can retain photoreceptors including in the foveal outer nuclear layer, for up to 3 decades.(21, 29). Since successful gene therapy requires that the cells be present (even if they are sickly), LCA5 photoreceptors may be amenable to treatment. The fact that the instant examples demonstrated that retained photoreceptors in an adult with LCA5 showed a similar temporal pattern of light responsiveness (albeit reduced amplitude) as photoreceptors from a normal-sighted individual is encouraging. These results further supported the fact that the residual photoreceptors in these abnormal retinas were viable despite their structural and functional deficits. Further, the cilia from the LCA patient-derived iPSC-RPE cells were significantly shorter than those from the wildtype control cells. The fact that the ciliary defect in photoreceptors in the Lca5-/- mouse could be in the corrected by gene augmentation therapy, suggested that it might ameliorate the ciliary defect present in humans with this condition. Studies aiming to correct the ciliary defect in vitro in iPSC-derived RPE cells are currently in process.

Gene augmentation therapy in humans with LCA5 is under investigation to test for safety and efficacy thereof. Besides the need to develop appropriate outcome measures for this severe blinding condition, the instant application provided solutions to several problems in planning human clinical trials, including developing constraints for achieving rescue? In the Lca5-/- mouse, the examples demonstrated rescue in both neonatal (PN5) and juvenile (PN15) mice. An intervention was not observed at later stages of the disease because of the early photoreceptor loss in this mouse model. The abnormalities of development in the mouse model (coinciding with degeneration of photoreceptors) suggested that there were developmental components of the disease. There were likely developmental components in the human condition as well. As mentioned above, in humans with LCA5, there is evidence of persistence of some macular photoreceptors even in adults.(21) Investigation is undergoing to determine how to improve the function of those photoreceptors as well as to determine whether the visual pathways can be resuscitated in humans with LCA5 based on the fact that there has been success in resuscitating cortical vision in humans enrolled in RPE65 gene therapy clinical trials even after suffering for decades with limited vision.(4, 30, 31)

Example 7: Genotyping of the Lca5-/- Mouse

Genomic DNA was PCR-amplified using the following oligos: LCA-13F6 (common F) GCCTGTTCCTGCTTGCTTAC (enclosed as SEQ ID NO: 13); LCA-13R2 (WT Reverse) TGCTTTC-CAAAGTAAGCACAAA (enclosed as SEQ ID NO: 14) en2.8r (mutant Reverse) CCTGGCCTCCA-GACAAGTAG (enclosed as SEQ ID NO: 15). PCR was run for 35 cycles with an annealing temperature of 50° C. and an extension step at 72° C. The predicted products are 353 bp (wildtype) and 439 bp (Lca5-/-).

Example 8: Intravitreal Injection of AAV7m8.hLCA5 Restores Photoreceptor Function in Lca5-/- Mice to Nearly WT Levels Early onset vision loss results from mutations in LCA5, a gene which encodes Lebercilin, a protein critical for the health and function of photoreceptors. Because there can be relative preservation of photoreceptors, LCA5 disease may be amenable to gene augmentation therapy. The possibility that gene augmentation therapy using intravitreal delivery of AAV7m8.CMV/CBA.hLCA5 restores photoreceptor and retinal function using multi electrode array (MEA) in an Lca5 mouse model (Lca5-/-) was tested.

Postnatal day 5 Lca5-/- mice were injected intravitreally with AAV7m8.CMV/CBA.hLCA5 (approximately $9.87 \times 10^{10}$ vg/eye) mixed with 5% (v/v) AAV7m8.CBA.GFP. Contralateral eyes were uninjected and used as negative control. 3 months after the intervention and under light adapted conditions, Lca5-/- retinas were dissected under red light and mounted ganglion cell side down in the perforated MEA chamber. The same dissection and preparation procedure was done for untreated age-matched wild type mice (C57Bl/6) as a positive control. Presence of GFP confirmed exposure of photoreceptors to the AAV. Calibrated full field flashes of 455 nm light in the scotopic and photopic intensity ranges (10 2 s flashes at 0.1 Hz or 400 50 ms flashes at 4 Hz) were used for light stimulation (blue light was used to maximize chances of response detection by targeting both M- and S-cones, efficiency of M- and S-cone excitation should be around 40% and 0.2% correspondingly). Data were analyzed using custom code in Matlab, spike sorting was performed using Pllexon Offline Sorting.

After three months, among eyes with intact retina, 3 out of 5 demonstrated strong light responses, 1 showed median responses and 1 showed minimal responses when tested using MEA recording. In 3 retinas with strong responses, light responses become detectable in the scotopic range (from 42 to 112 photons$\times s^{-1} \times \mu m^{-2}$) and strong responses were observed up to the brightest photopic intensities of $2.00 \times 10^9$ photons$\times s^{-1} \times \mu m^{-2}$. Meanwhile retinas from uninjected contralateral eye showed minimal to abolished responses. As expected for rod/cone driven responses, after exposures to the brightest stimulation series, scotopic responses disappeared but responses in the photopic range were not significantly affected. Response kinetics and sensitivity were very similar to those observed from the 5 WT retinas tested under identical protocol (sensitivity of the treated retinas being slightly lower compared to the most sensitive WT retinas for which dimmest flashes producing rod-driven responses were in the 8-21 photons$\times s^{-1} \times \mu m^{-2}$ range). One of the treated retinas tested two months after injection demonstrated lower light sensitivity (responses started at the photopic intensity of $1.52 \times 10^4$ photons$\times$s$^{-1}\times$μm$^{-2}$) and responses were mostly gone after brightest exposures. This may indicates that 3 mos are required for sufficient expression of the targeted protein and generation of functional rod/cone outer segments. All ganglion cell types identifiable in the WT retinas under full field stimulation (ON-, OFF- and ON/OFF-types) were detected in the Lca5-/- treated retinas after spike sorting. As well as WT retinas, treated Lca5-/- retinas were responsive to 4 Hz flicker stimulation in the intensity range of $3.53 \times 10^2$-$2.00 \times 10^9$ photons$\times$s$^{-1}\times$μm$^{-2}$. Only one of the 7 control untreated Lca5-/- retinas demonstrated very weak light responses at the bright photopic stimuli likely indicative of the remaining cone function. All untreated Lca5-/- retinas demonstrated slow melanopsin driven responses at brighter intensities which were absent in the light sensitive treated Lca5-/- retinas.

Two of the treated Lca5-/- retinas had signs of post-injection injury and did not show light responses despite strong spontaneous firing. One treated retina did not show obvious signs of post injection injury but demonstrated only very weak light responses at the brighter end of stimulation intensities ($8.07 \times 10^8$ photons$\times$s$^{-1}\times$μm$^{-2}$ and above) which might be indicative of the low expression of the targeted protein and/or of the weak remaining cone function.

Given successful injection and enough post injection time to express targeted protein and restore function of rod/cone outer segments, gene therapy restores degenerated retinal cells to a state nearly indistinguishable from the WT conditions.

In summary, LCA itself is one of the most severe retinal degenerative diseases, and LCA5 is one of the most severe subtypes within this category. Often LCA5 patients enjoy only light perception early in life, and it is difficult even to carry out structural studies and specialized tests of visual function in these ultra-low vision subjects due to nystagmus. Thus, this disease is considered difficult to approach. However, the phenotype of the Lca5-/- mouse reflects many of the clinical findings in humans with LCA5 mutations. The rescue data in the Lca5-/- mouse provide hope that a similar gene augmentation approach in humans could result in improved vision. In parallel with the preclinical studies leading to a human clinical trial, it is important to develop the methodology with which to accurately measure the structure and function of the LCA5 retina so that the effects of gene therapy in a clinical trial can be captured reliably and accurately. Not only could such studies and a gene therapy clinical trial lead to a treatment for this devastating condition, but they could also provide the framework for measuring the effects of intervention in other severe, early onset blinding conditions.

Example 9: Preliminary Analysis of LCA5 Disease in Humans

PLR testing was carried out to determine whether there was any evidence of function in the residual photoreceptors present in human adult with homozygous LCA5 mutations. As shown in Figure S11, PLRs were present in this individual with the same temporal sequence as those in a normal-sighted individual. However, the amplitudes of response were diminished considerably compared to the normal-sighted individual.

Example 10: Loss of Lebercilin Causes Dysregulation of RPE Maturation and Ciliary Function in Cellular and Animal Models The pathological changes occurring in the visual system in Leber Congenital Amaurosis 5 (LCA5), a disease caused by loss of expression of the Lebercilin-encoding LCA5 gene, were explored. Previous studies elucidated the detrimental effect of Lebercilin deficiency on the neuroretina, and specifically on photoreceptors. This study aimed to further elucidate the pathogenic mechanisms leading to LCA5 by focusing on the contribution of normal LCA5 expression to the development and function of the retinal pigmented epithelium (RPE).

Two independent experimental paradigms were implemented: One used generation of RPE cells from induced pluripotent stem cells (iPSCs) from both normal sighted individuals and those with LCA5. RPE cell morphology, pigmentation, cell-specific markers and characteristics of the primary cilia were measured. The second approach evaluated studies of the retinas of wildtype mice compared to those of a murine model for LCA5 deficiency (LCA5gt/gt mice). The spacial-temporal differentiation patterns were characterized in order to delineate the degenerative vs developmental changes occurring in the visual system caused by lack of LCA5 protein.

The results demonstrate that LCA5 deficiency in both human RPE cell models and in the RPE of living mice causes profound alterations in the development of those cells. Through gene expression analysis, we identified the dysregulation of key proteins responsible for ciliogenesis and intraflagellar transport, pigmentation, and developmental WNT signaling pathway. Immunostaining also identified differences in the epithelial barrier consistent with altered maturation due to loss of LCA5 protein function.

This work reveals the detrimental effect of LCA5 suppression in RPE through alteration of processes such as pigmentation, potentially due to an inhibition of intracellular trafficking or indirectly by delaying the maturation progression of these cells. In this study, we introduce the potential primary role of RPE cells in retinal pathology traditionally attributed to photoreceptor malfunction.

All patents, patent publications, and other publications cited in this specification are incorporated herein by reference, as well as the proiority applications, US Provisional Patent Application No. 62/465,649, filed Mar. 1, 2017, and U.S. Provisional Patent Application No. 62/469,642, filed Mar. 10, 2017. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

| SEQ ID NO | Protein or Nucleic Acid Sequence | Description |
| --- | --- | --- |
| 1 | Protein | Lebercilin |
| 2 | Nucleic Acid | native LCA5 |
| 3 | Nucleic Acid | codon optimized LCA5 |
| 4 | Nucleic Acid | NM_181714.3 (transcript variant 1) |
| 5 | Nucleic Acid | NM_001122769.2 (transcript variant 2) |
| 6 | Nucleic Acid | XM_011535504.1 (transcript variant X1) |
| 7 | Nucleic Acid | XM_005248665.4 (transcript variant X2) |
| 8 | Nucleic Acid | production plasmid |

-continued

| SEQ ID NO | Protein or Nucleic Acid Sequence | Description |
|---|---|---|
| 9 | Nucleic Acid | production plasmid |
| 10 | Nucleic Acid | promoter |
| 11 | Nucleic Acid | AAV7m8 capsid |
| 12 | Protein | AAV7m8 capsid |
| 13 | Nucleic Acid | LCA-13F6 primer |
| 14 | Nucleic Acid | LCA-13R2 primer |
| 15 | Nucleic Acid | en2.8r primer |

Sequence Listing Free Text

The following information is provided for sequences containing free text under numeric identifier <223>.

| SEQ ID NO: (containing free text) | Free text under <223> |
|---|---|
| 3 | <223> constructed sequence |
| 8 | <223> constructed sequence |
| 9 | <223> constructed sequence |
| 10 | <223> constructed sequence |
| 11 | <223> constructed sequence |
| 12 | <223> constructed sequence |
| 13 | <223> constructed sequence |
| 14 | <223> constructed sequence |
| 15 | <223> constructed sequence |

REFERENCES

1. Redmond T M, Yu S, Lee E, Bok D, Hamasaki D, Chen N, et al. Rpe65 is necessary for production of 11-cis-vitamin A in the retinal visual cycle. Nat Genet (1998) 20(4):344-51. PubMed PMID: 9843205.
2. Redmond T, Hamel C. Genetic analysis of RPE65: from human disease to mouse model. Methods in Enzymol (2000) 317:705-24.
3. Maguire A M, High K A, Auricchio A, Wright J F, Pierce E A, Testa F, et al. Age-dependent effects of RPE65 gene therapy for Leber's congenital amaurosis: a phase 1 dose-escalation trial. Lancet (2009) 374(9701):1597-605. PubMed PMID: 19854499.
4. Bennett J, Wellman J, Marshall K A, McCague S, Ashtari M, DiStefano-Pappas J, et al. Safety and durability of effect of contralateral-eye administration of AAV2 gene therapy in patients with childhood-onset blindness caused by RPE65 mutations: a follow-on phase 1 trial. Lancet (2016) 388(10045):661-72. doi: 10.1016/S0140-6736(16)30371-3. PubMed PMID: 27375040.
5. Jacobson S G, Cideciyan A V, Ratnakaram R, Heon E, Schwartz S B, Roman A J, et al. Gene Therapy for Leber Congenital Amaurosis Caused by RPE65 Mutations: Safety and Efficacy in 15 Children and Adults Followed Up to 3 Years. Arch Ophthalmol (2012) 130(1):9-24. Epub 2011/09/14. doi: archophthalmol.2011.298 [pii] 10.1001/archophthalmol.2011.298. PubMed PMID: 21911650.
6. Cideciyan A V, Jacobson S G, Beltran W A, Sumaroka A, Swider M, Iwabe S, et al. Human retinal gene therapy for Leber congenital amaurosis shows advancing retinal degeneration despite enduring visual improvement. Proc Natl Acad Sci USA (2013). Epub 2013/01/24. doi: 1218933110 [pii] 10.1073/pnas.1218933110. PubMed PMID: 23341635.
7. Bainbridge J W, Smith A J, Barker S S, Robbie S, Henderson R, Balaggan K, et al. Effect of gene therapy on visual function in Leber's congenital amaurosis. N Engl J Med (2008) 358(21):2231-9. PubMed PMID: 18441371.
8. Weleber R G, Pennesi M E, Wilson D J, Kaushal S, Erker L R, Jensen L, et al. Results at 2 Years after Gene Therapy for RPE65-Deficient Leber Congenital Amaurosis and Severe Early-Childhood-Onset Retinal Dystrophy. Ophthalmology (2016) 123(7):1606-20. doi: 10.1016/j.ophtha.2016.03.003. PubMed PMID: 27102010.
9. Banin E, Bandah-Rozenfeld D, Obolensky A, Cideciyan A V, Aleman T S, Marks-Ohana D, et al. Molecular anthropology meets genetic medicine to treat blindness in the north african jewish population: human gene therapy initiated in Israel. Hum Gene Ther (2010) 21(12):1749-57. Epub 2010/07/08. doi: 10.1089/hum.2010.047. PubMed PMID: 20604683.
10. Maguire A, Russell S, Bennett J, Chung D, Wellman J, High K, editors. Phase 3 trial of AAV2-hRPE65v2 (SPK-RPE65) to treat RPE65 mutation-associated inherited retinal dystrophies. American Academy of Ophthalmology Retina Subspecialty Day; 2015; Los Vegas, N V.
11. Russell S, Bennett J, High K, Chung D, Wellman J, Maguire A. Phase 3 trial of AAV2-hRPE65v2 (SPK-RPE65) to treat RPE65 mutation-associated inherited retinal dystrophies. Saudi Ophthalmologic Society (2016).
12. den Hollander A I, Koenekoop R K, Mohamed M D, Arts H H, Boldt K, Towns K V, et al. Mutations in LCA5, encoding the ciliary protein lebercilin, cause Leber congenital amaurosis. Nat Genet (2007) 39(7):889-95. Epub 2007/06/05. doi: ng2066 [pii] 10.1038/ng2066. PubMed PMID: 17546029.
13. Gerber S, Hanein S, Perrault I, Delphin N, Aboussair N, Leowski C, et al. Mutations in LCA5 are an uncommon cause of Leber congenital amaurosis (LCA) type II. Hum Mutat (2007) 28(12):1245. doi: 10.1002/humu.9513. PubMed PMID: 18000884.
14. Chen X, Sheng X, Sun X, Zhang Y, Jiang C, Li H, et al. Next-generation Sequencing Extends the Phenotypic Spectrum for LCA5 Mutations: Novel LCA5 Mutations in Cone Dystrophy. Sci Rep (2016) 6:24357. doi: 10.1038/srep24357. PubMed PMID: 27067258; PubMed Central PMCID: PMCPMC4828721.
15. Corton M, Avila-Fernandez A, Vallespin E, Lopez-Molina M I, Almoguera B, Martin-Garrido E, et al. Involvement of LCA5 in Leber congenital amaurosis and retinitis pigmentosa in the Spanish population. Ophthalmology (2014) 121(1):399-407. doi: 10.1016/j.ophtha.2013.08.028. PubMed PMID: 24144451.
16. Mackay D S, Borman A D, Sui R, van den Born L I, Berson E L, Ocaka L A, et al. Screening of a large cohort of leber congenital amaurosis and retinitis pigmentosa patients identifies novel LCA5 mutations and new genotype-phenotype correlations. Hum Mutat (2013) 34(11):1537-46. doi: 10.1002/humu.22398. PubMed PMID: 23946133; PubMed Central PMCID: PMCPMC4337959.
17. Vallespin E, Avila-Fernandez A, Almoguera B, Velez-Monsalve C, Cantalapiedra D, Garcia-Hoyos M, et al. Novel human pathological mutations. Gene symbol: LCA5. Disease: Leber congenital amaurosis. Hum Genet (2010) 127(4):487. PubMed PMID: 21488265.
18. Vallespin E, Avila-Fernandez A, Almoguera B, Cantalapiedra D, Garcia-Hoyos M, Riveiro-Alvarez R, et al. Novel human pathological mutations. Gene symbol:

LCA5. Disease: Leber Congenital Amaurosis (LCA). Hum Genet (2010) 127(1):118. PubMed PMID: 20108395.
19. Ahmad A, Daud S, Kakar N, Nurnberg G, Nurnberg P, Babar M E, et al. Identification of a novel LCA5 mutation in a Pakistani family with Leber congenital amaurosis and cataracts. Mol Vis (2011) 17:1940-5. PubMed PMID: 21850168; PubMed Central PMCID: PMCPMC3154126.
20. Seong M W, Kim S Y, Yu Y S, Hwang J M, Kim J Y, Park S S. LCA5, a rare genetic cause of leber congenital amaurosis in Koreans. Ophthalmic Genet (2009) 30(1): 54-5. doi: 10.1080/13816810802592567. PubMed PMID: 19172513.
21. Jacobson S G, Aleman T S, Cideciyan A V, Sumaroka A, Schwartz S B, Windsor E A, et al. Leber congenital amaurosis caused by Lebercilin (LCA5) mutation: retained photoreceptors adjacent to retinal disorganization. Mol Vis (2009) 15:1098-106. Epub 2009/06/09. doi: 116 [pii]. PubMed PMID: 19503738; PubMed Central PMCID: PMC2690955.
22. Boldt K, Mans D A, Won J, van Reeuwijk J, Vogt A, Kinkl N, et al. Disruption of intraflagellar protein transport in photoreceptor cilia causes Leber congenital amaurosis in humans and mice. J Clin Invest (2011) 121(6): 2169-80. Epub 2011/05/25. doi: 45627 [pii] 10.1172/JCI45627. PubMed PMID: 21606596; PubMed Central PMCID: PMC3104757.
23. Vandenberghe L, Bell P, Maguire A, Cearley C, Xiao R, Calcedo R, et al. Dosage Thresholds for AAV2 and AAV8 Photoreceptor Gene Therapy in Monkey. Sci Transl Med (2011) 3(88):88ra54. Epub 22 Jun. 2011.
24. Ramachandran P S, Lee V, Wei Z, Song J Y, Casal G, Cronin T, et al. Evaluation of Dose and Safety of AAV7m8 and AAV8BP2 in the Non-Human Primate Retina. Hum Gene Ther (2016). doi: 10.1089/hum.2016.111. PubMed PMID: 27750461.
25. Dalkara D, Byrne L C, Klimczak R R, Visel M, Yin L, Merigan W H, et al. In vivo-directed evolution of a new adeno-associated virus for therapeutic outer retinal gene delivery from the vitreous. Sci Transl Med (2013) 5(189): 189ra76. doi: 10.1126/scitranslmed.3005708. PubMed PMID: 23761039.
26. Dalkara D, Kolstad K D, Caporale N, Visel M, Klimczak R R, Schaffer D V, et al. Inner limiting membrane barriers to AAV-mediated retinal transduction from the vitreous. Mol Ther (2009) 17(12):2096-102. doi: 10.1038/mt.2009.181. PubMed PMID: 19672248; PubMed Central PMCID: PMCPMC2814392.
27. Mace E, Caplette R, Mane O, Sengupta A, Chaffiol A, Barbe P, et al. Targeting channelrhodopsin-2 to ON-bipolar cells with vitreally administered AAV Restores ON and OFF visual responses in blind mice. Mol Ther (2015) 23(1):7-16. doi: 10.1038/mt.2014.154. PubMed PMID: 25095892; PubMed Central PMCID: PMCPMC4270733.
28. Liang F Q, Anand V, Maguire A M, Bennett J. Intraocular delivery of recombinant virus. Methods Mol Med (2001) 47:125-39. doi: 10.1385/1-59259-085-3:125. PubMed PMID: 21394582.
29. Mohamed M, Topping N, Jafri H, Raashed Y, McKibbin M, Inglehearn C. Progression of phenotype in Leber's congenital amaurosis with a mutation at the LCA5 locus. Br J Ophthalmol (2003) 87(4):473-5.
30. Ashtari M, Cyckowski L L, Monroe J F, Marshall K A, Chung D C, Auricchio A, et al. The human visual cortex responds to gene therapy-mediated recovery of retinal function. J Clin Invest 121(6):2160-8. Epub 2011/05/25. doi: 57377 [pii] 10.1172/JCI57377. PubMed PMID: 21606598; PubMed Central PMCID: PMC3104779.
31. Bennett J, Ashtari M, Wellman J, Marshall K A, Cyckowski L L, Chung D C, et al. AAV2 gene therapy readministration in three adults with congenital blindness. Sci Transl Med 4(120):120ra15. Epub 2012/02/11. doi: 4/120/120ra15 [pii] 10.1126/scitranslmed.3002865. PubMed PMID: 22323828.

What is claimed:

1. A nucleic acid molecule comprising the nucleotide sequence of SEQ ID NO: 3 encoding human Lebercilin.

2. An expression cassette comprising the nucleic acid molecule of claim 1.

3. A recombinant adeno-associated virus (rAAV) comprising an AAV capsid, and a vector genome packaged therein, the vector genome comprising:
   (a) an AAV 5' inverted terminal repeat (ITR) sequence;
   (b) a promoter;
   (c) a coding sequence encoding a human Lebercilin; and
   (d) an AAV 3' ITR sequence,
   wherein the coding sequence of (c) comprises the nucleotide sequence of SEQ ID NO: 3 and is operably linked to the promoter of (b).

4. The rAAV of claim 3, wherein the rAAV capsid is an AAV7m8 capsid, an AAV8 capsid, an AAV6 capsid, an AAV9 capsid, an AAV7 capsid, an AAV5 capsid, an AAV2 capsid, an AAV1 capsid, an AAV3 capsid, or an AAV4 capsid.

5. The rAAV of claim 3, wherein the promoter is a cytomegalovirus (CMV) promoter or a hybrid promoter comprising a CMV promoter sequence and a chicken beta actin (CBA) promoter sequence.

6. The rAAV of claim 3, wherein the AAV 5' ITR sequence and/or AAV 3' ITR sequence is from AAV2.

7. The rAAV of claim 3, wherein the vector genome further comprises a polyA.

8. The rAAV of claim 3, wherein the vector genome further comprises an intron.

9. The rAAV of claim 3, wherein the vector genome further comprises an enhancer.

10. A composition comprising the rAAV of claim 5 and a pharmaceutical acceptable carrier or excipient suitable for delivery to an eye.

11. An aqueous suspension suitable for administration to an LCA patient, the suspension comprising an aqueous suspending liquid and about $1\times 10^{10}$ genome copies (GC) to about $1\times 10^{12}$ GC of a recombinant adeno-associated virus (rAAV) useful as a therapeutic for LCA, the rAAV having an AAV capsid, and having packaged therein a vector genome comprising:
  (a) an AAV 5' inverted terminal repeat (ITR) sequence;
  (b) a promoter;
  (c) a coding sequence encoding a human Lebercilin; and
  (d) an AAV 3' ITR sequence,
  wherein the coding sequence of (c) comprises the nucleotide sequence of SEQ ID NO: 3 and is operably linked to the promoter of (b).

12. The aqueous suspension of claim 11, wherein the aqueous suspension is suitable for subretinal or intravitreal injection.

13. The aqueous suspension of claim 11, wherein the promoter comprises the nucleotide sequence of SEQ ID NO: 10.

14. The aqueous suspension of claim 11, wherein the AAV capsid is an AAV8 capsid.

15. The aqueous suspension of claim 11, wherein the vector genome further comprises a CBA exon1 and intron of nucleotides 824 to 1795 of SEQ ID NO: 8.

16. A method of treating a subject having LCA comprising subretinally or intravitreally administering to an eye of the subject at least or about $1\times 10^9$ GC of the rAAV of claim 3.

17. The method of claim 16, wherein from about $1\times 10^9$ to about $1\times 10^{13}$ GC of the rAAV is administered in an aqueous suspension.

18. The method of claim 16, wherein a dosage of from about $1\times 10^9$ to about $1\times 10^{13}$ GC of the rAAV is administered in a volume comprising about or at least 150 microliters, thereby restoring visual function in the subject.

19. A plasmid comprising the nucleic acid molecule of claim 1.

20. The expression cassette of claim 2, wherein the expression cassette is flanked by an AAV 5' ITR sequence and an AAV 3' ITR sequence.

21. A plasmid comprising the expression cassette of claim 20.

22. A packaging host cell comprising the plasmid of claim 21.

* * * * *

UNITED STATES PATENT AND TRADEMARK OFFICE
CERTIFICATE OF CORRECTION

Page 1 of 1

PATENT NO. : 11,564,996 B2
APPLICATION NO. : 16/489770
DATED : January 31, 2023
INVENTOR(S) : Jean Bennett et al.

It is certified that error appears in the above-identified patent and that said Letters Patent is hereby corrected as shown below:

In the Claims

Column 96, Line 53 Claim 4, amended as follows:
-- 4. The rAAV of claim 3, wherein the AAV capsid is an AAV7m8 capsid, an AAV8 capsid, an AAV6 capsid, an AAV9 capsid, an AAV7 capsid, an AAV5 capsid, an AAV2 capsid, an AAV1 capsid, an AAV3 capsid, or an AAV4 capsid. --

Signed and Sealed this
Seventh Day of March, 2023

Katherine Kelly Vidal
*Director of the United States Patent and Trademark Office*

SEQUENCE LISTING

```
<160> NUMBER OF SEQ ID NOS: 15

<210> SEQ ID NO 1
<211> LENGTH: 697
<212> TYPE: PRT
<213> ORGANISM: Homo sapiens

<400> SEQUENCE: 1

Met Gly Glu Arg Ala Gly Ser Pro Gly Thr Asp Gln Glu Arg Lys Ala
1               5                   10                  15

Gly Lys His His Tyr Ser Tyr Leu Ser Asp Phe Glu Thr Pro Gln Ser
            20                  25                  30

Ser Gly Arg Ser Ser Leu Val Ser Ser Ser Pro Ala Ser Val Arg Arg
        35                  40                  45

Lys Asn Pro Lys Arg Gln Thr Ser Asp Gly Gln Val His His Gln Ala
    50                  55                  60

Pro Arg Lys Pro Ser Pro Lys Gly Leu Pro Asn Arg Lys Gly Val Arg
65                  70                  75                  80

Val Gly Phe Arg Ser Gln Ser Leu Asn Arg Glu Pro Leu Arg Lys Asp
                85                  90                  95

Thr Asp Leu Val Thr Lys Arg Ile Leu Ser Ala Arg Leu Leu Lys Ile
                100                 105                 110
```

-continued

```
Asn Glu Leu Gln Asn Glu Val Ser Glu Leu Gln Val Lys Leu Ala Glu
            115                 120                 125
Leu Leu Lys Glu Asn Lys Ser Leu Lys Arg Leu Gln Tyr Arg Gln Glu
        130                 135                 140
Lys Ala Leu Asn Lys Phe Glu Asp Ala Glu Asn Glu Ile Ser Gln Leu
145                 150                 155                 160
Ile Phe Arg His Asn Asn Glu Ile Thr Ala Leu Lys Glu Arg Leu Arg
                165                 170                 175
Lys Ser Gln Glu Lys Glu Arg Ala Thr Glu Lys Arg Val Lys Asp Thr
            180                 185                 190
Glu Ser Glu Leu Phe Arg Thr Lys Phe Ser Leu Gln Lys Leu Lys Glu
        195                 200                 205
Ile Ser Glu Ala Arg His Leu Pro Glu Arg Asp Asp Leu Ala Lys Lys
    210                 215                 220
Leu Val Ser Ala Glu Leu Lys Leu Asp Asp Thr Glu Arg Arg Ile Lys
225                 230                 235                 240
Glu Leu Ser Lys Asn Leu Glu Leu Ser Thr Asn Ser Phe Gln Arg Gln
                245                 250                 255
Leu Leu Ala Glu Arg Lys Arg Ala Tyr Glu Ala His Asp Glu Asn Lys
            260                 265                 270
Val Leu Gln Lys Glu Val Gln Arg Leu Tyr His Lys Leu Lys Glu Lys
        275                 280                 285
Glu Arg Glu Leu Asp Ile Lys Asn Ile Tyr Ser Asn Arg Leu Pro Lys
    290                 295                 300
Ser Ser Pro Asn Lys Glu Lys Glu Leu Ala Leu Arg Lys Asn Ala Ala
305                 310                 315                 320
Cys Gln Ser Asp Phe Ala Asp Leu Cys Thr Lys Gly Val Gln Thr Met
                325                 330                 335
Glu Asp Phe Lys Pro Glu Glu Tyr Pro Leu Thr Pro Glu Thr Ile Met
            340                 345                 350
Cys Tyr Glu Asn Lys Trp Glu Glu Pro Gly His Leu Thr Leu Asp Leu
        355                 360                 365
Gln Ser Gln Lys Gln Asp Arg His Gly Glu Ala Gly Ile Leu Asn Pro
    370                 375                 380
Ile Met Glu Arg Glu Glu Lys Phe Val Thr Asp Glu Glu Leu His Val
385                 390                 395                 400
Val Lys Gln Glu Val Glu Lys Leu Glu Asp Glu Trp Glu Arg Glu Glu
                405                 410                 415
Leu Asp Lys Lys Gln Lys Glu Lys Ala Ser Leu Leu Glu Arg Glu Glu
            420                 425                 430
Lys Pro Glu Trp Glu Thr Gly Arg Tyr Gln Leu Gly Met Tyr Pro Ile
        435                 440                 445
Gln Asn Met Asp Lys Leu Gln Gly Glu Glu Glu Arg Leu Lys Arg
    450                 455                 460
Glu Met Leu Leu Ala Lys Leu Asn Glu Ile Asp Arg Glu Leu Gln Asp
465                 470                 475                 480
Ser Arg Asn Leu Lys Tyr Pro Val Leu Pro Leu Pro Asp Phe Glu
                485                 490                 495
Ser Lys Leu His Ser Pro Glu Arg Ser Pro Lys Thr Tyr Arg Phe Ser
            500                 505                 510
Glu Ser Ser Glu Arg Leu Phe Asn Gly His His Leu Gln Asp Ile Ser
        515                 520                 525
Phe Ser Thr Pro Lys Gly Glu Gly Gln Asn Ser Gly Asn Val Arg Ser
```

```
            530             535             540

Pro Ala Ser Pro Asn Glu Phe Ala Phe Gly Ser Tyr Val Pro Ser Phe
545                 550                 555                 560

Ala Lys Thr Ser Glu Arg Ser Asn Pro Phe Ser Gln Lys Ser Ser Phe
                565                 570                 575

Leu Asp Phe Gln Arg Asn Ser Met Glu Lys Leu Ser Lys Asp Gly Val
            580                 585                 590

Asp Leu Ile Thr Arg Lys Glu Lys Ala Asn Leu Met Glu Gln Leu
        595                 600                 605

Phe Gly Ala Ser Gly Ser Ser Thr Ile Ser Ser Lys Ser Ser Asp Pro
610                 615                 620

Asn Ser Val Ala Ser Lys Gly Asp Ile Asp Pro Leu Asn Phe Leu
625                 630                 635                 640

Pro Gly Asn Lys Gly Ser Arg Asp Gln Glu His Asp Glu Asp Glu Gly
                645                 650                 655

Phe Phe Leu Ser Glu Gly Arg Ser Phe Asn Pro Asn Arg His Arg Leu
            660                 665                 670

Lys His Ala Asp Asp Lys Pro Ala Val Lys Ala Ala Asp Ser Val Glu
        675                 680                 685

Asp Glu Ile Glu Glu Val Ala Leu Arg
        690                 695

<210> SEQ ID NO 2
<211> LENGTH: 2094
<212> TYPE: DNA
<213> ORGANISM: Homo sapiens

<400> SEQUENCE: 2
atgggggaaa gagcaggaag tccaggtact gaccaagaaa gaaaggcagg caaacaccat       60
tattcttact tatctgattt tgaaacgcca cagtcttctg ccgatcatc gctggtcagt      120 tcttcacctg caagtgttag gagaaaaaat cctaaaagac aaacttcaga tggccaagta      180
catcaccaag cccctcggaa accaagcccc aagggtctac caaacagaaa gggagtccga      240
gtgggatttc gctcccagag cctcaataga gagccacttc ggaaagatac tgatcttgtt      300
acaaaacgga ttctgtctgc aagactgcta aaaatcaatg agttgcagaa tgaagtatct      360
gaactccagg tcaagttagc tgagctgcta aagaaaata atctttgaa aaggcttcag      420 tacagacagg agaaagccct gaataagttt gaagatgccg aaatgaaat ctcacaactt      480 atatttcgtc ataacaatga gattacagca ctcaaagaac gcttaagaaa atctcaagag      540
aaagaacggg caactgagaa aagggtaaaa gatacagaaa gtgaactatt taggacaaaa      600
ttttccttac agaaactgaa agagatctct gaagctagac acctacctga cagagatgat      660
ttggcaaaga aactagtttc agcagagtta agttagatg acaccgagag aagaattaag      720
gagctatcga aaaccttga actgagtact aacagtttcc aacgacagtt gcttgctgaa      780
aggaaaaggg catatgaggc tcatgatgaa ataaagttc ttcaaaagga ggtacagcga      840
ctatatcaca aattaaagga aaaggagaga gaactggata taaaaatat atattctaat      900 cgtctgccaa agtcctctcc aaataaagag aagaacttg cattaagaaa aatgctgca      960 tgccagagtg attttgcaga cctgtgtaca aaggagtac aaaccatgga agacttcaag     1020
ccagaagaat atcctttaac tccagaaaca attatgtgtt acgaaaacaa atgggaagaa     1080
ccaggacatc ttactttgga cttgcaatct caaaagcaag acaggcatgg agaagcaggg     1140
attctaaacc caattatgga agagaagaa aaatttgtta cagatgaaga actccatgtc     1200
```

```
gtaaaacagg aggttgaaaa gctggaggat gaatgggaaa gagaagaact tgataaaaag    1260
caaaaagaaa aggcatcttt actggaaaga gaagaaaagc cagagtggga aactggaagg    1320
taccaactag gaatgtatcc aattcagaat atggataaat tgcaaggaga ggaagaagaa    1380
agactgaaga gagaaatgct acttgctaaa ctgaatgaaa ttgacagaga actccaagat    1440
tctcgaaatc taaaataccc tgttttgcca ttgttacctg attttgaatc aaaactacac    1500
tccccagaga gaagccccaa aacatacagg ttctctgaat cctcagagag attatttaat    1560
gggcatcatt tgcaagacat cagtttctca actccaaaag gagaaggtca gaattcagga    1620
aatgttagaa gtccagcctc ccctaatgag ttcgcatttg gtagctacgt gccttcgttt    1680
gcaaaaacat cagagaggtc aaatccattt agtcaaaaaa gtagtttttt ggatttccaa    1740
agaaacagta tggaaaaact tagtaaagat ggtgtagatt taattacaag aaaagagaaa    1800
aaagctaatt tgatggaaca gttatttggt gccagtggta gcagcaccat ttcctccaaa    1860
agcagtgacc caaattctgt ggcttccagt aaaggagaca ttgaccctct aaattttctc    1920
cctgggaata aaggcagcag agatcaagaa catgatgaag atgaaggctt tttcctcagt    1980
gaaggaagaa gttttaatcc aaataggcac cgattaaaac atgcagacga taaaccagca    2040
gtaaaagcag ctgattctgt agaagatgaa attgaagaag tagcactgag atga          2094
```

<210> SEQ ID NO 3
<211> LENGTH: 2093
<212> TYPE: DNA
<213> ORGANISM: Artificial Sequence
<220> FEATURE:
<223> OTHER INFORMATION: constructed sequence

<400> SEQUENCE: 3

```
atgggagaac gagcaggcag ccctggtacg gaccaggaac gcaaggcggg gaaacaccac      60
tatagctatt tgtcagactt tgagacaccg cagagctcgg gtcggtcatc cttggtgtcg     120
tcaagcccgg ctagcgtccg gcgaaagaat ccaaagcgcc aaacgtcaga tggccaggtg     180
catcatcagg ctccccggaa accctcgccc aaaggattgc cgaacagaaa gggggtccgg     240
gtagggttta gatcgcagag cctgaatcgc gagcctctta gaaaagatac agaccttgtg     300
actaagagga ttctgtcggc acgactgttg aagattaacg aacttcagaa tgaggtgtca     360
gaactccaag taaaacttgc ggaactgctt aaggagaaca aatcgctcaa gcggcttcag     420
tatcgccaag agaaagcgct caacaagttc gaggacgcgg aaaacgagat tcgcagttg      480 atctttaggc ataacaacga gatcaccgcc cttaaagaac gcttgcgcaa agccaggag      540 aaagaacgcg ccacggagaa gagggtcaag gacaccgaat cggaactgtt tagaactaag     600
ttttcgcttc aaaagcttaa agaaatctcg gaagcgaggc atctccctga gcgagatgat    660
ttggctaaga acttgtatc ggcagagctc aaattggatg atacggagag gaggattaag     720
gaacttagca aaaaccttga attgtcaacg aactcgtttc aacggcagct gttggccgaa     780
agaaaacggg cttatgaagc gcacgatgaa acaaggtgc tgcagaaaga ggtgcagagg     840
ttgtaccata agctgaaaga gaaggaaaga gagctggaca tcaaaaacat ctacagcaac     900
cggctgccta agtcatcgcc aaacaaagag aaagagctgg cattgagaaa gaatgcagcc     960
tgccagtcgg attttgcgga tctgtgcacg aaaggagtac agaccatgga ggactttaag    1020
cccgaagaat accccactta acccgagaca atcatgtgtt acgagaacaa gtgggaggag    1080
ccgggacacc ttactcttga tctccagagc caaaaacagg atcgccacgg cgaggccggt    1140
```

| | |
|---|---|
| attctcaacc cgatcatgga gagagaggag aagttcgtca cagatgagga gctccacgtc | 1200 |
| gtgaaacaag aagtggagaa gctcgaggac gaatgggaac gagaagagct tgataagaag | 1260 |
| cagaaggaga aagcatcgtt gctggaacgc gaagagaaac cggagtggga gactgggagg | 1320 |
| tatcagcttg ggatgtaccc aattcagaat atggacaaac tccaggggga ggaagaagag | 1380 |
| aggctcaaga gggaaatgct cctggccaag ttgaatgaga ttgaccggga gttgcaagac | 1440 |
| tcacgcaacc tcaagtaccc tgtactcccc ctgcttccgg attttgaatc aaaacttcac | 1500 |
| tcccccgaac ggagccccaa gacctatcga ttctcggaat cgtcggagag actcttcaat | 1560 |
| ggacaccatt tgcaagacat ctcctttca acacccaaag ggaaggcca gaattccgga | 1620 |
| aatgtgcggt cgccagcgtc gccaaatgag ttcgcattcg gttcgtacgt gccctcattc | 1680 |
| gcgaaaacct cggagagatc caacccttc agccaaaagt cgtcattctt ggatttccag | 1740 |
| agaaactcca tggaaaagct ctccaaggat ggagtcgatc tcatcactag aaaagagaag | 1800 |
| aaggccaatc tcatggaaca gttgttcgga gcgtcgggtt cgtccaccat ctcctccaag | 1860 |
| tcatcagacc ccaattcggt cgcatcctca agggagaca tcgaccctt gaatttcctg | 1920 |
| ccgggaaaca agggttcgcg agatcaggaa catgacgagg acgaggggtt tttcttgtcc | 1980 |
| gaagggaggt ccttcaatcc gaatcgccac agattgaaac acgcggatga caagcctgcg | 2040 |
| gtgaaggctg cggactcagt agaggacgag atcgaggaag tggccctgag atg | 2093 |

<210> SEQ ID NO 4
<211> LENGTH: 2094
<212> TYPE: DNA
<213> ORGANISM: Homo sapiens

<400> SEQUENCE: 4

| | |
|---|---|
| atgggggaaa gagcaggaag tccaggtact gatcaagaaa gaaaggcagg caaacaccat | 60 |
| tattcttact tatctgattt tgaaacgcca cagtcttctg ccgatcatc gctggtcagt | 120 |
| tcttcacctg caagtgttag gagaaaaaat cctaaaagac aaacttcaga tggccaagta | 180 |
| catcaccaag cccctcggaa accaagccct aagggtctac caaacagaaa gggagtccga | 240 |
| gtgggatttc gctcccagag cctcaataga gagccacttc ggaaagatac tgatcttgtt | 300 |
| acaaaacgga ttctgtctgc aagactgcta aaaatcaatg agttgcagaa tgaagtatct | 360 |
| gaactccagg tcaagttagc tgagctgcta aaagaaaata atctttgaa aaggcttcag | 420 |
| tacagacagg agaaagccct gaataagttt gaagatgccg aaaatgaaat ctcacaactt | 480 |
| atatttcgtc ataacaatga gattacagca ctcaaagaac gcttaagaaa atctcaagag | 540 |
| aaagaacggg caactgagaa aagggtaaaa gatacagaaa gtgaactatt taggacaaaa | 600 |
| ttttccttac agaaactgaa agagatctct gaagctagac acctacctga acgagatgat | 660 |
| ttggcaaaga aactagtttc agcagagtta agttagatg acaccgagag aagaattaag | 720 |
| gagctatcga aaaaccttga actgagtact aacagtttcc aacgacagtt gcttgctgaa | 780 |
| aggaaaaggg catatgaggc tcatgatgaa ataaagttc ttcaaaagga ggtacagcga | 840 |
| ctatatcaca aattaaagga aaggagaga gaactggata taaaaaatat atattctaat | 900 |
| cgtctgccaa agtcctctcc aaataaagag aagaacttg cattaagaaa aaatgctgca | 960 |
| tgccagagtg attttgcaga cctgtgtaca aaggagtac aaaccatgga agacttcaag | 1020 |
| ccagaagaat atcctttaac tccagaaaca attatgtgtt acgaaaacaa atgggaagaa | 1080 |
| ccaggacatc ttactttgga cttgcaatct caaaagcaag acaggcatgg agaagcaggg | 1140 |
| attctaaacc caattatgga agagaagaa aaatttgtta cagatgaaga actccatgtc | 1200 |

| | |
|---|---|
| gtaaaacagg aggttgaaaa gctggaggat gaatgggaaa gagaagaact tgataaaaag | 1260 |
| caaaaagaaa aggcatcttt actggaaaga gaagaaaagc cagagtggga aactggaagg | 1320 |
| taccaactag gaatgtatcc aattcagaat atggataaat tgcaaggaga ggaagaagaa | 1380 |
| agactgaaga gagaaatgct acttgctaaa ctgaatgaaa ttgacagaga actccaagat | 1440 |
| tctcgaaatc taaaatacc tgttttgcca ttgttacctg attttgaatc aaaactacac | 1500 |
| tccccagaga gaagccccaa aacatacagg ttctctgaat cctcagagag attatttaat | 1560 |
| gggcatcatt tgcaagacat cagtttctca actccaaaag gagaaggtca gaattcagga | 1620 |
| aatgttagaa gtccagcctc ccctaatgag ttcgcatttg gtagctacgt gccttcgttt | 1680 |
| gcaaaaacat cagagaggtc aaatccattt agtcaaaaaa gtagttttt ggatttccaa | 1740 |
| agaaacagta tggaaaaact tagtaaagat ggtgtagatt taattacaag aaaagagaaa | 1800 |
| aaagctaatt tgatggaaca gttatttggt gccagtggta gcagcaccat tcctccaaa | 1860 |
| agcagtgacc caaattctgt ggcttccagt aaaggagaca ttgaccctct aaattttctc | 1920 |
| cctgggaata aaggcagcag agatcaagaa catgatgaag atgaaggctt tttcctcagt | 1980 |
| gaaggaagaa gttttaatcc aaataggcac cgattaaaac atgcagacga taaaccagca | 2040 |
| gtaaaagcag ctgattctgt agaagatgaa attgaagaag tagcactgag atga | 2094 |

<210> SEQ ID NO 5
<211> LENGTH: 2094
<212> TYPE: DNA
<213> ORGANISM: Homo sapiens

<400> SEQUENCE: 5

| | |
|---|---|
| atgggggaaa gagcaggaag tccaggtact gatcaagaaa gaaaggcagg caaacaccat | 60 |
| tattcttact tatctgattt tgaaacgcca cagtcttctg gccgatcatc gctggtcagt | 120 |
| tcttcacctg caagtgttag gagaaaaaat cctaaaagac aaacttcaga tggccaagta | 180 |
| catcaccaag cccctcggaa accaagccct aagggtctac caaacagaaa gggagtccga | 240 |
| gtgggatttc gctcccagag cctcaataga gagccacttc ggaaagatac tgatcttgtt | 300 |
| acaaaacgga ttctgtctgc aagactgcta aaaatcaatg agttgcagaa tgaagtatct | 360 |
| gaactccagg tcaagttagc tgagctgcta aagaaaaata atctttgaa aaggcttcag | 420 |
| tacagacagg agaaagccct gaataagttt gaagatgccg aaaatgaaat ctcacaactt | 480 |
| atatttcgtc ataacaatga gattacagca ctcaagaac gcttaagaaa atctcaagag | 540 |
| aaagaacggg caactgagaa aagggtaaaa gatacagaaa gtgaactatt taggacaaaa | 600 |
| ttttccttac agaaactgaa agagatctct gaagctagac acctacctga acgagatgat | 660 |
| ttggcaaaga aactagtttc agcagagtta agttagatg acaccgagag aagaattaag | 720 |
| gagctatcga aaaaccttga actgagtact aacagtttcc aacgacagtt gcttgctgaa | 780 |
| aggaaaaggg catatgaggc tcatgatgaa aataaagttc ttcaaaagga ggtacagcga | 840 |
| ctatatcaca aattaaagga aaaggagaga gaactggata taaaaaatat atattctaat | 900 |
| cgtctgccaa agtcctctcc aaataaagag aagaacttg cattaagaaa aaatgctgca | 960 |
| tgccagagtg attttgcaga cctgtgtaca aaggagtac aaaccatgga agacttcaag | 1020 |
| ccagaagaat atccttaac tccagaaaca attatgtgtt acgaaaacaa atgggaagaa | 1080 |
| ccaggacatc ttactttgga cttgcaatct caaaagcaag acaggcatgg agaagcaggg | 1140 |
| attctaaacc caattatgga aagagaagaa aaatttgtta cagatgaaga actccatgtc | 1200 |

```
gtaaaacagg aggttgaaaa gctggaggat gaatgggaaa gagaagaact tgataaaaag    1260
caaaaagaaa aggcatcttt actggaagaa gaagaaaagc cagagtggga aactggaagg    1320
taccaactag gaatgtatcc aattcagaat atggataaat tgcaaggaga ggaagaagaa    1380
agactgaaga gagaaatgct acttgctaaa ctgaatgaaa ttgacagaga actccaagat    1440
tctcgaaatc taaaataccc tgttttgcca ttgttacctg attttgaatc aaaactacac    1500
tccccagaga gaagccccaa aacatacagg ttctctgaat cctcagagag attatttaat    1560
gggcatcatt tgcaagacat cagtttctca actccaaaag gagaaggtca gaattcagga    1620
aatgttagaa gtccagcctc ccctaatgag ttcgcatttg gtagctacgt gccttcgttt    1680
gcaaaaacat cagagaggtc aaatccattt agtcaaaaaa gtagtttttt ggatttccaa    1740
agaaacagta tggaaaaact tagtaaagat ggtgtagatt taattacaag aaaagagaaa    1800
aaagctaatt tgatggaaca gttatttggt gccagtggta gcagcaccat ttcctccaaa    1860
agcagtgacc caaattctgt ggcttccagt aaaggagaca ttgaccctct aaattttctc    1920
cctgggaata aaggcagcag agatcaagaa catgatgaag atgaaggctt tttcctcagt    1980
gaaggaagaa gttttaatcc aaataggcac cgattaaaac atgcagacga taaaccagca    2040
gtaaaagcag ctgattctgt agaagatgaa attgaagaag tagcactgag atga          2094

<210> SEQ ID NO 6
<211> LENGTH: 2094
<212> TYPE: DNA
<213> ORGANISM: Homo sapiens

<400> SEQUENCE: 6
atgggggaaa gagcaggaag tccaggtact gatcaagaaa gaaaggcagg caaacaccat      60
tattcttact tatctgattt tgaaacgcca cagtcttctg gccgatcatc gctggtcagt     120
tcttcacctg caagtgttag gagaaaaaat cctaaaagac aaacttcaga tggccaagta     180
catcaccaag cccctcggaa accaagccct aagggtctac caaacagaaa gggagtccga     240
gtgggatttc gctcccagag cctcaataga gagccacttc ggaaagatac tgatcttgtt     300
acaaaacgga ttctgtctgc aagactgcta aaaatcaatg agttcagaat gaagtatct     360 gaactccagg tcaagttagc tgagctgcta aaagaaaata atctttgaa aaggcttcag     420 tacagacagg agaaagccct gaataagttt gaagatgccg aaaatgaaat ctcacaactt     480
atatttcgtc ataacaatga gattacagca ctcaaagaac gcttaagaaa atctcaagag     540
aaagaacggg caactgagaa aagggtaaaa gatacagaaa gtgaactatt taggacaaaa     600
ttttccttac agaaactgaa agagatctct gaagctagac acctacctga acgagatgat     660
ttggcaaaga aactagtttc agcagagtta aagttagatg acaccgagag aagaattaag     720
gagctatcga aaaaccttga actgagtact aacagtttcc aacgacagtt gcttgctgaa     780
aggaaaaggg catatgaggc tcatgatgaa aataaagttc ttcaaaagga ggtacagcga     840
ctatatcaca aattaaagga aaaggagaga gaactggata taaaaaatat atattctaat     900
cgtctgccaa agtcctctcc aaataaagag aaagaacttg cattaagaaa aaatgctgca     960
tgccagagtg attttgcaga cctgtgtaca aaggagtac aaaccatgga agacttcaag    1020
ccagaagaat atcctttaac tccagaaaca attatgtgtt acgaaaacaa atgggaagaa    1080
ccaggacatc ttacttttgga cttgcaatct caaaagcaag acaggcatgg agaagcaggg    1140
attctaaacc caattatgga aagagaagaa aaatttgtta cagatgaaga actccatgtc    1200
gtaaaacagg aggttgaaaa gctggaggat gaatgggaaa gagaagaact tgataaaaag    1260
```

```
caaaaagaaa aggcatcttt actggaaaga gaagaaaagc cagagtggga aactggaagg    1320
taccaactag gaatgtatcc aattcagaat atggataaat tgcaaggaga ggaagaagaa    1380
agactgaaga gagaaatgct acttgctaaa ctgaatgaaa ttgacagaga actccaagat    1440
tctcgaaatc taaaataccc tgttttgcca ttgttacctg attttgaatc aaaactacac    1500
tccccagaga gaagcccaa aacatacagg ttctctgaat cctcagagag attatttaat    1560
gggcatcatt tgcaagacat cagtttctca actccaaaag gagaaggtca gaattcagga    1620
aatgttagaa gtccagcctc ccctaatgag ttcgcatttg gtagctacgt gccttcgttt    1680
gcaaaaacat cagagaggtc aaatccattt agtcaaaaaa gtagttttt ggatttccaa     1740 agaaacagta tggaaaaact tagtaaagat ggtgtagatt taattacaag aaaagagaaa    1800
aaagctaatt tgatgaaca gttatttggt gccagtggta gcagcaccat ttcctccaaa     1860
agcagtgacc caaattctgt ggcttccagt aaaggagaca ttgaccctct aaattttctc    1920
cctgggaata aaggcagcag agatcaagaa catgatgaag atgaaggctt tttcctcagt    1980
gaaggaagaa gttttaatcc aaataggcac cgattaaaac atgcagacga taaaccagca    2040
gtaaaagcag ctgattctgt agaagatgaa attgaagaag tagcactgag atga          2094

<210> SEQ ID NO 7
<211> LENGTH: 2094
<212> TYPE: DNA
<213> ORGANISM: Homo sapiens

<400> SEQUENCE: 7
atgggggaaa gagcaggaag tccaggtact gatcaagaaa gaaggcagg caaacaccat       60 tattcttact tatctgattt tgaaacgcca cagtcttctg ccgatcatc gctggtcagt      120 tcttcacctg caagtgttag gagaaaaaat cctaaaagac aaacttcaga tggccaagta    180
catcaccaag cccctcggaa accaagccct aagggtctac caaacagaaa gggagtccga    240
gtgggatttc gctcccagag cctcaataga gagccacttc ggaaagatac tgatcttgtt    300
acaaaacgga ttctgtctgc aagactgcta aaaatcaatg agttgcagaa tgaagtatct    360
gaactccagg tcaagttagc tgagctgcta aaagaaaata atctttgaa aaggcttcag      420 tacagacagg agaaagccct gaataagttt gaagatgccg aaaatgaaat ctcacaactt    480
atatttcgtc ataacaatga gattacagca ctcaaagaac gcttaagaaa atctcaagag    540
aaagaacggg caactgagaa aagggtaaaa gatacagaaa gtgaactatt taggacaaaa    600
ttttccttac agaaactgaa agagatctct gaagctagac acctacctga cgagatgat     660 ttggcaaaga aactagtttc agcagagtta aagttagatg acaccgagag aagaattaag    720
gagctatcga aaaaccttga actgagtact aacagtttcc aacgacagtt gcttgctgaa    780
aggaaaaggg catatgaggc tcatgatgaa ataaagttc ttcaaaagga ggtacagcga      840
ctatatcaca aattaaagga aaaggagaga gaactggata taaaaatat atattctaat     900 cgtctgccaa agtcctctcc aaataaagag aaagaacttg cattaagaaa aatgctgca    960 tgccagagtg attttgcaga cctgtgtaca aaggagtac aaaccatgga agacttcaag     1020
ccagaagaat atcctttaac tccagaaaca attatgtgtt acgaaaacaa atgggaagaa    1080
ccaggacatc ttactttgga cttgcaatct caaaagcaag acaggcatgg agaagcaggg    1140
attctaaacc caattatgga aagagaagaa aaatttgtta cagatgaaga actccatgtc    1200
gtaaaacagg aggttgaaaa agctggagga gaatgggaaa gagaagaact tgataaaaag    1260
```

```
caaaaagaaa aggcatcttt actggaaaga gaagaaaagc cagagtggga aactggaagg    1320
taccaactag gaatgtatcc aattcagaat atggataaat tgcaaggaga ggaagaagaa    1380
agactgaaga gagaaatgct acttgctaaa ctgaatgaaa ttgacagaga actccaagat    1440
tctcgaaatc taaaataccc tgttttgcca ttgttacctg attttgaatc aaaactacac    1500
tccccagaga gaagccccaa acatacaggt tctctgaat cctcagagag attatttaat     1560
gggcatcatt tgcaagacat cagtttctca actccaaaag gagaaggtca gaattcagga    1620
aatgttagaa gtccagcctc ccctaatgag ttcgcatttg gtagctacgt gccttcgttt    1680
gcaaaaacat cagagaggtc aaatccattt agtcaaaaaa gtagttttt ggatttccaa     1740 agaaacagta tggaaaaact tagtaaagat ggtgtagatt taattacaag aaaagagaaa    1800
aaagctaatt tgatggaaca gttatttggt gccagtggta gcagcaccat tcctccaaa     1860 agcagtgacc caaattctgt ggcttccagt aaaggagaca ttgaccctct aaattttctc    1920
cctgggaata aaggcagcag agatcaagaa catgatgaag atgaaggctt tttcctcagt    1980
gaaggaagaa gttttaatcc aaataggcac cgattaaaac atgcagacga taaaccagca    2040
gtaaaagcag ctgattctgt agaagatgaa attgaagaag tagcactgag atga         2094

<210> SEQ ID NO 8
<211> LENGTH: 12231
<212> TYPE: DNA
<213> ORGANISM: Artificial Sequence
<220> FEATURE:
<223> OTHER INFORMATION: constructed sequence

<400> SEQUENCE: 8
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact    120
aggggttcct tgtagttaat gattaacccg ccatgctact tatctacgta gcaagctagc    180
tagttattaa tagtaatcaa ttacggggtc attagttcat agcccatata tggagttccg    240
cgttacataa cttacggtaa atggcccgcc tggctgaccg cccaacgacc cccgcccatt    300
gacgtcaata atgacgtatg ttcccatagt aacgccaata gggactttcc attgacgtca    360
atgggtggag tatttacggt aaactgccca cttggcagta catcaagtgt atcatatgcc    420
aagtacgccc cctattgacg tcaatgacgg taaatggccc gcctggcatt atgcccagta    480
catgacctta tgggactttc ctacttggca gtacatctac gtattagtca tcgctattaa    540
catggtcgag gtgagcccca cgttctgctt cactctcccc atctcccccc cctccccacc    600 cccaatttg tatttattta ttttttaatt attttgtgca gcgatggggg cggggggggg     660
gggggggcgc gcgccaggcg gggcggggcg gggcgagggg cggggcgggg cgaggcggag    720
aggtgcggcg gcagccaatc agagcggcgc gctccgaaag tttcctttta tggcgaggcg    780
gcggcggcgg cggccctata aaaagcgaag cgcgcggcgg gcgggagtc gctgcgacgc     840 tgccttcgcc ccgtgccccg ctccgccgcc gcctcgcgcc gcccgccccg gctctgactg    900
accgcgttac tcccacaggt gagcgggcgg gacggccctt ctcctccggg ctgtaattag    960
cgcttggttt aatgacggct tgtttctttt ctgtggctgc gtgaaagcct tgaggggctc    1020
cgggagggcc ctttgtgcgg gggagcggc tcggggggtg cgtgcgtgtg tgtgtgcgtg    1080
gggagcgccg cgtgcggctc cgcgctgccc ggcggctgtg agcgctgcgg gcgcggcgcg    1140
gggctttgtg cgctccgcag tgtgcgcgag gggagcgcgg ccggggcggg tgccccgcgg    1200
tgcggggggg gctgcgaggg gaacaaaggc tgcgtgcggg gtgtgtgcgt gggggggtga    1260
```

```
gcaggggtg tgggcgcgtc ggtcgggctg caaccccccc tgcaccccc tccccgagtt    1320 gctgagcacg gcccggcttc gggtgcgggg ctccgtacgg ggcgtggcgc ggggctcgcc    1380
gtgccgggcg gggggtggcg gcaggtgggg gtgccgggcg gggcggggcc gcctcgggcc    1440
ggggagggct cggggagggg gcgcggcggc ccccggagcg ccggcggctg tcgaggcgcg    1500
gcgagccgca gccattgcct tttatggtaa tcgtgcgaga gggcgcaggg acttcctttg    1560
tcccaaatct gtgcggagcc gaaatctggg aggcgccgcc gcaccccctc tagcgggcgc    1620
ggggcgaagc ggtgcggcgc cggcaggaag gaaatgggcg gggagggcct tcgtgcgtcg    1680
ccgcgccgcc gtccccttct ccctctccag cctcggggct gtccgcgggg ggacggctgc    1740 cttcggggg gacggggcag ggcggggttc ggcttctggc gtgtgaccgg cggctctaga    1800
caattgtact aaccttcttc tctttcctct cctgacaggt tggtgtacac tagcggccga    1860
atagagacca ttttcaaaa caatgggaga acgagcaggc agccctggta cggaccagga    1920
acgcaaggcg gggaaacacc actatagcta tttgtcagac tttgagacac cgcagagctc    1980
gggtcggtca tccttggtgt cgtcaagccc ggctagcgtc cggcgaaaga atccaaagcg    2040
ccaaacgtca gatggccagg tgcatcatca ggctccccgg aaaccctcgc ccaaaggatt    2100
gccgaacaga aagggggtcc gggtagggtt tagatcgcag agcctgaatc gcgagcctct    2160
tagaaaagat acagaccttg tgactaagag gattctgtcg gcacgactgt tgaagattaa    2220
cgaacttcag aatgaggtgt cagaactcca agtaaaactt gcggaactgc ttaaggagaa    2280
caaatcgctc aagcggcttc agtatcgcca agagaaagcg ctcaacaagt tcgaggacgc    2340
ggaaaacgag atttcgcagt tgatctttag gcataacaac gagatcaccg cccttaaaga    2400
acgcttgcgc aaaagccagg agaaagaacg cgccacggag aagagggtca aggacaccga    2460
atcggaactg tttagaacta agttttcgct tcaaaagctt aaagaaatct cggaagcgag    2520
gcatctccct gagcgagatg atttggctaa gaaacttgta tcggcagagc tcaaattgga    2580
tgatacggag aggaggatta aggaacttag caaaaacctt gaattgtcaa cgaactcgtt    2640
tcaacggcag ctgttggccg aaagaaaacg ggcttatgaa gcgcacgatg aaaacaaggt    2700
gctgcagaaa gaggtgcaga ggttgtacca taagctgaaa gagaaggaaa gagagctgga    2760
catcaaaaac atctacagca accggctgcc taagtcatcg ccaaacaaag agaaagagct    2820
ggcattgaga aagaatgcag cctgccagtc ggattttgcg gatctgtgca cgaaaggagt    2880
acagaccatg gaggacttta gcccgaagaa ataccacttt acacccgaga caatcatgtg    2940
ttacgagaac aagtgggagg agccgggaca ccttactctt gatctccaga gccaaaaaca    3000
ggatcgccac ggcgaggccg gtattctcaa cccgatcatg gagagagagg agaagttcgt    3060
cacagatgag gagctccacg tcgtgaaaca agaagtggag aagctcgagg acgaatggga    3120
acgagaagag cttgataaga agcagaagga gaaagcatcg ttgctggaac gcgaagagaa    3180
accggagtgg gagactggga ggtatcagct tgggatgtac ccaattcaga atatggacaa    3240
actccagggg gaggaagaag agaggctcaa gagggaaatg ctcctggcca agttgaatga    3300
gattgaccgg gagttgcaag actcacgcaa cctcaagtac cctgtactcc ccctgcttcc    3360
ggattttgaa tcaaaacttc actcccccga acggagcccc aagacctatc gattctcgga    3420
atcgtcggag agactcttca atggacacca tttgcaagac atctccttt caacacccaa    3480 agggaaggc cagaattccg gaaatgtgcg gtcgccagcg tcgccaaatg agttcgcatt    3540
cggttcgtac gtgccctcat tcgcgaaaac ctcggagaga tccaaccccct tcagccaaaa    3600
```

```
gtcgtcattc ttggatttcc agagaaactc catggaaaag ctctccaagg atggagtcga    3660
tctcatcact agaaaagaga agaaggccaa tctcatggaa cagttgttcg gagcgtcggg    3720
ttcgtccacc atctcctcca agtcatcaga ccccaattcg gtcgcatcct caagggaga    3780 catcgaccct tgaatttcc tgccgggaaa caagggttcg cgagatcagg aacatgacga    3840
ggacgagggg ttttcttgt ccgaagggag gtccttcaat ccgaatcgcc acagattgaa    3900
acacgcggat gacaagcctg cggtgaaggc tgcggactca gtagaggacg agatcgagga    3960
agtggccctg agatgatcag gatctgcctc gactgtgcct tctagttgcc agccatctgt    4020
tgtttgcccc tccccgtgc cttccttgac cctggaaggt gccactccca ctgtcctttc    4080
ctaataaaat gaggaaattg catcgcattg tctgagtagg tgtcattcta ttctgggggg    4140
tggggtgggg caggacagca aggggagga ttgggaagac aatagcaggc atgctgggga    4200
ctcgagttct acgtagataa gtagcatggc gggttaatca ttaactacaa ggaacccta    4260 gtgatgagt tggccactcc ctctctgcgc gctcgctcgc tcactgaggc cgggcgacca    4320
aaggtcgccc gacgccggg cttgtcccgg gcggcctcag tgagcgagcg agcgcgcagc    4380
cttaattaac ctaaggaaaa tgaagtgaag ttcctatact ttctagagaa taggaacttc    4440
tatagtgagt cgaataaggg cgacacaaaa tttattctaa atgcataata aatactgata    4500
acatcttata gtttgtatta tattttgtat tatcgttgac atgtataatt ttgatatcaa    4560
aaactgattt tcccttatt attttcgaga tttattttct taattctctt taacaaacta    4620
gaaatattgt atatacaaaa aatcataaat aatagatgaa tagtttaatt ataggtgttc    4680
atcaatcgaa aaagcaacgt atcttattta aagtgcgttg cttttttctc atttataagg    4740
ttaaataatt ctcatatatc aagcaaagtg acaggcgccc ttaaatattc tgacaaatgc    4800
tctttcccta aactcccccc ataaaaaaac ccgccgaagc gggtttttac gttatttgcg    4860
gattaacgat tactcgttat cagaaccgcc caggggcccc gagcttaacc ttttttattg    4920
ggggagaggg aagtcatgaa aaaactaacc tttgaaattc gatctccagc acatcagcaa    4980
aacgctattc acgcagtaca gcaaatcctt ccagacccaa ccaaaccaat cgtagtaacc    5040
attcaggaac gcaaccgcag cttagaccaa aacaggaagc tatgggcctg cttaggtgac    5100
gtctctcgtc aggttgaatg gcatggtcgc tggctggatg cagaaagctg gaagtgtgtg    5160
tttaccgcag cattaaagca gcaggatgtt gttcctaacc ttgccgggaa tggctttgtg    5220
gtaataggcc agtcaaccag caggatgcgt gtaggcgaat ttgcggagct attagagctt    5280
atacaggcat tcggtacaga gcgtggcgtt aagtggtcag acgaagcgag actggctctg    5340
gagtggaaag cgagatgggg agacagggct gcatgataaa tgtcgttagt ttctccggtg    5400
gcaggacgtc agcatatttg ctctggctaa tggagcaaaa gcgacgggca ggtaaagacg    5460
tgcattacgt tttcatggat acaggttgtg aacatccaat gacatatcgg tttgtcaggg    5520
aagttgtgaa gttctgggat ataccgctca ccgtattgca ggttgatatc aacccggagc    5580
ttggacagcc aaatggttat acggtatggg aaccaaagga tattcagacg cgaatgcctg    5640
ttctgaagcc atttatcgat atggtaaaga aatatggcac tccatacgtc ggcggcgcgt    5700
tctgcactga cagattaaaa ctcgttccct tcaccaaata ctgtgatgac catttcgggc    5760
gagggaatta caccacgtgg attggcatca gagctgatga accgaagcgg ctaaagccaa    5820
agcctggaat cagatatctt gctgaactgt cagactttga gaaggaagat atcctcgcat    5880 ggtgaagca acaccattc gatttgcaaa taccggaaca tctcggtaac tgcatattct    5940
gcattaaaaa atcaacgcaa aaaatcggac ttgcctgcaa agatgaggag ggattgcagc    6000
```

```
gtgttttaa tgaggtcatc acgggatccc atgtgcgtga cggacatcgg gaaacgccaa    6060
aggagattat gtaccgagga agaatgtcgc tggacggtat cgcgaaaatg tattcagaaa    6120
atgattatca agccctgtat caggacatgg tacgagctaa agattcgat accggctctt     6180 gttctgagtc atgcgaaata tttggagggc agcttgattt cgacttcggg agggaagctg    6240
catgatgcga tgttatcggt gcggtgaatg caaagaagat aaccgcttcc gaccaaatca    6300
accttactgg aatcgatggt gtctccggtg tgaaagaaca ccaacagggg tgttaccact    6360
accgcaggaa aaggaggacg tgtggcgaga cagcgacgaa gtatcaccga cataatctgc    6420
gaaaactgca ataccttcc aacgaaacgc accagaaata acccaagcc atcccaaaa      6480 gaatctgacg taaaaacctt caactacacg gctcacctgt gggatatccg gtggctaaga    6540
cgtcgtgcga ggaaaacaag gtgattgacc aaaatcgaag ttacgaacaa gaaagcgtcg    6600
agcgagcttt aacgtgcgct aactgcggtc agaagctgca tgtgctggaa gttcacgtgt    6660
gtgagcactg ctgcgcagaa ctgatgagcg atccgaatag ctcgatgcac gaggaagaag    6720
atgatggcta aaccagcgcg aagacgatgt aaaaacgatg aatgccggga atggtttcac    6780
cctgcattcg ctaatcagtg gtggtgctct ccagagtgtg gaaccaagat agcactcgaa    6840
cgacgaagta aagaacgcga aaaagcggaa aaagcagcag agaagaaacg acgacgagag    6900
gagcagaaac agaagataa acttaagatt cgaaaactcg ccttaaagcc ccgcagttac     6960
tggattaaac aagcccaaca agccgtaaac gccttcatca gagaaagaga ccgcgactta    7020
ccatgtatct cgtgcggaac gctcacgtct gctcagtggg atgccggaca ttaccggaca    7080
actgctgcgg cacctcaact ccgatttaat gaacgcaata ttcacaagca atgcgtggtg    7140
tgcaaccagc acaaaagcgg aaatctcgtt ccgtatcgcg tcgaactgat tagccgcatc    7200
gggcaggaag cagtagacga aatcgaatca aaccataacc gccatcgctg gactatcgaa    7260
gagtgcaagg cgatcaaggc agagtaccaa cagaaactca aagacctgcg aaatagcaga    7320
agtgaggccg catgacgttc tcagtaaaaa ccattccaga catgctcgtt gaagcatacg    7380
gaaatcagac agaagtagca cgcagactga aatgtagtcg cggtacggtc agaaaatacg    7440
ttgatgataa agacgggaaa atgcacgcca tcgtcaacga cgttctcatg gttcatcgcg    7500
gatggagtga aagagatgcg ctattacgaa aaaattgatg gcagcaaata ccgaaatatt    7560
tgggtagttg gcgatctgca cggatgctac acgaacctga tgaacaaact ggatacgatt    7620
ggattcgaca acaaaaaaga cctgcttatc tcggtgggcg atttggttga tcgtggtgca    7680
gagaacgttg aatgcctgga attaatcaca ttccccctggt tcagagctgt acgtggaaac    7740
catgagcaaa tgatgattga tggcttatca gagcgtggaa acgttaatca ctggctgctt    7800 aatgcggtg ctggttctt taatctcgat tacgacaaag aaattctggc taaagctctt     7860
gcccataaag cagatgaact tccgttaatc atcgaactgg tgagcaaaga taaaaaatat    7920
gttatctgcc acgccgatta tccctttgac gaatacgagt ttggaaagcc agttgatcat    7980
cagcaggtaa tctggaaccg cgaacgaatc agcaactcac aaaacgggat cgtgaaagaa    8040
atcaaaggcg cggacacgtt catctttggt catacgccag cagtgaaacc actcaagttt    8100
gccaaccaaa tgtatatcga taccggcgca gtgttctgcg gaaacctaac attgattcag    8160
gtacagggag aaggcgcatg agactcgaaa gcgtagctaa atttcattcg ccaaaaagcc    8220
cgatgatgag cgactcacca cgggccacgg cttctgactc tctttccggt actgatgtga    8280
tggctgctat ggggatggcg caatcacaag ccggattcgg tatggctgca ttctgcggta    8340
```

```
agcacgaact cagccagaac gacaaacaaa aggctatcaa ctatctgatg caatttgcac      8400
acaaggtatc ggggaaatac cgtggtgtgg caaagcttga aggaaatact aaggcaaagg      8460
tactgcaagt gctcgcaaca ttcgcttatg cggattattg ccgtagtgcc gcgacgccgg      8520
gggcaagatg cagagattgc catggtacag gccgtgcggt tgatattgcc aaaacagagc      8580 tgtggggag agttgtcgag aaagagtgcg gaagatgcaa aggcgtcggc tattcaagga       8640
tgccagcaag cgcagcatat cgcgctgtga cgatgctaat cccaaaccttt acccaaccca     8700 cctggtcacg cactgttaag ccgctgtatg acgctctggt ggtgcaatgc cacaaagaag      8760
agtcaatcgc agacaacatt ttgaatgcgt tcacacgtta gcagcatgat tgccacggat      8820
ggcaacatat taacggcatg atattgactt attgaataaa attgggtaaa tttgactcaa      8880
cgatgggtta attcgctcgt tgtggtagtg agatgaaaag aggcggcgct tactaccgat      8940
tccgcctagt tggtcacttc gacgtatcgt ctggaactcc aaccatcgca ggcagagagg      9000
tctgcaaaat gcaatcccga aacagttcgc aggtaatagt tagagcctgc ataacggttt      9060
cgggattttt tatatctgca caacaggtaa gagcattgag tcgataatcg tgaagagtcg      9120
gcgagcctgg ttagccagtg ctcttttccgt tgtgctgaat taagcgaata ccggaagcag      9180
aaccggatca ccaaatgcgt acaggcgtca tcgccgccca gcaacagcac aacccaaact      9240
gagccgtagc cactgtctgt cctgaattca ttagtaatag ttacgctgcg gccttttaca      9300
catgaccttc gtgaaagcgg gtggcaggag gtcgcgctaa caacctcctg ccgttttgcc      9360
cgtgcatatc ggtcacgaac aaatctgatt actaaacaca gtagcctgga tttgttctat      9420
cagtaatcga ccttattcct aattaaatag agcaaatccc cttattgggg gtaagacatg      9480
aagatgccag aaaaacatga cctgttggcc gccattctcg cggcaaagga acaaggcatc      9540
ggggcaatcc ttgcgtttgc aatggcgtac cttcgcggca gatataatgg cggtgcgttt      9600
acaaaaacag taatcgacgc aacgatgtgc gccattatcg cctggttcat tcgtgacctt      9660
ctcgacttcg ccggactaag tagcaatctc gcttatataa cgagcgtgtt tatcggctac      9720
atcggtactg actcgattgg ttcgcttatc aaacgcttcg ctgctaaaaa agccggagta      9780
gaagatggta gaaatcaata atcaacgtaa ggcgttcctc gatatgctgg cgtggtcgga      9840
gggaactgat aacggacgtc agaaaaccag aaatcatggt tatgacgtca ttgtaggcgg      9900
agagctattt actgattact ccgatcaccc tcgcaaactt gtcacgctaa acccaaaact      9960
caaatcaaca ggcgcttaag actggccgtc gttttacaac acagaaagag tttgtagaaa     10020
cgcaaaaagg ccatccgtca ggggccttct gcttagtttg atgcctggca gttcccctact    10080 ctcgccttcc gcttcctcgc tcactgactc gctgcgctcg gtcgttcggc tgcggcgagc     10140
ggtatcagct cactcaaagg cggtaatacg gttatccaca gaatcagggg ataacgcagg     10200
aaagaacatg tgagcaaaag gccagcaaaa ggccaggaac cgtaaaaagg ccgcgttgct     10260
ggcgtttttc cataggctcc gcccccctga cgagcatcac aaaaatcgac gctcaagtca     10320
gaggtggcga aacccgacag gactataaag ataccaggcg tttccccctg gaagctccct     10380
cgtgcgctct cctgttccga ccctgccgct taccggatac ctgtccgcct ttctcccttc     10440
gggaagcgtg gcgctttctc atagctcacg ctgtaggtat ctcagttcgg tgtaggtcgt     10500
tcgctccaag ctgggctgtg tgcacgaacc ccccgttcag cccgaccgct gcgccttatc     10560
cggtaactat cgtcttgagt ccaacccggt aagacacgac ttatcgccac tggcagcagc     10620
cactggtaac aggattagca gagcgaggta tgtaggcggt gctacagagt tcttgaagtg     10680
gtgggctaac tacggctaca ctagaagaac agtatttggt atctgcgctc tgctgaagcc     10740
```

```
agttaccttc ggaaaaagag ttggtagctc ttgatccggc aaacaaacca ccgctggtag    10800
cggtggtttt tttgtttgca agcagcagat tacgcgcaga aaaaaggat ctcaagaaga    10860 tcctttgatc ttttctacgg ggtctgacgc tcagtggaac gacgcgcgcg taactcacgt    10920
taagggattt tggtcatgag cttgcgccgt cccgtcaagt cagcgtaatg ctctgctttt    10980
agaaaaactc atcgagcatc aaatgaaact gcaatttatt catatcagga ttatcaatac    11040
catatttttg aaaagccgt ttctgtaatg aaggagaaaa ctcaccgagg cagttccata    11100
ggatggcaag atcctggtat cggtctgcga ttccgactcg tccaacatca atacaaccta    11160
ttaatttccc ctcgtcaaaa ataaggttat caagtgagaa atcaccatga gtgacgactg    11220
aatccggtga aatggcaaa agtttatgca tttctttcca gacttgttca acaggccagc    11280
cattacgctc gtcatcaaaa tcactcgcat caaccaaacc gttattcatt cgtgattgcg    11340
cctgagcgag gcgaaatacg cgatcgctgt taaaaggaca attacaaaca ggaatcgagt    11400
gcaaccggcg caggaacact gccagcgcat caacaatatt ttcacctgaa tcaggatatt    11460
cttctaatac ctggaacgct gttttttccgg ggatcgcagt ggtgagtaac catgcatcat    11520
caggagtacg gataaaatgc ttgatggtcg aagtggcat aaattccgtc agccagttta    11580
gtctgaccat ctcatctgta acatcattgg caacgctacc tttgccatgt ttcagaaaca    11640
actctggcgc atcgggcttc ccatacaagc gatagattgt cgcacctgat tgcccgacat    11700
tatcgcgagc ccatttatac ccatataaat cagcatccat gttggaattt aatcgcggcc    11760
tcgacgtttc ccgttgaata tggctcatat tcttcctttt tcaatattat tgaagcattt    11820
atcagggtta ttgtctcatg agcggataca tatttgaatg tatttagaaa aataaacaaa    11880 tagggggtcag tgttcaaacc aattaaccaa ttctgaacat tatcgcgagc ccatttatac    11940
ctgaatatgg ctcataacac cccttgtttg cctggcggca gtagcgcggt ggtcccacct    12000 gacccatgc cgaactcaga agtgaaacgc cgtagcgccg atggtagtgt ggggactccc    12060
catgcgagag tagggaactg ccaggcatca aataaaacga aaggctcagt cgaaagactg    12120
ggcctttcgc ccgggctaat taggggggtgt cgcccttatt cgactctata gtgaagttcc    12180
tattctctag aaagtatagg aacttctgaa gtggggtcga cttaattaag g              12231
```

<210> SEQ ID NO 9
<211> LENGTH: 12220
<212> TYPE: DNA
<213> ORGANISM: Artificial Sequence
<220> FEATURE:
<223> OTHER INFORMATION: constructed sequence

<400> SEQUENCE: 9

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
tagttattaa tagtaatcaa ttacggggtc attagttcat agcccatata tggagttccg     240
cgttacataa cttacggtaa atggcccgcc tggctgaccg cccaacgacc cccgcccatt     300
gacgtcaata atgacgtatg ttcccatagt aacgccaata gggactttcc attgacgtca     360
atgggtggag tatttacggt aaactgccca cttggcagta catcaagtgt atcatatgcc     420
aagtacgccc cctattgacg tcaatgacgg taaatggccc gcctggcatt atgcccagta     480
catgacctta tgggactttc ctacttggca gtacatctac gtattagtca tcgctattaa     540
```

```
catggtcgag gtgagcccca cgttctgctt cactctcccc atctcccccc cctcccacc     600 cccaattttg tatttattta ttttttaatt attttgtgca gcgatggggg cggggggggg    660 ggggggggcgc gcgccaggcg gggcggggcg gggcgagggg cggggcgggg cgaggcggag   720
aggtgcggcg gcagccaatc agagcggcgc gctccgaaag tttccttta tggcgaggcg     780 gcggcggcgg cggccctata aaagcgaag cgcgcggcgg cgggagtc gctgcgacgc      840 tgccttcgcc ccgtgcccg ctccgccgcc gcctcgcgcc gcccgcccg gctctgactg     900 accgcgttac tcccacaggt gagcgggcgg gacggcccct ctcctccggg ctgtaattag   960
cgcttggttt aatgacggct tgtttctttt ctgtggctgc gtgaaagcct tgagggctc    1020 cgggagggcc ctttgtgcgg ggggagcggc tcggggggtg cgtgcgtgtg tgtgtgcgtg   1080
gggagcgccg cgtgcggctc cgcgctgccc ggcggctgtg agcgctgcgg gcgcggcgcg   1140
gggctttgtg cgctccgcag tgtgcgcgag gggagcgcgg ccggggggcgg tgccccgcgg  1200 tgcggggggg gctgcgaggg gaacaaaggc tgcgtgcggg gtgtgtgcgt ggggggtga    1260 gcaggggggtg tgggcgcgtc ggtcgggctg caaccccccc tgcacccccc tccccgagtt  1320
gctgagcacg gcccggcttc gggtgcgggg ctccgtacgg ggcgtggcgc ggggctcgcc   1380
gtgccgggcg ggggtggcg gcaggtgggg gtgccgggcg gggcggggcc gcctcgggcc   1440
ggggagggct cggggggaggg gcgcggcggc ccccggagcg ccggcggctg tcgaggcgcg   1500
gcgagccgca gccattgcct tttatggtaa tcgtgcgaga gggcgcaggg acttcctttg    1560
tcccaaatct gtgcggagcc gaaatctggg aggcgccgcc gcacccctc tagcgggcgc     1620 ggggcgaagc ggtgcggcgc cggcaggaag gaaatgggcg gggagggcct tcgtgcgtcg    1680
ccgcgccgcc gtccccttct ccctctccag cctcggggct gtccgcgggg ggacggctgc    1740
cttcgggggg gacggggcag ggcgggggttc ggcttctggc gtgtgaccgg cggctctaga  1800
caattgtact aaccttcttc tctttcctct cctgacaggt tggtgtacac tagcggccgc    1860
caccatgggg gaaagagcag gaagtccagg tactgaccaa gaaagaaagg caggcaaaca   1920
ccattattct tacttatctg attttgaaac gccacagtct tctggccgat catcgctggt    1980
cagttcttca cctgcaagtg ttaggagaaa aaatcctaaa agacaaactt cagatggcca    2040
agtacatcac caagcccctc ggaaaccaag ccccaagggt ctaccaaaca gaaagggagt    2100
ccgagtggga tttcgctccc agagcctcaa tagagagcca cttcggaaag atactgatct    2160
tgttacaaaa cggattctgt ctgcaagact gctaaaaatc aatgagttgc agaatgaagt    2220
atctgaactc caggtcaagt tagctgagct gctaaaagaa aataaatctt tgaaaaggct    2280
tcagtacaga caggagaaag ccctgaataa gtttgaagat gccgaaaatg aaatctcaca    2340
acttatattt cgtcataaca atgagattac agcactcaaa aacgcttaa gaaaatctca    2400 agagaaagaa cgggcaactg agaaaagggt aaaagataca gaaagtgaac tatttaggac    2460
aaaattttcc ttacagaaac tgaaagagat ctctgaagct agacacctac ctgaacgaga    2520
tgatttggca aagaaactag tttcagcaga gttaaagtta gatgacaccg agagaagaat    2580
taaggagcta tcgaaaaacc ttgaactgag tactaacagt ttccaacgac agttgcttgc    2640
tgaaaggaaa agggcatatg aggctcatga tgaaaataaa gttcttcaaa aggaggtaca    2700
gcgactatat cacaaattaa aggaaagga gagagaactg gatataaaaa atatatattc    2760
taatcgtctg ccaaagtcct ctccaaataa agagaaagaa cttgcattaa gaaaaaatgc    2820
tgcatgccag agtgattttg cagacctgtg tacaaaagga gtacaaaacca tggaagactt   2880 caagccagaa gaatatcctt taactccaga aacaattatg tgttacgaaa acaaatggga    2940
```

```
agaaccagga catcttactt tggacttgca atctcaaaag caagacaggc atggagaagc    3000
agggattcta aacccaatta tggaaagaga agaaaaattt gttacagatg aagaactcca    3060
tgtcgtaaaa caggaggttg aaaagctgga ggatgaatgg gaaagagaag aacttgataa    3120
aaagcaaaaa gaaaaggcat ctttactgga agagaagaa aagccagagt gggaaactgg     3180
aaggtaccaa ctaggaatgt atccaattca gaatatggat aaattgcaag gagaggaaga    3240
agaaagactg aagagagaaa tgctacttgc taaactgaat gaaattgaca gagaactcca    3300
agattctcga aatctaaaat accctgtttt gccattgtta cctgattttg aatcaaaact    3360
acactcccca gagagaagcc ccaaaacata caggttctct gaatcctcag agagattatt    3420
taatgggcat catttgcaag acatcagttt ctcaactcca aaaggagaag gtcagaattc    3480
aggaaatgtt agaagtccag cctcccctaa tgagttcgca tttggtagct acgtgccttc    3540
gtttgcaaaa acatcagaga ggtcaaatcc atttagtcaa aaaagtagtt ttttggattt    3600
ccaaagaaac agtatggaaa aacttagtaa agatggtgta gatttaatta caagaaaaga    3660
gaaaaaagct aatttgatgg aacagttatt tggtgccagt ggtagcagca ccatttcctc    3720
caaaagcagt gacccaaatt ctgtggcttc cagtaaagga gacattgacc ctctaaattt    3780
tctccctggg aataaaggca gcagagatca agaacatgat gaagatgaag ctttttcct    3840 cagtgaagga agaagttta atccaaatag gcaccgatta aaacatgcag acgataaacc    3900
agcagtaaaa gcagctgatt ctgtagaaga tgaaattgaa gaagtagcac tgagatgatc    3960
ataactgcag atctgcctcg actgtgcctt ctagttgcca gccatctgtt gtttgcccct    4020
cccccgtgcc ttccttgacc ctggaaggtg ccactcccac tgtcctttcc taataaaatg    4080
aggaaattgc atcgcattgt ctgagtaggt gtcattctat tctgggggt ggggtggggc     4140 aggacagcaa gggggaggat tgggaagaca atagcaggca tgctgggac tcgagttcta     4200 cgtagataag tagcatggcg ggttaatcat taactacaag gaaccctag tgatggagtt     4260 ggccactccc tctctgcgcg ctcgctcgct cactgaggcc gggcgaccaa aggtcgcccg    4320
acgcccgggc tttgcccggg cggcctcagt gagcgagcga gcgcgcagcc ttaattaacc    4380
taaggaaaat gaagtgaagt tcctatactt tctagagaat aggaacttct atagtgagtc    4440
gaataagggc gacacaaaat ttattctaaa tgcataataa atactgataa catcttatag    4500
tttgtattat attttgtatt atcgttgaca tgtataattt tgatatcaaa aactgatttt    4560
cccttattta tttcgagat ttatttctt aattctcttt aacaaactag aaatattgta      4620
tatacaaaaa atcataaata atagatgaat agtttaatta taggtgttca tcaatcgaaa    4680
aagcaacgta tcttatttaa agtgcgttgc ttttttctca tttataaggt taaataattc    4740
tcatatatca agcaaagtga caggcgcccct taaatattct gacaaatgct ctttccctaa    4800
actcccccca taaaaaaacc cgccgaagcg ggttttttacg ttatttgcgg attaacgatt    4860
actcgttatc agaaccgccc aggggcccg agcttaacct tttttatttgg gggagaggga    4920 agtcatgaaa aaactaacct ttgaaattcg atctccagca catcagcaaa acgctattca    4980
cgcagtacag caaatccttc cagacccaac caaaccaatc gtagtaacca ttcaggaacg    5040
caaccgcagc ttagaccaaa acaggaagct atgggcctgc ttaggtgacg tctctcgtca    5100
ggttgaatgg catggtcgct ggctggatgc agaaagctgg aagtgtgtgt ttaccgcagc    5160
attaaagcag caggatgttg ttcctaacct tgccgggaat ggctttgtgg taataggcca    5220
gtcaaccagc aggatgcgtg taggcgaatt tgcggagcta ttagagctta tacaggcatt    5280
```

```
cggtacagag cgtggcgtta agtggtcaga cgaagcgaga ctggctctgg agtggaaagc      5340
gagatgggga gacagggctg catgataaat gtcgttagtt tctccggtgg caggacgtca      5400
gcatatttgc tctggctaat ggagcaaaag cgacgggcag gtaaagacgt gcattacgtt      5460
ttcatggata caggttgtga acatccaatg acatatcggt ttgtcaggga agttgtgaag      5520
ttctgggata taccgctcac cgtattgcag gttgatatca acccggagct tggacagcca      5580
aatggttata cggtatggga accaaaggat attcagacgc gaatgcctgt tctgaagcca      5640
tttatcgata tggtaaagaa atatggcact ccatacgtcg gcggcgcgtt ctgcactgac      5700
agattaaaac tcgttccctt caccaaatac tgtgatgacc atttcgggcg agggaattac      5760
accacgtgga ttggcatcag agctgatgaa ccgaagcggc taaagccaaa gcctggaatc      5820
agatatcttg ctgaactgtc agactttgag aaggaagata tcctcgcatg gtggaagcaa      5880
caaccattcg atttgcaaat accggaacat ctcggtaact gcatattctg cattaaaaaa      5940
tcaacgcaaa aaatcggact tgcctgcaaa gatgaggagg gattgcagcg tgttttttaat     6000 gaggtcatca cgggatccca tgtgcgtgac ggacatcggg aaacgccaaa ggagattatg      6060
taccgaggaa gaatgtcgct ggacggtatc gcgaaaatgt attcagaaaa tgattatcaa      6120
gccctgtatc aggacatggt acgagctaaa agattcgata ccggctcttg ttctgagtca      6180
tgcgaaatat ttggagggca gcttgatttc gacttcggga gggaagctgc atgatgcgat      6240
gttatcggtg cggtgaatgc aaagaagata accgcttccg accaaatcaa ccttactgga      6300
atcgatggtg tctccggtgt gaagaacac caacaggggt gttaccacta ccgcaggaaa       6360
aggaggacgt gtggcgagac agcgacgaag tatcaccgac ataatctgcg aaaactgcaa      6420
ataccttcca acgaaacgca ccagaaataa acccaagcca atcccaaaag aatctgacgt      6480
aaaaaccttc aactcacacgg ctcacctgtg ggatatccgg tggctaagac gtcgtgcgag     6540
gaaaacaagg tgattgacca aaatcgaagt tacgaacaag aaagcgtcga gcgagcttta      6600
acgtgcgcta actgcggtca gaagctgcat gtgctggaag ttcacgtgtg tgagcactgc      6660
tgcgcagaac tgatgagcga tccgaatagc tcgatgcacg aggaagaaga tgatggctaa      6720
accagcgcga agacgatgta aaaacgatga atgccgggaa tggtttcacc ctgcattcgc      6780
taatcagtgg tggtgctctc cagagtgtgg aaccaagata gcactcgaac gacgaagtaa      6840
agaacgcgaa aaagcggaaa aagcagcaga gaagaaacga cgacgagagg agcagaaaca      6900
gaaagataaa cttaagattc gaaaactcgc cttaaagccc cgcagttact ggattaaaca      6960
agcccaacaa gccgtaaacg ccttcatcag agaaagagac cgcgacttac catgtatctc      7020
gtgcggaacg ctcacgtctg ctcagtggga tgccggacat taccggacaa ctgctgcggc      7080
acctcaactc cgatttaatg aacgcaatat tcacaagcaa tgcgtggtgt gcaaccagca      7140
caaaagcgga aatctcgttc cgtatcgcgt cgaactgatt agccgcatcg ggcaggaagc      7200
agtagacgaa atcgaatcaa accataaccg ccatcgctgg actatcgaag agtgcaaggc      7260
gatcaaggca gagtaccaac agaaactcaa agacctgcga aatagcagaa gtgaggccgc      7320
atgacgttct cagtaaaaac cattccagac atgctcgttg aagcatacgg aaatcagaca      7380
gaagtagcac gcagactgaa atgtagtcgc ggtacggtca gaaaatacgt tgatgataaa      7440
gacgggaaaa tgcacgccat cgtcaacgac gttctcatgg ttcatcgcgg atggagtgaa      7500
agagatgcgc tattacgaaa aaattgatgg cagcaaatac cgaaatattt gggtagttgg      7560
cgatctgcac ggatgctaca cgaacctgat gaacaaactg gatacgattg gattcgacaa      7620
caaaaaagac ctgcttatct cggtgggcga tttggttgat cgtggtgcag agaacgttga      7680
```

```
atgcctggaa ttaatcacat tccactggtt cagagctgta cgtggaaacc atgagcaaat    7740
gatgattgat ggcttatcag agcgtggaaa cgttaatcac tggctgctta atggcggtgg    7800
ctggttcttt aatctcgatt acgacaaaga aattctggct aaagctcttg cccataaagc    7860
agatgaactt ccgttaatca tcgaactggt gagcaaagat aaaaaatatg ttatctgcca    7920
cgccgattat ccctttgacg aatacgagtt tggaaagcca gttgatcatc agcaggtaat    7980
ctggaaccgc gaacgaatca gcaactcaca aaacgggatc gtgaaagaaa tcaaaggcgc    8040
ggacacgttc atctttggtc atacgccagc agtgaaacca ctcaagtttg ccaaccaaat    8100
gtatatcgat accggcgcag tgttctgcgg aaacctaaca ttgattcagg tacagggaga    8160
aggcgcatga gactcgaaag cgtagctaaa tttcattcgc caaaaagccc gatgatgagc    8220
gactcaccac gggccacggc ttctgactct ctttccggta ctgatgtgat ggctgctatg    8280
gggatggcgc aatcacaagc cggattcggt atggctgcat tctgcggtaa gcacgaactc    8340
agccagaacg acaaacaaaa ggctatcaac tatctgatgc aatttgcaca caaggtatcg    8400
gggaaatacc gtggtgtggc aaagcttgaa ggaaatacta aggcaaaggt actgcaagtg    8460
ctcgcaacat tcgcttatgc ggattattgc cgtagtgccg cgacgccggg ggcaagatgc    8520
agagattgcc atggtacagg ccgtgcggtt gatattgcca aaacagagct gtgggggaga    8580
gttgtcgaga aagagtgcgg aagatgcaaa ggcgtcggct attcaaggat gccagcaagc    8640
gcagcatatc gcgctgtgac gatgctaatc ccaaaccta cccaacccac ctggtcacgc    8700
actgttaagc cgctgtatga cgctctggtg gtgcaatgcc acaaagaaga gtcaatcgca    8760
gacaacattt tgaatgcggt cacacgttag cagcatgatt gccacggatg caacatatt    8820
aacggcatga tattgactta ttgaataaaa ttgggtaaat ttgactcaac gatgggttaa    8880
ttcgctcgtt gtggtagtga gatgaaaaga ggcggcgctt actaccgatt ccgcctagtt    8940
ggtcacttcg acgtatcgtc tggaactcca accatcgcag gcagagaggt ctgcaaaatg    9000
caatcccgaa acagttcgca ggtaatagtt agagcctgca taacggtttc gggatttttt    9060
atatctgcac aacaggtaag agcattgagt cgataatcgt gaagagtcgg cgagcctggt    9120
tagccagtgc tctttccgtt gtgctgaatt aagcgaatac cggaagcaga accggatcac    9180
caaatgcgta caggcgtcat cgccgcccag caacagcaca acccaaactg agccgtagcc    9240
actgtctgtc ctgaattcat tagtaatagt tacgctgcgg ccttttacac atgaccttcg    9300
tgaaagcggg tggcaggagg tcgcgctaac aacctcctgc cgttttgccc gtgcatatcg    9360
gtcacgaaca aatctgatta ctaaacacag tagcctggat ttgttctatc agtaatcgac    9420
cttattccta attaaataga gcaaatcccc ttattggggg taagacatga agatgccaga    9480
aaaacatgac ctgttggccg ccattctcgc ggcaaaggaa caaggcatcg ggcaatcct    9540
tgcgtttgca atggcgtacc ttcgcggcag atataatggc ggtgcgttta caaaaacagt    9600
aatcgacgca acgatgtgcg ccattatcgc ctggttcatt cgtgaccttc tcgacttcgc    9660
cggactaagt agcaatctcg cttatataac gagcgtgttt atcggctaca tcggtactga    9720
ctcgattggt tcgcttatca aacgcttcgc tgctaaaaaa gccggagtag aagatggtag    9780
aaatcaataa tcaacgtaag gcgttcctcg atatgctggc gtggtcggag ggaactgata    9840
acggacgtca gaaaaccaga aatcatggtt atgacgtcat tgtaggcgga gagctattta    9900
ctgattactc cgatcacct cgcaaacttg tcacgctaaa cccaaaactc aaatcaacag    9960
gcgcttaaga ctggccgtcg ttttacaaca cagaaagagt ttgtagaaac gcaaaaaggc    10020
```

```
catccgtcag gggccttctg cttagtttga tgcctggcag ttccctactc tcgccttccg    10080
cttcctcgct cactgactcg ctgcgctcgg tcgttcggct gcggcgagcg gtatcagctc    10140
actcaaaggc ggtaatacgg ttatccacag aatcagggga taacgcagga agaacatgt    10200 gagcaaaagg ccagcaaaag gccaggaacc gtaaaaaggc cgcgttgctg gcgttttttcc   10260 ataggctccg cccccctgac gagcatcaca aaaatcgacg ctcaagtcag aggtggcgaa    10320
acccgacagg actataaaga taccaggcgt ttccccctgg aagctccctc gtgcgctctc    10380
ctgttccgac cctgccgctt accggatacc tgtccgcctt tctcccttcg ggaagcgtgg    10440
cgctttctca tagctcacgc tgtaggtatc tcagttcggt gtaggtcgtt cgctccaagc    10500
tgggctgtgt gcacgaaccc cccgttcagc ccgaccgctg cgccttatcc ggtaactatc    10560
gtcttgagtc caacccggta agacacgact tatcgccact ggcagcagcc actggtaaca    10620
ggattagcag agcgaggtat gtaggcggtg ctacagagtt cttgaagtgg tgggctaact    10680
acggctacac tagaagaaca gtatttggta tctgcgctct gctgaagcca gttaccttcg    10740
gaaaaagagt tggtagctct tgatccggca aacaaaccac cgctggtagc ggtggttttt    10800
ttgtttgcaa gcagcagatt acgcgcagaa aaaaaggatc tcaagaagat cctttgatct    10860
tttctacggg gtctgacgct cagtggaacg acgcgcgcgt aactcacgtt aagggatttt    10920
ggtcatgagc ttgcgccgtc ccgtcaagtc agcgtaatgc tctgctttta gaaaaactca    10980
tcgagcatca aatgaaactg caattttattc atatccaggat tatcaataac atattttttga   11040 aaaagccgtt tctgtaatga aggagaaaac tcaccgaggc agttccatag gatggcaaga    11100
tcctggtatc ggtctgcgat tccgactcgt ccaacatcaa tacaacctat taatttcccc    11160
tcgtcaaaaa taaggttatc aagtgagaaa tcaccatgag tgacgactga atccggtgag    11220
aatggcaaaa gtttatgcat ttctttccag acttgttcaa caggccagcc attacgctcg    11280
tcatcaaaat cactcgcatc aaccaaaccg ttattcattc gtgattgcgc ctgagcgagg    11340
cgaaatacgc gatcgctgtt aaaaggacaa ttacaaacag gaatcgagtg caaccggcgc    11400
aggaacactg ccagcgcatc aacaatattt tcacctgaat caggatattc ttctaatacc    11460
tggaacgctg ttttttccggg gatcgcagtg gtgagtaacc atgcatcatc aggagtacgg    11520
ataaaatgct tgatggtcgg aagtggcata aattccgtca gccagtttag tctgaccatc    11580
tcatctgtaa catcattggc aacgctacct ttgccatgtt tcagaaacaa ctctggcgca    11640
tcgggcttcc catacaagcg atagattgtc gcacctgatt gcccgacatt atcgcgagcc    11700
catttatacc catataaatc agcatccatg ttggaattta atcgcggcct cgacgtttcc    11760
cgttgaatat ggctcatatt cttccttttt caatattatt gaagcattta tcagggttat    11820
tgtctcatga gcggatacat atttgaatgt atttagaaaa ataaacaaat aggggtcagt    11880
gttacaacca attaaccaat tctgaacatt atcgcgagcc catttatacc tgaatatggc    11940
tcataacacc ccttgtttgc ctggcggcag tagcgcggtg gtcccacctg acccatgcc    12000 gaactcagaa gtgaaacgcc gtagcgccga tggtagtgtg gggactcccc atgcgagagt    12060
agggaactgc caggcatcaa ataaaacgaa aggctcagtc gaaagactgg gcctttcgcc    12120
cgggctaatt aggggggtgtc gcccttattc gactctatag tgaagttcct attctctaga    12180
aagtatagga acttctgaag tggggtcgac ttaattaagg                          12220
```

<210> SEQ ID NO 10
<211> LENGTH: 583
<212> TYPE: DNA
<213> ORGANISM: Artificial Sequence
<220> FEATURE:
<223> OTHER INFORMATION: constructed sequence

<400> SEQUENCE: 10

| | | | | | |
|---|---|---|---|---|---|
| cgttacataa | cttacggtaa | atggcccgcc | tggctgaccg | cccaacgacc | cccgcccatt | 60 |
| gacgtcaata | atgacgtatg | ttcccatagt | aacgccaata | gggactttcc | attgacgtca | 120 |
| atgggtggag | tatttacggt | aaactgccca | cttggcagta | catcaagtgt | atcatatgcc | 180 |
| aagtacgccc | cctattgacg | tcaatgacgg | taaatggccc | gcctggcatt | atgcccagta | 240 |
| catgacctta | tgggactttc | ctacttggca | gtacatctac | gtattagtca | tcgctattaa | 300 |
| catggtcgag | gtgagcccca | cgttctgctt | cactctcccc | atctcccccc | cctccccacc | 360 |
| cccaattttg | tatttattta | ttttttaatt | attttgtgca | gcgatggggg | cggggggggg | 420 |
| ggggggggcgc | gcgccaggcg | gggcggggcg | gggcgagggg | cggggcgggg | cgaggcggag | 480 |
| aggtgcggcg | gcagccaatc | agagcggcgc | gctccgaaag | tttcctttta | tggcgaggcg | 540 |
| gcggcggcgg | cggccctata | aaaagcgaag | cgcgcggcgg | gcg | | 583 |

<210> SEQ ID NO 11
<211> LENGTH: 2238
<212> TYPE: DNA
<213> ORGANISM: Artificial Sequence
<220> FEATURE:
<223> OTHER INFORMATION: constructed sequence

<400> SEQUENCE: 11

| | | | | | |
|---|---|---|---|---|---|
| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | gcataaggac | 120 |
| gacagcaggg | gtcttgtgct | tcctgggtac | aagtacctcg | gacccttcaa | cggactcgac | 180 |
| aagggagagc | cggtcaacga | ggcagacgcc | gcggccctcg | agcacgacaa | agcctatgac | 240 |
| cggcagctcg | acagcggaga | caacccgtac | ctcaagtaca | accacgccga | cgcggagttt | 300 |
| caggagcgcc | ttaaagaaga | tacgtctttt | gggggcaacc | tcggacgagc | agtcttccag | 360 |
| gcgaaaaaga | gggttcttga | acctctgggc | ctggttgagg | aacctgttaa | gacggctccg | 420 |
| ggaaaaaaga | ggccggtaga | gcactctcct | gtggagccag | actcctcctc | gggaaccgga | 480 |
| aaggcgggcc | agcagcctgc | aagaaaaaga | ttgaattttg | gtcagactgg | agacgcagac | 540 |
| tcagtacctg | accccagcc | tctcggacag | ccaccagcag | cccctctgg | tctgggaact | 600 |
| aatacgatgg | ctacaggcag | tggcgcacca | atggcagaca | ataacgaggg | cgccgacgga | 660 |
| gtgggtaatt | cctcgggaaa | ttggcattgc | gattccacat | ggatgggcga | cagagtcacc | 720 |
| accaccagca | cccgaacctg | ggccctgccc | acctacaaca | accacctcta | caaacaaatt | 780 |
| tccagccaat | caggagcctc | gaacgacaat | cactactttg | gctacagcac | cccttggggg | 840 |
| tattttgact | tcaacagatt | ccactgccac | ttttcaccac | gtgactggca | aagactcatc | 900 |
| aacaacaact | ggggattccg | acccaagaga | ctcaacttca | agctctttaa | cattcaagtc | 960 |
| aaagaggtca | cgcagaatga | cggtacgacg | acgattgcca | ataaccttac | cagcacggtt | 1020 |
| caggtgttta | ctgactcgga | gtaccagctc | ccgtacgtcc | tcggctcggc | gcatcaagga | 1080 |
| tgcctcccgc | cgttcccagc | agacgtcttc | atggtgccac | agtatggata | cctcaccctg | 1140 |
| aacaacggga | gtcaggcagt | aggacgctct | tcatttacta | gcctggagta | ctttccttct | 1200 |
| cagatgctgc | gtaccggaaa | caactttacc | ttcagctaca | cttttgagga | cgttcctttc | 1260 |
| cacagcagct | acgctcacag | ccagagtctg | gaccgtctca | tgaatcctct | catcgaccag | 1320 |

```
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt ttcctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cctagcactc ggcgaaacaa caagacctgc taggcaagca   1800
gctaccgcag atgtcaacac acaaggcgtt cttccaggca tggtctggca ggacagagat   1860
gtgtaccttc aggggcccat ctgggcaaag attccacaca cggacggaca ttttcacccc   1920
tctcccctca tgggtggatt cggacttaaa caccctcctc cccagattct catcaagaac   1980
accccggtac ctgcgaatcc ttcgaccacc ttcagtgcgg caaagtttgc ttccttcatc   2040
acacagtact ccacgggaca ggtcagcgtg gagatcgagt gggagctgca gaaggaaaac   2100
agcaaacgct ggaatcccga aattcagtac acttccaact acaacaagtc tattaatgtg   2160
gactttactg tggacactaa tggcgtgtat tcagagcctc gccccattgg caccagatac   2220
ctgactcgta atctgtaa                                                  2238

<210> SEQ ID NO 12
<211> LENGTH: 740
<212> TYPE: PRT
<213> ORGANISM: Artificial Sequence
<220> FEATURE:
<223> OTHER INFORMATION: constructed sequence

<400> SEQUENCE: 12

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
```

-continued

```
            195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Thr
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
                275                 280                 285
Cys His Phe Ser Pro Arg Asp Trp Gln Arg Leu Ile Asn Asn Asn Trp
290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
                435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
                515                 520                 525
Asp Glu Glu Lys Phe Phe Pro Gln Ser Gly Val Leu Ile Phe Gly Lys
                530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Leu Ala Leu Gly Glu
                580                 585                 590
Thr Thr Arg Pro Ala Arg Gln Ala Ala Thr Ala Asp Val Asn Thr Gln
                595                 600                 605
Gly Val Leu Pro Gly Met Val Trp Gln Asp Arg Asp Val Tyr Leu Gln
610                 615                 620
```

```
Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
            645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Ile Asn Val
705                 710                 715                 720

Asp Phe Thr Val Asp Thr Asn Gly Val Tyr Ser Glu Pro Arg Pro Ile
                725                 730                 735

Gly Thr Arg Tyr
            740

<210> SEQ ID NO 13
<211> LENGTH: 20
<212> TYPE: DNA
<213> ORGANISM: Artificial Sequence
<220> FEATURE:
<223> OTHER INFORMATION: constructed sequence

<400> SEQUENCE: 13
gcctgttcct gcttgcttac                                           20

<210> SEQ ID NO 14
<211> LENGTH: 22
<212> TYPE: DNA
<213> ORGANISM: Artificial Sequence
<220> FEATURE:
<223> OTHER INFORMATION: constructed sequence

<400> SEQUENCE: 14
tgctttccaa agtaagcaca aa                                        22

<210> SEQ ID NO 15
<211> LENGTH: 20
<212> TYPE: DNA
<213> ORGANISM: Artificial Sequence
<220> FEATURE:
<223> OTHER INFORMATION: constructed sequence

<400> SEQUENCE: 15
cctggcctcc agacaagtag                                           20
```